(12) United States Patent
Commons et al.

(10) Patent No.: US 7,618,990 B2
(45) Date of Patent: Nov. 17, 2009

(54) OXAZOLIDONE DERIVATIVES AS PR MODULATORS

(75) Inventors: Thomas Joseph Commons, Wayne, PA (US); Andrew Fensome, Wayne, PA (US); Gavin David Heffernan, Florence, NJ (US); Casey Cameron McComas, Phoenixville, PA (US); Richard Page Woodworth, Jr., North Wales, PA (US); Michael Byron Webb, Douglassville, PA (US); Michael Anthony Marella, Limerick, PA (US); Edward George Melenski, Collegeville, PA (US); Ronald Charles Bernotas, Royersford, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 11/891,748

(22) Filed: Aug. 13, 2007

(65) Prior Publication Data

US 2008/0045556 A1 Feb. 21, 2008

Related U.S. Application Data

(60) Provisional application No. 60/837,898, filed on Aug. 15, 2006.

(51) Int. Cl.
*A61K 31/427* (2006.01)
*C07D 277/38* (2006.01)

(52) U.S. Cl. ...................... 514/370; 548/190
(58) Field of Classification Search ................ 514/278, 514/361, 365, 374, 370, 376; 546/16; 548/128, 548/205, 311.1, 190, 229
See application file for complete search history.

(56) References Cited

U.S. PATENT DOCUMENTS

| | | | |
|---|---|---|---|
| 3,474,462 A | 10/1969 | Breuer | |
| 4,008,243 A | 2/1977 | Wikel et al. | |
| 4,150,028 A | 4/1979 | Paget et al. | |
| 4,216,313 A | 8/1980 | Paget et al. | |
| 4,268,679 A | 5/1981 | Lavanish | |
| 4,293,558 A | 10/1981 | Paget et al. | |
| 4,426,527 A | 1/1984 | Lavanish et al. | |
| 4,756,744 A | 7/1988 | Schwindemann | |
| 5,714,607 A | 2/1998 | Padmanathan | |
| 5,719,136 A | 2/1998 | Chwalisz et al. | |
| 5,827,857 A | 10/1998 | Riedl | |
| 5,972,372 A | 10/1999 | Saleh et al. | |
| 6,125,850 A | 10/2000 | Sokal et al. | |
| 6,126,958 A | 10/2000 | Saleh | |
| 6,239,152 B1 | 5/2001 | Gordeev et al. | |
| 6,436,966 B1 | 8/2002 | Ohkawa et al. | |
| 6,531,470 B1 | 3/2003 | Gordeev et al. | |
| 2002/0115669 A1 | 8/2002 | Wiedeman et al. | |
| 2002/0183371 A1 | 12/2002 | Gordeev et al. | |
| 2003/0114491 A1 | 6/2003 | Kim et al. | |
| 2004/0157883 A1 | 8/2004 | Chen et al. | |
| 2004/0167192 A1 | 8/2004 | Solow-Cordero et al. | |
| 2004/0214870 A1 | 10/2004 | Xin et al. | |

FOREIGN PATENT DOCUMENTS

| | | |
|---|---|---|
| DE | 32 27 329 A1 | 1/1984 |
| DE | 196 04 223 A1 | 8/1997 |
| DE | 196 49 095 A1 | 8/1997 |
| DE | 100 34 622 A1 | 1/2002 |
| DE | 100 34 623 A1 | 1/2002 |
| DE | 100 34 628 A1 | 1/2002 |
| EP | 0 300 272 B1 | 9/1992 |
| EP | 0 693 491 A | 1/1996 |
| EP | 0 770 613 B1 | 10/1996 |
| EP | 0 789 026 A1 | 8/1997 |
| EP | 0 894 497 B1 | 7/1998 |
| EP | 0 789 025 B1 | 4/2001 |
| GB | 1224995 | 3/1971 |
| NL | 6703864 | 3/1967 |
| NL | 6706448 | 5/1967 |
| WO | WO 92/07567 A1 | 5/1992 |
| WO | WO 92/09586 A1 | 6/1992 |
| WO | 7-149745 | 6/1995 |
| WO | WO 95/15955 A1 | 6/1995 |
| WO | WO 98/04534 A1 | 2/1998 |
| WO | WO 99/42455 A1 | 8/1999 |
| WO | WO 01/70733 A2 | 9/2001 |

(Continued)

OTHER PUBLICATIONS

Wolff et al., Burger's Medicinal Chemistry and Drug Discovery, 1994, Wiley-Interscience, Fifth Edition, vol. I: Principles and Practice, pp. 975-977.*

(Continued)

*Primary Examiner*—Kamal A Saeed
*Assistant Examiner*—Kristin Bianchi
(74) *Attorney, Agent, or Firm*—Stephen E. Johnson; Fariba Shoarinejad

(57) ABSTRACT

Compounds of the following structure are described:

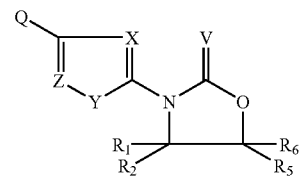

wherein $R_1$, $R_2$, $R_5$, $R_6$, V, X, Y, Z and Q are described herein, or a pharmaceutically acceptable salt, tautomer, metabolite or prodrug thereof. These compounds are useful for treating a variety of hormone-related conditions including contraception, treating or preventing fibroids, endometriosis, dysfunctional bleeding, uterine leiomyomata, polycystic ovary syndrome, or hormone-dependent carcinomas, providing hormone replacement therapy, stimulating food intake or synchronizing estrus.

24 Claims, No Drawings

FOREIGN PATENT DOCUMENTS

| WO | WO 01/74811 A2 | 10/2001 |
| WO | WO 02/081453 A1 | 10/2002 |
| WO | WO 03/011859 A2 | 2/2003 |
| WO | WO 03/101985 A1 | 12/2003 |
| WO | WO 2004/014899 A1 | 2/2004 |
| WO | WO 2004/019938 A1 | 3/2004 |
| WO | WO 2004/087698 A2 | 10/2004 |
| WO | WO 2004/089303 A2 | 10/2004 |
| WO | WO 2005/005435 A1 | 1/2005 |

OTHER PUBLICATIONS

Metabolomics [online], Retrieved from the Internet Jun. 16, 2008, www.en.wikipedia.org/wiki/Metabolomics.*

Kwon et al., Handbook of Essential Pharmacokinetics, Pharmacodynamics and Drug Metabolism for Industrial Scientists, 2001, http://www.myilibrary.com/Browse/open.asp?ID=4284&loc=1, Retrieved from the Internet Jun. 16, 2008, p. 213.*

U.S. Appl. No. 11/891,729, filed Aug. 13, 2007, Commons et al.
U.S. Appl. No. 11/891,727, filed Aug. 13, 2007, Commons et al.
U.S. Appl. No. 11/891,821, filed Aug. 13, 2007, Commons et al.
U.S. Appl. No. 11/891,728, filed Aug. 13, 2007, Commons et al.
U.S. Appl. No. 11/891,747, filed Aug. 13, 2007, Commons et al.

David J. Mangelsdorf, Carl Thummel, Miguel Beato, Peter Herrlich, Günther Schütz, Kazuhiko Umesono, Bruce Blumberg, Philippe Kastner, Manuel Mark, Pierre Chambon and Ronald M. Evans, The nuclear receptor superfamily: The second decade, Cell, vol. 83, Issue 6, Dec. 15, 1995, pp. 835-839.

André Ulmann, Rémi Peyron and Louise Silvestre, Clinical Uses of Mifepristone (MFP), Annals of the New York Academy of Sciences, Jun. 1995—vol. 761 Steroid Receptors and Antihormones, pp. 248-260.

Kekkonen, et al, Fertility and Sterility, 60, 610, 1993.

Horwitz, et al, Horm. Cancer, 283, 1996, pub: Birkhaeuser, Boston, Mass., ed. Vedeckis.

AA Murphy, LM Kettel, AJ Morales, VJ Roberts, and SS Yen, Regression of uterine leiomyomata in response to the antiprogesterone RU 486, J Clin Endocrinol Metab 1993 76: 513-517.

Kettel, et al., Fertility and Sterility, 56, 402, 1991.

Horst Michna, Karsten Parczyk, Martin R. Schneider and Yukishige Nishino, Differentiation Therapy with Progesterone Antagonists Annals of the New York Academy of Sciences, Jun. 1995—vol. 761 Steroid Receptors and Antihormones, pp. 224-247.

B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

Lautens, M.; Roy, A.: Synthetic Studies of the Formulation of Oxazoles and Isoxazoles from N-Acetoacetyl Derivatives Organic Letters, vol. 2, No. 4, 2000, pp. 555-557.

Collins et al., Novel pyrrole-containing progesterone receptor modulators, Bioorganic & Medicinal Chemistry Letters, 2004, vol. 14, pp. 2185-2189.

* cited by examiner

OXAZOLIDONE DERIVATIVES AS PR MODULATORS

CROSS-REFERENCE TO RELATED APPLICATIONS

This application claims the benefit of the priority of U.S. Provisional Patent Application No. 60/837,898, filed Aug. 15, 2006.

BACKGROUND OF THE INVENTION

This invention relates to modulators of the progesterone receptor, their preparation and utility.

Intracellular receptors (IR) form a class of structurally related gene regulators known as "ligand dependent transcription factors" (Mangelsdorf, D. J. etc. Cell, 83, 835, 1995). The steroid receptor family is a subset of the IR family, including the progesterone receptor (PR), estrogen receptor (ER), androgen receptor (AR), glucocorticoid receptor (GR), and mineralocorticoid receptor (MR).

The natural hormone, or ligand, for the PR is the steroid progesterone, but synthetic compounds, such as medroxyprogesterone acetate or levonorgestrel, have been made which also serve as PR ligands. Once a ligand is present in the fluid surrounding a cell, it passes through the membrane via passive diffusion, and binds to the IR to create a receptor/ligand complex. This complex binds to specific gene promoters present in the cell's DNA. Once bound to the DNA, the complex modulates the production of mRNA and the protein encoded by that gene.

A compound that binds to an IR and mimics the action of the natural hormone is termed an agonist, whilst a compound which inhibits the effect of the hormone is an antagonist.

PR agonists (natural and synthetic) are known to play an important role in the health of women. PR agonists are used in birth control formulations, either alone or in the presence of an ER agonist.

PR antagonists may also be used in contraception (Ulmann, et al., Ann. N.Y. Acad. Sci., 261, 248, 1995; Kekkonen, et al, Fertility and Sterility, 60, 610, 1993; or U.S. Pat. No. 5,719,136); for the treatment of hormone dependent breast cancers (Horwitz, et al, Horm. Cancer, 283, 1996, pub: Birkhaeuser, Boston, Mass., ed. Vedeckis), uterine and ovarian cancers, non-malignant chronic conditions such as uterine fibroids (Murphy, et al, J. Clin. Endo. Metab., 76, 513, 1993) and endometriosis (Kettel, et al., Fertility and Sterility, 56, 402, 1991), hormone dependent prostate cancer (Michna, et al, Ann. N.Y. Acad. Sci., 761, 224, 1995); and for hormone replacement therapy (U.S. Pat. No. 5,719,136).

What is needed in the art are alternative progesterone receptor modulators.

SUMMARY OF THE INVENTION

In one aspect, progesterone receptor modulators of the following structure are provided:

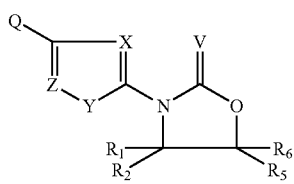

wherein $R_1$, $R_2$, $R_5$, $R_6$, V, X, Y, Z, and Q are defined herein.

In a further aspect, compounds of the following structure are provided:

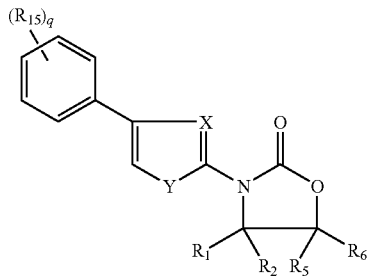

wherein $R_1$, $R_2$, $R_5$, $R_6$, X, Y, $R_{15}$, and q are defined herein.

In yet another aspect, compounds of the following structure are provided:

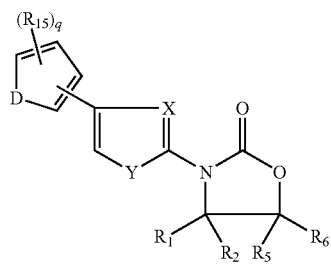

wherein $R_1$, $R_2$, $R_5$, $R_6$, X, Y, D, $R_{15}$, and q are defined herein.

In still a further aspect, methods of contraception using the compounds described herein are provided.

In yet another aspect, methods of treating or preventing fibroids using the compounds described herein are provided.

In a further aspect, methods for treating or preventing endometriosis, dysfunctional bleeding, uterine leiomyomata, polycystic ovary syndrome, or hormone-dependent carcinomas using the compounds described herein are provided.

In still a further aspect, methods of providing hormone replacement therapy using the compounds described herein are provided.

In another aspect, methods of stimulating food intake or synchronizing estrus using the compounds described herein are provided.

Other aspects and advantages of the invention will be readily apparent from the following detailed description of the invention.

DETAILED DESCRIPTION OF THE INVENTION

Novel compounds, which are useful as progesterone receptor modulators, are described. These compounds are useful in treating and/or preventing a variety of hormone-related conditions as described below.

I. The Compounds

The compounds described herein have the following general structure:

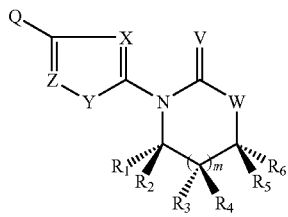

wherein, $R_1$, $R_2$, $R_3$, $R_4$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_n C(H)_{3-p}(R_7)_p$, —$(CH_2)_n COOR_8$, or —$(CH_2)_p$—O—$R_9$; or $R_1$, $R_2$ or $R_3$, $R_4$ or $R_5$, $R_6$ are taken together to form a carbon-based 3 to 6 membered saturated ring; or when m is 0, $R_1$ or $R_2$ forms a carbon-based 5 to 7 membered saturated ring with $R_5$ or $R_6$; or $R_1$ or $R_2$ forms a carbon-based 6-membered aromatic ring with $R_5$ or $R_6$; $R_7$ is halogen; $R_8$ is $C_1$ to $C_6$ alkyl; $R_9$ is H, $C_1$ to $C_6$ alkyl, or $C_1$ to $C_3$ perfluoroalkyl; W is O, $NR_{10}$ or $CR_{11}R_{12}$; $R_{10}$ is H, $C_1$ to $C_6$ alkyl, or $(CH_2)_n$-aryl; $R_{11}$ and $R_{12}$ are, independently, H, $C_1$ to $C_6$ alkyl, or —$(CH_2)_n$-aryl; or $R_{11}$ or $R_{12}$ forms a double bond with $R_5$ or $R_6$; V is O, S or $NR_{13}$; or when m is 0, W is O, $R_1$ and $R_2$ are H or are taken together with oxygen to form a carbonyl group, V is —$(CH_3)_2$; or when m is 1, V is O and W is $CR_{11}R_{12}$ then $R_1$ or $R_2$ can form a two carbon bridge with $R_{11}$ or $R_{12}$; $R_{13}$ is H, $C_1$ to $C_6$ alkyl, $(CH_2)_n$-aryl, $(CH_2)_n$—CN, CO—$(C_1$ to $C_6$ alkyl), CO—$(CH_2)_n$-aryl, $SO_2$—$(C_1$ to $C_6$ alkyl), or $SO_2$—$(CH_2)_n$-aryl; X and Z are, independently, N or $CR_{14}$; $R_{14}$ is $C_1$ to $C_6$ alkyl, —$(CH_2)_n$-aryl, —$(CH_2)_n$—O—$(CH_2)_n$-alkyl, —$(CH_2)_n$—O—$(CH_2)_n$-aryl, halogen, hydroxy, $C_1$ to $C_3$ perfluoroalkyl, $C_1$ to $C_3$ perfluoroalkoxy or $(CH_2)_n$—CN; or when Z is $CR_{14}$, $R_{14}$ forms a two carbon saturated or unsaturated bond with Q to provide a tricyclic ring system; Y is S; or Y is O when X is N and Z is $CR_{14}$; Q is aryl, substituted aryl, heteroaryl, or substituted heteroaryl; m is 0 or 1; n is 0 to 3; and p is 1 to 3, or a pharmaceutically acceptable salt, tautomer, metabolite or prodrug thereof.

In one embodiment, the compounds are of the structure:

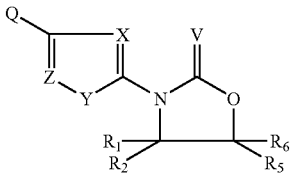

wherein, $R_1$, $R_2$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_n C(H)_{3-p}(R_7)_p$, —$(CH_2)_n COOR_8$, or —$(CH_2)_p$—O—$R_9$; or $R_1$, $R_2$ or $R_5$, $R_6$ are taken together to form a carbon-based 3 to 6 membered saturated ring; or $R_1$ or $R_2$ forms a carbon-based 5 to 7 membered saturated ring with $R_5$ or $R_6$; or $R_1$ or $R_2$ forms a carbon-based 6-membered aromatic ring with $R_5$ or $R_6$; $R_7$ is halogen; $R_8$ is $C_1$ to $C_6$ alkyl; $R_9$ is H, $C_1$ to $C_6$ alkyl, or $C_1$ to $C_3$ perfluoroalkyl; V is O or S; X and Z are, independently, N or $CR_{14}$; $R_{14}$ is $C_1$ to $C_6$ alkyl, —$(CH_2)_n$-aryl, —$(CH_2)_n$—O—$(CH_2)_n$-alkyl, —$(CH_2)_n$—O—$(CH_2)_n$-aryl, halogen, hydroxy, $C_1$ to $C_3$ perfluoroalkyl, $C_1$ to $C_3$ perfluoroalkoxy, or —$(CH_2)_n$—CN; Y is O or S; Q is aryl, substituted aryl, heteroaryl or substituted heteroaryl; n is 0 to 3; p is 1 to 3 or a pharmaceutically acceptable salt, tautomer, metabolite or prodrug thereof.

V is suitably O. m is suitably 0. $R_1$ and $R_2$ are suitably independently $C_1$ to $C_{10}$ alkyl. $R_5$ and $R_6$ are suitably independently H. X is suitably N. Z is suitably $CR_{14}$.

In a further embodiment, V is O; $R_1$ and $R_2$ are $C_1$ to $C_{10}$ alkyl; and $R_5$ and $R_6$ are H.

In another embodiment, X is N; Y is S; and Z is $CR_{14}$.

In a still further embodiment, X and Z are N and Y is S.

In yet another embodiment, X is N; Y is O; and Z is $CR_{14}$.

In a further embodiment, V is O; $R_1$ and $R_2$ are $C_1$ to $C_{10}$ alkyl; $R_5$ and $R_6$ are H; X is N; Y is S; and Z is $CR_{14}$.

In another embodiment, Q is aryl or substituted aryl.

In a further embodiment, Q is an optionally substituted benzene ring. The optionally substituted benzene ring may be substituted by one or more of $R_{15}$ and $R_{15}$ is —$(CH_2)_n CN$, halogen, $NO_2$, —$C(NH_2)$=N—OH, $C_1$ to $C_3$ perfluoroalkyl, $C_1$ to $C_3$ perfluoroalkoxy, —O—$(C_1$ to $C_4$ alkyl), —O—$(C_1$ to $C_4$ substituted alkyl), —$SO_2$—$(C_1$ to $C_4$ alkyl), —$SO_2$—$(C_1$ to $C_4$ substituted alkyl), —CO—$(C_1$ to $C_4$ alkyl), —CO—$(C_1$ to $C_4$ substituted alkyl), $C_1$ to $C_4$ alkyl, $C_1$ to $C_4$ substituted alkyl, —O—$(CH_2)_n$-aryl, —COO—$(C_1$ to $C_4$ alkyl), —COO—$(C_1$ to $C_4$ substituted alkyl), —CONH—$(C_1$ to $C_3$ alkyl), —CON—$(C_1$ to $C_3$ alkyl)$_2$, aryl, substituted aryl, heteroaryl, or substituted heteroaryl. Desirably, the benzene ring is substituted by one or more, e.g., 1 to 4 of $R_{15}$ which are the same or different, preferably $R_{15}$ is CN or Br.

The compound described herein therefore can be of the following structure, wherein the $R_{15}$ group is bound to one or more of the carbon-atoms of the benzene ring:

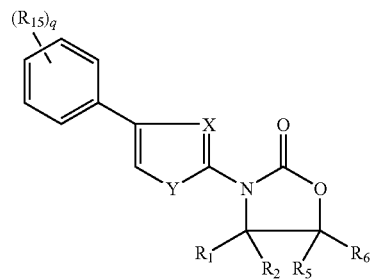

wherein, $R_1$, $R_2$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_n C(H)_{3-p}(R_7)_p$, —$(CH_2)_n COOR_8$, or —$(CH_2)_p$—O—$R_9$; or $R_1$, $R_2$ or $R_5$, $R_6$ are taken together to form a carbon-based 3 to 6 membered saturated ring; or $R_1$ or $R_2$ forms a carbon-based 5 to 7 membered saturated ring with $R_5$ or $R_6$; or $R_1$ or $R_2$ forms a carbon-based 6-membered aromatic ring with $R_5$ or $R_6$; $R_7$ is halogen; $R_8$ is $C_1$ to $C_6$ alkyl; $R_9$ is H, $C_1$ to $C_6$ alkyl, or $C_1$ to $C_3$ perfluoroalkyl; $R_{15}$ is —$(CH_2)_n CN$, halogen, $NO_2$, —$C(NH_2)$=N—OH, $C_1$ to $C_3$ perfluoroalkyl, $C_1$ to $C_3$ perfluoroalkoxy, —O—$(C_1$ to $C_4$ alkyl), —O—$(C_1$ to $C_4$ substituted alkyl), —$SO_2$—$(C_1$ to $C_4$ alkyl), —$SO_2$—$(C_1$ to $C_4$ substituted alkyl), —CO—$(C_1$ to $C_4$ alkyl), —CO—$(C_1$ to $C_4$ substituted alkyl), $C_1$ to $C_4$ alkyl, $C_1$ to $C_4$ substituted alkyl, —O—$(CH_2)_n$-aryl, —COO—$(C_1$ to $C_4$ alkyl), —COO—$(C_1$ to $C_4$ substituted alkyl), —CONH—$(C_1$ to $C_3$ alkyl), —CON—$(C_1$ to $C_3$ alkyl)$_2$, aryl, substituted aryl, heteroaryl, or substituted heteroaryl; X is N or $CR_{14}$; $R_{14}$ is $C_1$ to $C_6$ alkyl, —$(CH_2)_n$-aryl, —$(CH_2)_n$—O—$(CH_2)_n$-alkyl, —$(CH_2)_n$—O—$(CH_2)_n$-aryl, halogen, hydroxy, $C_1$ to $C_3$ perfluoroalkyl, $C_1$ to $C_3$ perfluoroalkoxy, or —$(CH_2)_n$—CN; Y is O or S; n is 0 to 3; and p is 1 to 3; and q is 0 to 4, or a pharmaceutically acceptable salt, tautomer, metabolite or prodrug thereof. Desirably, $R_1$, $R_2$, $R_5$, and $R_6$ are independently H or $C_1$ to $C_{10}$ alkyl.

In a further embodiment, Q is heteroaryl or substituted heteroaryl. The heteroaryl ring may be substituted by one or more $R_{15}$, wherein $R_{15}$ is —$(CH_2)_n$CN, halogen, $NO_2$, —$C(NH_2)$=N—OH, $C_1$ to $C_3$ perfluoroalkyl, $C_1$ to $C_3$ perfluoroalkoxy, —O—($C_1$ to $C_4$ alkyl), —O—($C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—$(CH_2)_n$-aryl, —COO—($C_1$ to $C_4$ alkyl), —COO—($C_1$ to $C_{10}$ substituted alkyl), —CONH—($C_1$ to $C_3$ alkyl), —CON—($C_1$ to $C_3$ alkyl)$_2$, aryl, substituted aryl, heteroaryl, or substituted heteroaryl.

The compound described herein may, therefore, be of the structure, wherein the $R_{15}$ group is bound to one or more of the carbon-atoms of the heterocyclic group:

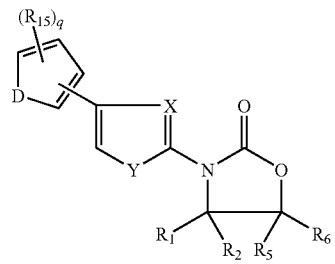

wherein, $R_1$, $R_2$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_n$C$(H)_{3-p}(R_7)_p$, —$(CH_2)_n$COOR$_8$, or —$(CH_2)_p$—O—$R_9$; or $R_1$, $R_2$ or $R_5$, $R_6$ are taken together to form a carbon-based 3 to 6 membered saturated ring; or $R_1$ or $R_2$ forms a carbon-based 5 to 7 membered saturated ring with $R_5$ or $R_6$; or $R_1$ or $R_2$ forms a carbon-based 6-membered aromatic ring with $R_5$ or Rr; $R_7$ is halogen; $R_8$ is $C_1$ to $C_6$ alkyl; $R_9$ is H, $C_1$ to $C_6$ alkyl, or $C_1$ to $C_3$ perfluoroalkyl; D is S, NR$_{16}$, or O; $R_{15}$ is —$(CH_2)_n$CN, halogen, $NO_2$, —$C(NH_2)$=N—OH, $C_1$ to $C_3$ perfluoroalkyl, $C_1$ to $C_3$ perfluoroalkoxy, —O—($C_1$ to $C_4$ alkyl), —O—($C_1$ to $C_4$ substituted alkyl), —$SO_2$—($C_1$ to $C_4$ alkyl), —$SO_2$—($C_1$ to $C_4$ substituted alkyl), —CO—($C_1$ to $C_4$ alkyl), —CO—($C_1$ to $C_4$ substituted alkyl), $C_1$ to $C_4$ alkyl, $C_1$ to $C_4$ substituted alkyl, —O—$(CH_2)_n$- aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, substituted aryl, heteroaryl, or substituted heteroaryl; $R_{16}$ is H, $C_1$ to $C_{10}$ alkyl, $C_1$ to $C_{10}$ substituted alkyl, or —COO—($C_1$ to $C_{10}$ alkyl); X is N or CR$_{14}$; $R_{14}$ is $C_1$ to $C_6$ alkyl, —$(CH_2)_n$-aryl, —$(CH_2)_n$—O—$(CH_2)_n$-alkyl, —$(CH_2)_n$—O—$(CH_2)_n$-aryl, halogen, hydroxy, $C_1$ to $C_3$ perfluoroalkyl, $C_1$ to $C_3$ perfluoroalkoxy, or —$(CH_2)_n$—CN; Y is O or S; n is 0 to 3; and p is 1 to 3; and q is 0 to 3, or a pharmaceutically acceptable salt, tautomer, metabolite or prodrug thereof. Desirably, $R_1$, $R_2$, $R_5$, and $R_6$ are, independently, H or $C_1$ to $C_{10}$ alkyl.

In another embodiment, the compound is of the structure:

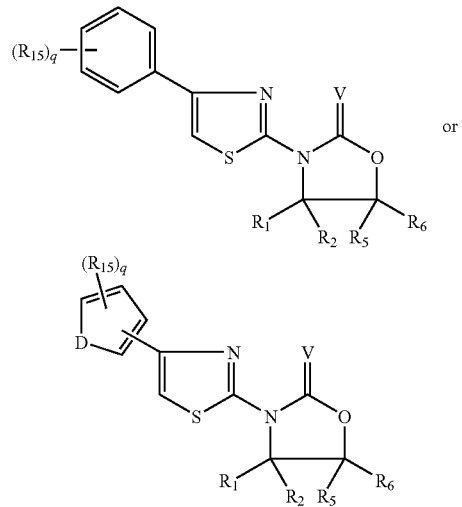

wherein, $R_1$, $R_2$, $R_5$ and $R_6$ are, independently, H, $C_1$ to $C_{10}$ alkyl, —$(CH_2)_n$-aryl, —$(CH_2)_p$—O—$(CH_2)_n$-aryl, —$(CH_2)_n$C$(H)_{3-p}(R_7)_p$, —$(CH_2)_n$COOR$_8$, or —$(CH_2)_p$—O—$R_9$; or $R_1$, $R_2$ or $R_5$, $R_6$ are taken together to form a carbon-based 3 to 6 membered saturated ring; or $R_1$ or $R_2$ forms a carbon-based 5 to 7 membered saturated ring with $R_5$ or $R_6$; or $R_1$ or $R_2$ forms a carbon-based 6-membered aromatic ring with $R_5$ or $R_6$; $R_7$ is halogen; $R_8$ is $C_1$ to $C_6$ alkyl; $R_9$ is H, $C_1$ to $C_6$ alkyl, or $C_1$ to $C_3$ perfluoroalkyl; D is S, NR$_{16}$, or O; $R_{15}$ is —$(CH_2)_n$CN, halogen, $NO_2$, —$C(NH_2)$=N—OH, $C_1$ to $C_3$ perfluoroalkyl, $C_1$ to $C_3$ perfluoroalkoxy, —O—($C_1$ to $C_4$ alkyl), —$SO_2$—($C_1$ to $C_4$ alkyl), —CO—($C_1$ to $C_4$ alkyl), $C_1$ to $C_4$ alkyl, —O—$(CH_2)_n$-aryl, —COO—($C_1$ to $C_4$ alkyl), —COO—($C_1$ to $C_4$ substituted alkyl), —CONH—($C_1$ to $C_3$ alkyl), —CON—($C_1$ to $C_3$ alkyl)$_2$, aryl, or heteroaryl; $R_{16}$ is H, $C_1$ to $C_{10}$ alkyl, $C_1$ to $C_{10}$ substituted alkyl, or —COO—($C_1$ to $C_{10}$ alkyl); V is O or S; n is 0 to 3; p is 1 to 3; q is 0 to 3; or a pharmaceutically acceptable salt, tautomer, metabolite, or prodrug thereof. Desirably, $R_1$, $R_2$, $R_5$ and $R_6$ are, independently, H or $C_1$ to $C_{10}$ alkyl.

In still a further embodiment, the compound is of the structure:

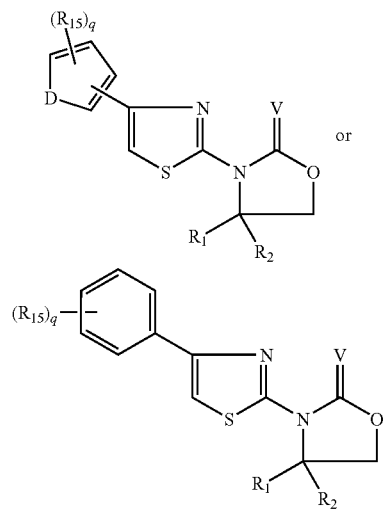

wherein, $R_1$ and $R_2$ are, independently, H, $C_1$ to $C_{10}$ alkyl, —$(CH_2)_n$-aryl, —$(CH_2)_p$—O—$(CH_2)_n$-aryl, —$(CH_2)_n$C$(H)_{3-p}(R_7)_p$, —$(CH_2)_n COOR_8$, or —$(CH_2)_p$—O—$R_9$; or $R_1$ and $R_2$ are taken together to form a carbon-based 3 to 6-membered saturated ring; $R_7$ is halogen; $R_8$ is $C_1$ to $C_6$ alkyl; $R_9$ is H, $C_1$ to $C_6$ alkyl, or $C_1$ to $C_3$ perfluoroalkyl; D is S, $NR_{16}$, or O; $R_{15}$ is —$(CH_2)_n CN$, halogen, $NO_2$, —$C(NH_2)$=N—OH, $C_1$ to $C_3$ perfluoroalkyl, $C_1$ to $C_3$ perfluoroalkoxy, —O—($C_1$ to $C_4$ alkyl), —$SO_2$—($C_1$ to $C_4$ alkyl), —CO—($C_1$ to $C_4$ alkyl), $C_1$ to $C_4$ alkyl, —O—$(CH_2)_n$-aryl, —CONH—($C_1$ to $C_3$ alkyl), —CON—($C_1$ to $C_3$ alkyl)$_2$, aryl, —COO—($C_1$ to $C_4$ alkyl), or heteroaryl; $R_{16}$ is H, $C_1$ to $C_{10}$ alkyl, $C_1$ to $C_{10}$ substituted alkyl, or —COO—($C_1$ to $C_{10}$ alkyl); V is O or S; n is 0 to 3; p is 1 to 3; q is 0 to 3; or a pharmaceutically acceptable salt, tautomer, metabolite, or prodrug thereof. Desirably, $R_1$ and $R_2$ are, independently, H or $C_1$ to $C_{10}$ alkyl.

In yet another embodiment, the compound is of the structure:

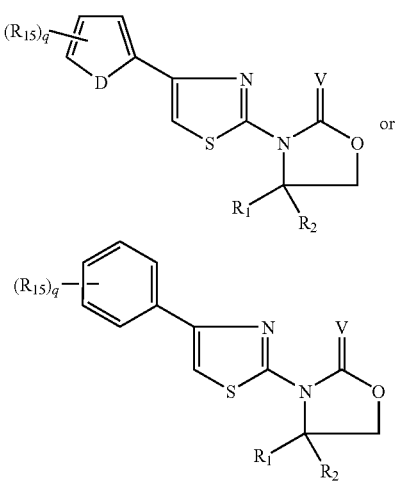

or wherein, $R_1$ and $R_2$ are, independently, H, $C_1$ to $C_{10}$ alkyl, —$(CH_2)_n$-aryl, —$(CH_2)_p$—O—$(CH_2)_n$-aryl, —$(CH_2)_n$C$(H)_{3-p}(R_7)_p$, —$(CH_2)_n COOR_8$, or —$(CH_2)_p$—O—$R_9$; or $R_1$ and $R_2$ are taken together to form a carbon-based 3 to 6-membered saturated ring; $R_7$ is halogen; $R_8$ is $C_1$ to $C_6$ alkyl; $R_9$ is H, $C_1$ to $C_6$ alkyl, or $C_1$ to $C_3$ perfluoroalkyl; D is S, $NR_{16}$, or O; $R_{15}$ is —$(CH_2)_n CN$, halogen, $NO_2$, —$C(NH_2)$=N—OH, $C_1$ to $C_3$ perfluoroalkyl, $C_1$ to $C_3$ perfluoroalkoxy, —O—($C_1$ to $C_4$ alkyl), —$SO_2$—($C_1$ to $C_4$ alkyl), —CO—($C_1$ to $C_4$ alkyl), $C_1$ to $C_4$ alkyl, —O—$(CH_2)_n$-aryl, —CONH—($C_1$ to $C_3$ alkyl), —CON—($C_1$ to $C_3$ alkyl)$_2$, aryl, —COO—($C_1$ to $C_4$ alkyl), or heteroaryl; $R_{16}$ is H, $C_1$ to $C_{10}$ alkyl, $C_1$ to $C_{10}$ substituted alkyl, or —COO—($C_1$ to $C_{10}$ alkyl); V is O or S; n is 0 to 3; p is 1 to 3; q is 0 to 3; or a pharmaceutically acceptable salt, tautomer, metabolite, or prodrug thereof. Desirably, $R_1$ and $R_2$ are, independently, H or $C_1$ to $C_{10}$ alkyl.

In a further embodiment, the compound is of the structure:

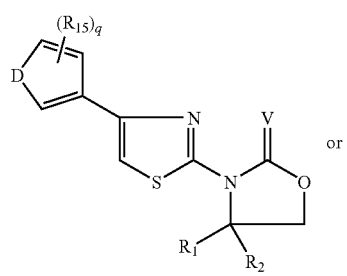

or

-continued wherein, $R_1$ and $R_2$ are, independently, H, $C_1$ to $C_{10}$ alkyl, —$(CH_2)_n$-aryl, —$(CH_2)_p$—O—$(CH_2)_n$-aryl, —$(CH_2)_n$C$(H)_{3-p}(R_7)_p$, —$(CH_2)_n COOR_8$, or —$(CH_2)_p$—O—$R_9$; or $R_1$ and $R_2$ are taken together to form a carbon-based 3 to 6-membered saturated ring; $R_7$ is halogen; $R_8$ is $C_1$ to $C_6$ alkyl; $R_9$ is H, $C_1$ to $C_6$ alkyl, or $C_1$ to $C_3$ perfluoroalkyl; D is S, $NR_{16}$, or O; $R_{15}$ is —$(CH_2)_n CN$, halogen, $NO_2$, —$C(NH_2)$=N—OH, $C_1$ to $C_3$ perfluoroalkyl, $C_1$ to $C_3$ perfluoroalkoxy, —O—($C_1$ to $C_4$ alkyl), —$SO_2$—($C_1$ to $C_4$ alkyl), —CO—($C_1$ to $C_4$ alkyl), $C_1$ to $C_4$ alkyl, —O—$(CH_2)_n$-aryl, —CONH—($C_1$ to $C_3$ alkyl), —CON—($C_1$ to $C_3$ alkyl)$_2$, aryl, —COO—($C_1$ to $C_4$ alkyl), or heteroaryl; $R_{16}$ is H, $C_1$ to $C_{10}$ alkyl, $C_1$ to $C_{10}$ substituted alkyl, or —COO—($C_1$ to $C_{10}$ alkyl); V is O or S; n is 0 to 3; p is 1 to 3; q is 0 to 3; or a pharmaceutically acceptable salt, tautomer, metabolite, or prodrug thereof. Desirably, $R_1$ and $R_2$ are, independently, H or $C_1$ to $C_{10}$ alkyl.

The compound described herein may be selected from among 3-[4-(4-Chlorophenyl)-1,3-thiazol-2-yl]-1,3-oxazolidin-2-one, 3-[4-(4-Bromophenyl)-1,3-thiazol-2-yl]-1,3-oxazolidin-2-one, 4-[2-(2-Oxo-1,3-oxazolidin-3-yl)-1,3-thiazol-4-yl]benzonitrile, 3-[4-(4-Bromophenyl)-1,3-thiazol-2-yl]-4-methyl-1,3-oxazolidin-2-one, 4-[2-(4-Methyl-2-oxo-1,3-oxazolidin-3-yl)-1,3-thiazol-4-yl]benzonitrile, (4S)-3-[4-(4-Bromophenyl)-1,3-thiazol-2-yl]-4-methyl-1,3-oxazolidin-2-one, (4R)-3-[4-(4-Bromophenyl)-1,3-thiazol-2-yl]-4-methyl-1,3-oxazolidin-2-one, 4-{2-[(4S)-4-Methyl-2-oxo-1,3-oxazolidin-3-yl]-1,3-thiazol-4-yl}benzonitrile, 4-{2-[(4R)-4-Methyl-2-oxo-1,3-oxazolidin-3-yl]-1,3-thiazol-4-yl}benzonitrile, (4R)-3-[4-(3-bromophenyl)-1,3-thiazol-2-yl]-4-methyl-1,3-oxazolidin-2-one, 3-{2-[(4R)-4-Methyl-2-oxo-1,3-oxazolidin-3-yl]-1,3-thiazol-4-yl}benzonitrile, 3-[4-(4-Bromophenyl)-1,3-thiazol-2-yl]-4-ethyl-1,3-oxazolidin-2-one, (4R)-3-[4-(4-Bromophenyl)-1,3-thiazol-2-yl]-4-ethyl-1,3-oxazolidin-2-one, (4S)-3-[4-(4-Bromophenyl)-1,3-thiazol-2-yl]-4-ethyl-1,3-oxazolidin-2-one, 4-{2-[(4R)-4-Ethyl-2-oxo-1,3-oxazolidin-3-yl]-1,3-thiazol-4-yl}benzonitrile, 4-{2-[(4S)-4-Ethyl-2-oxo-1,3-oxazolidin-3-yl]-1,3-thiazol-4-yl}benzonitrile, 3-[4-(4-Bromophenyl)-1,3-thiazol-2-yl]4-propyl-1,3-oxazolidin-2-one, 4-[2-(2-Oxo-4-propyl-1,3-oxazolidin-3-yl)-1,3-thiazol-4-yl]benzonitrile, (4R)-3-[4-(4-Bromophenyl)-1,3-thiazol-2-yl]-4-propyl-1,3-oxazolidin-2-one, (4S)-3-[4-(4-Bromophenyl)-1,3-thiazol-2-yl]-4-propyl-1,3-oxazolidin-2-one, 4-{2-[(4S)-2-oxo-4-propyl-1,3-oxazolidin-3-yl]-1,3-thiazol-4-yl}benzonitrile, 4-{2-[(4R)-2-oxo-4-propyl-1,3-oxazolidin-3-yl]-1,3-thiazol-4-yl}benzonitrile, 3-[4-(4-Bromophenyl)-1,3-thiazol-2-yl]-4-isopropyl-1,3-oxazolidin-2-one, 4-[2-(4-Isopropyl-2-oxo-1,3-oxazolidin-3-yl)-1,3-thiazol-4-yl]benzonitrile, 3-[4-(4-Bromophenyl)-1,3-thiazol-2-yl]-4-butyl-1,3-oxazolidin-2-one, 4-[2-(4-Butyl-2-oxo-1,3-oxazolidin-3-yl)-1,3-thiazol-4-yl]benzonitrile, (4S)-3-[4-(4-Bromophenyl)-1,3-thiazol-2-yl]-4-isobutyl-1,3-oxazolidin-2-one, (4R)-3-[4-(4-Bromophenyl)-1,3-thiazol-2-yl]-4-phenyl-1,3-oxazolidin-2-one, 4-{2-[(4R)-2-Oxo-4-phenyl-1,3-oxazolidin-3-yl]-1,3- thiazol-4-yl}benzonitrile, 4-{2-[(4S)-2-Oxo-4-phenyl-1,3-oxazolidin-3-yl]-1,3-thiazol-4-yl}benzonitrile, (4R)-4-Benzyl-3-[4-(4-bromophenyl)-1,3-thiazol-2-yl]-1,3-oxazolidin-2-one, 4-{2-[(4R)-4-Benzyl-2-oxo-1,3-oxazolidin-3-yl]-1,3-thiazol-4-yl}benzonitrile, (4S)-4-[(benzyloxy)methyl]-3-[4-(4-bromophenyl)-1,3-thiazol-2-yl]-1,3-oxazolidin-2-one, (4R)-3-[4-(4-Bromophenyl)-1,3-thiazol-2-yl]-4-(hydroxymethyl)-1,3-oxazolidin-2-one, (4S)-3-[4-(4-Bromophenyl)-1,3-thiazol-2-yl]-4-(fluoromethyl)-1,3-oxazolidin-2-one, 4-{2-[(4S)-4-(Fluoromethyl)-2-oxo-1,3-oxazolidin-3-yl]-1,3-thiazol-4-yl}benzonitrile, (4S)-3-[4-(4-Bromophenyl)-1,3-thiazol-2-yl]-4-(chloromethyl)-1,3-oxazolidin-2-one, 3-[4-(4-Bromophenyl)-1,3-thiazol-2-yl]-4-(trifluoromethyl)-1,3-oxazolidin-2-one, 4-{2-[(4R)-2-oxo-4-(trifluoromethyl)-1,3-oxazolidin-3-yl]-1,3-thiazol-4-yl}benzonitrile, 4-{2-[(4S)-2-Oxo-4-(trifluoromethyl)-1,3-oxazolidin-3-yl]-1,3-thiazol-4-yl}benzonitrile, 3-[4-(4-Bromophenyl)-1,3-thiazol-2-yl]-4-(2,2,2-trifluoroethyl)-1,3-oxazolidin-2-one, 4-{2-[(4S)-2-Oxo-4-(2,2,2-trifluoroethyl)-1,3-oxazolidin-3-yl]-1,3-thiazol-4-yl}benzonitrile, 4-{2-[(4R)-2-Oxo-4-(2,2,2-trifluoroethyl)-1,3-oxazolidin-3-yl]-1,3-thiazol-4-yl}benzonitrile, Methyl (4S)-3-[4-(4-bromophenyl)-1,3-thiazol-2-yl]-2-oxo-1,3-oxazolidine-4-carboxylate, 3-[4-(4-Bromophenyl)-1,3-thiazol-2-yl]-4,4-dimethyl-1,3-oxazolidin-2-one, 4-[2-(4,4-Dimethyl-2-oxo-1,3-oxazolidin-3-yl)-1,3-thiazol-4-yl]benzonitrile, 3-[4-(3-Bromo-2-fluorophenyl)-1,3-thiazol-2-yl]-4,4-dimethyl-1,3-oxazolidin-2-one, 3-[4-(3-Bromophenyl)-1,3-thiazol-2-yl]-4,4-dimethyl-1,3-oxazolidin-2-one, 3-[4-(4-Chloro-3-fluorophenyl)-1,3-thiazol-2-yl]-4,4-dimethyl-1,3-oxazolidin-2-one, 4-[2-(4,4-Dimethyl-2-oxo-1,3-oxazolidin-3-yl)-1,3-thiazol-4-yl]-3-fluorobenzonitrile, 4,4-Dimethyl-3-[4-(4-nitrophenyl)-1,3-thiazol-2-yl]-1,3-oxazolidin-2-one, 4-[2-(4,4-Dimethyl-2-oxo-1,3-oxazolidin-3-yl)-1,3-thiazol-4-yl]-2-fluorobenzonitrile, 3-[2-(4,4-dimethyl-2-oxo-1,3-oxazolidin-3-yl)-1,3-thiazol-4-yl]benzonitrile, 4-[2-(4,4-Dimethyl-2-oxo-1,3-oxazolidin-3-yl)-1,3-thiazol-4-yl]-N'-hydroxybenzene carboximidamide, 4,4-Dimethyl-3-{4-[4-(trifluoromethyl)phenyl]-1,3-thiazol-2-yl}-1,3-oxazolidin-2-one, 4,4-Dimethyl-3-{4-[3-(trifluoromethyl)phenyl]-1,3-thiazol-2-yl}-1,3-oxazolidin-2-one, 4,4-Dimethyl-3-{4-[4-(trifluoromethoxy)phenyl]-1,3-thiazol-2-yl}-1,3-oxazolidin-2-one, 3-[4-(4-Methoxyphenyl)-1,3-thiazol-2-yl]-4,4-dimethyl-1,3-oxazolidin-2-one, 3-[4-(3-Methoxyphenyl)-1,3-thiazol-2-yl]-4,4-dimethyl-1,3-oxazolidin-2-one, 3-[4-(2-Methoxyphenyl)-1,3-thiazol-2-yl]-4,4-dimethyl-1,3-oxazolidin-2-one, 4,4-Dimethyl-3-[4-(2,4,6-trifluorophenyl)-1,3-thiazol-2-yl]-1,3-oxazolidin-2-one, 3-{4-[3-(Ethylsulfonyl)phenyl]-1,3-thiazol-2-yl}-4,4-dimethyl-1,3-oxazolidin-2-one, {4-[2-(4,4-Dimethyl-2-oxo-1,3-oxazolidin-3-yl)-1,3-thiazol-4-yl]phenyl}acetonitrile, 3-[4-(4-Acetylphenyl)-1,3-thiazol-2-yl]-4,4-dimethyl-1,3-oxazolidin-2-one, 3-[4-(3-Acetylphenyl)-1,3-thiazol-2-yl]-4,4-dimethyl-1,3-oxazolidin-2-one, 3-[4-(3,4-Dimethoxyphenyl)-1,3-thiazol-2-yl]-4,4-dimethyl-1,3-oxazolidin-2-one, 3-[4-(4-Chlorophenyl)-1,3-thiazol-2-yl]-4,4-dimethyl-1,3-oxazolidin-2-one, 3-[4-(4-Fluorophenyl)-1,3-thiazol-2-yl]-4,4-dimethyl-1,3-oxazolidin-2-one, 3-[4-(3,5-Dichlorophenyl)-1,3-thiazol-2-yl]-4,4-dimethyl-1,3-oxazolidin-2-one, 3-[4-(3-Chloro-4-fluorophenyl)-1,3-thiazol-2-yl]-4,4-dimethyl-1,3-oxazolidin-2-one, 3-[4-(2,4-Dichlorophenyl)-1,3-thiazol-2-yl]-4,4-dimethyl-1,3-oxazolidin-2-one, 3-[4-(3,4-Dichlorophenyl)-1,3-thiazol-2-yl]-4,4-dimethyl-1,3-oxazolidin-2-one, 4,4-Dimethyl-3-(4-phenyl-1,3-thiazol-2-yl)-1,3-oxazolidin-2-one, 4,4-Dimethyl-3-[4-(4-methylphenyl)-1,3-thiazol-2-yl]-1,3-oxazolidin-2-one, 4,4-Dimethyl-3-[4-(2-nitrophenyl)-1,3-thiazol-2-yl]-1,3-oxazolidin-2-one, 4,4-Dimethyl-3-[4-(3-nitrophenyl)-1,3-thiazol-2-yl]-1,3-oxazolidin-2-one, 3-{4-[4-(Benzyloxy)phenyl]-1,3-thiazol-2-yl}-4,4-dimethyl-1,3-oxazolidin-2-one, 3-[4-(4-Fluoro-3-methylphenyl)-1,3-thiazol-2-yl]-4,4-dimethyl-1,3-oxazolidin-2-one, 4,4-Dimethyl-3-[4-(4-phenoxyphenyl)-1,3-thiazol-2-yl]-1,3-oxazolidin-2-one, 3-(4-Biphenyl-4-yl-1,3-thiazol-2-yl)-4,4-dimethyl-1,3-oxazolidin-2-one, Methyl 4-[2-(4,4-dimethyl-2-oxo-1,3-oxazolidin-3-yl)-1,3-thiazol-4-yl]benzoate, 3-[4-(4-Bromophenyl)-1,3-thiazol-2-yl]-5-methyl-1,3-oxazolidin-2-one, 4-[2-(5-Methyl-2-oxo-1,3-oxazolidin-3-yl)-1,3-thiazol-4-yl]benzonitrile, 3-[4-(4-Bromophenyl)-1,3-thiazol-2-yl]-5-ethyl-1,3-oxazolidin-2-one, 4-[2-(5-Ethyl-2-oxo-1,3-oxazolidin-3-yl)-1,3-thiazol-4-yl]benzonitrile, 4-[2-(4,4,5-Trimethyl-2-oxo-1,3-oxazolidin-3-yl)-1,3-thiazol-4-yl]benzonitrile, 4-[2-(2-Oxo-1,3-benzoxazol-3(2H)-yl)-1,3-thiazol-4-yl]benzonitrile, 3-[3-(4-Bromophenyl)-1,2,4-thiadiazol-5-yl]-4,4-dimethyl-1,3-oxazolidin-2-one, 4-[5-(4,4-dimethyl-2-oxo-1,3-oxazolidin-3-yl)-1,2,4-thiadiazol-3-yl]benzonitrile, 4-[5-(2-Oxo-1,3-oxazolidin-3-yl)-3-thienyl]benzonitrile, 4-[2-(4,4-dimethyl-2-oxo-1,3-oxazolidin-3-yl)-1,3-oxazol-4-yl]benzonitrile, 4-[4-(4-Bromophenyl)-1,3-thiazol-2-yl]-6-oxa-4-azaspiro[2.4]heptane-5-one, 4-[2-(5-oxo-6-oxa-4-azaspiro[2.4]hept-4-yl)-1,3-thiazol-4-yl]benzonitrile, 5-[4-(4-Bromophenyl)-1,3-thiazol-2-yl]-7-oxa-5-azaspiro[3.4]octan-6-one, 4-[2-(6-Oxo-7-oxa-5-azaspiro[3.4]oct-5-yl)-1,3-thiazol-4-yl]benzonitrile, 1-[4-(4-Bromophenyl)-1,3-thiazol-2-yl]-3-oxa-1-azaspiro[4.4]nonan-2-one, 4-[2-(2-Oxo-3-oxa-1-azaspiro[4.4]non-1-yl)-1,3-thiazol-4-yl]benzonitrile, 4-[2-(4,4-Diethyl-2-oxo-1,3-oxazolidin-3-yl)-1,3-thiazol-4-yl]benzonitrile, 4-[2-(4,4-Diethyl-2-oxo-1,3-oxazolidin-3-yl)-5-fluoro-1,3-thiazol-4-yl]benzonitrile, 4-[5-Fluoro-2-(5-oxo-6-oxa-4-azaspiro[2.4]hept-4-yl)-1,3-thiazol-4-yl]benzonitrile, (4S)-3-[4-(4-Bromophenyl)-5-fluoro-1,3-thiazol-2-yl]-4-ethyl-1,3-oxazolidin-2-one, (4S)-3-[4-(4-Bromophenyl)-5-chloro-1,3-thiazol-2-yl]-4-ethyl-1,3-oxazolidin-2-one, 4-{2-[(4S)-4-Ethyl-2-oxo-1,3-oxazolidin-3-yl]-5-fluoro-1,3-thiazol-4-yl}benzonitrile, 4-{5-Chloro-2-[(4S)-4-ethyl-2-oxo-1,3-oxazolidin-3-yl]-1,3-thiazol-4-yl}benzonitrile, 4-(4-Cyanophenyl)-2-[(4S)-4-ethyl-2-oxo-1,3-oxazolidin-3-yl]-1,3-thiazole-5-carbonitrile, 3-[4-(4-Bromophenyl)-5-methyl-1,3-thiazol-2-yl]-4,4-dimethyl-1,3-oxazolidin-2-one, 4-[2-(4,4-dimethyl-2-oxo-1,3-oxazolidin-3-yl)-5-fluoro-1,3-thiazol-4-yl]benzonitrile, 4-[2-(4,4-Dimethyl-2-oxo-1,3-oxazolidin-3-yl)-5-methyl-1,3-thiazol-4-yl]benzonitrile, 4-[5-Chloro-2-(4,4-dimethyl-2-oxo-1,3-oxazolidin-3-yl)-1,3-thiazol-4-yl]benzonitrile, Methyl 4-[5-chloro-2-(4,4-dimethyl-2-oxo-1,3-oxazolidin-3-yl)-1,3-thiazol-4-yl]benzoate, 4-Bromo-5-[2-(4,4-dimethyl-2-oxo-1,3-oxazolidin-3-yl)-1,3-thiazol-4-yl]thiophene-2-carbonitrile, 4-[2-(4,4-Dimethyl-2-oxo-1,3-oxazolidin-3-yl)-1,3-thiazol-4-yl]thiophene-2-carbonitrile, 5-[2-(4,4-dimethyl-2-oxo-1,3-oxazolidin-3-yl)-1,3-thiazol-4-yl]thiophene-2-carbonitrile, 4-[2-(4,4-Dimethyl-2-oxo-1,3-oxazolidin-3-yl)-1,3-thiazol-4-yl]-1-methyl-1H-pyrrole-2-carbonitrile, 5-[2-(4,4-Dimethyl-2-oxo-1,3-oxazolidin-3-yl)-1,3-thiazol-4-yl]-1-methyl-1H-pyrrole-3-carbonitrile, 3-[4-(3-Furyl)-1,3-thiazol-2-yl]-4,4-dimethyl-1,3-oxazolidin-2-one, 3-[4-(1H-Indol-5-yl)-1,3-thiazol-2-yl]-4,4-dimethyl-1,3-oxazolidin-2-one, 4,4-Dimethyl-3-[4-(2-naphthyl)-1,3-thiazol-2-yl]-1,3-oxazolidin-2-one, and 4-[2-(4,4-Dimethyl-2-thioxo-1,3-oxazolidin-3-yl)-1,3-thiazol-4-yl]benzonitrile, or a pharmaceutically acceptable salt, tautomer, metabolite or prodrug thereof.

In another embodiment, the compound is 4-[2-(4,4-Dimethyl-2-oxo-1,3-oxazolidin-3-yl)-1,3-thiazol-4-yl]benzonitrile, or a pharmaceutically acceptable salt, tautomer, metabolite or prodrug thereof.

The compounds as described can contain one or more asymmetric centers and can thus give rise to optical isomers and diastereomers. The compounds can include optical isomers and diastereomers; racemic and resolved enantiomerically pure R and S stereoisomers; other mixtures of the R and S stereoisomers; and pharmaceutically acceptable salts thereof.

The term "alkyl" is used herein to refer to both straight- and branched-chain saturated aliphatic hydrocarbon groups. In one embodiment, an alkyl group has 1 to 8 carbon atoms (i.e., $C_1$, $C_2$, $C_3$, $C_4$, $C_5$ $C_6$, $C_7$, or $C_8$). In another embodiment, an alkyl group has 1 to 6 carbon atoms (i.e., $C_1$, $C_2$, $C_3$, $C_4$, $C_5$ or $C_6$). In a further embodiment, an alkyl group has 1 to 4 carbon atoms (i.e., $C_1$, $C_2$, $C_3$, or $C_4$). Examples include methyl, ethyl, n-propyl, i-propyl, n-butyl, s-butyl, t-butyl, pentyl and hexyl, among others.

The term "cycloalkyl" is used herein to refer to cyclic, saturated aliphatic hydrocarbon groups. In one embodiment, a cycloalkyl group has 3 to 8 carbon atoms (i.e., $C_3$, $C_4$, $C_5$, $C_6$, $C_7$, or $C_8$). In another embodiment, a cycloalkyl group has 3 to 6 carbon atoms (i.e., $C_3$, $C_4$, $C_5$ or $C_6$). Examples include cyclopropyl, cyclobutyl, cyclopentyl and cyclohexyl, among others.

The term "alkenyl" is used herein to refer to both straight- and branched-chain alkyl groups having one or more carbon-carbon double bonds. In one embodiment, an alkenyl group contains 3 to 8 carbon atoms (i.e., $C_3$, $C_4$, $C_5$, $C_6$, $C_7$, or $C_8$). In another embodiment, an alkenyl group has 1 or 2 carbon-carbon double bonds and 3 to 6 carbon atoms (i.e., $C_3$, $C_4$, $C_5$ or $C_6$). Examples include propenyl, among others.

The term "alkynyl" is used herein to refer to both straight- and branched-chain alkyl groups having one or more carbon-carbon triple bonds. In one embodiment, an alkynyl group has 3 to 8 carbon atoms (i.e., $C_3$, $C_4$, $C_5$, $C_6$, $C_7$, or $C_8$). In another embodiment, an alkynyl group contains 1 or 2 carbon-carbon triple bonds and 3 to 6 carbon atoms (i.e., $C_3$, $C_4$, $C_5$, or $C_6$). Examples include propynyl, among others.

The terms "substituted alkyl", "substituted alkenyl", "substituted alkynyl", and "substituted cycloalkyl" refer to alkyl, alkenyl, alkynyl, and cycloalkyl groups, respectively, having one or more substituents e.g. 1 to 3 substituents which may be the same or different, selected from hydrogen, halogen, CN, OH, $NO_2$, amino, aryl, heterocyclyl, aryl, alkoxy, aryloxy, alkylcarbonyl, alkylcarboxy, and arylthio. One suitable group of substituents is hydrogen, halogen, CN, OH, $NO_2$, amino, phenyl, $C_1$-$C_4$ alkoxy, phenoxy, $C_1$-$C_4$ alkylcarbonyl, $C_1$-$C_4$ alkylcarboxy and phenylthio.

The term "arylthio" as used herein refers to the S(aryl) group, where the point of attachment is through the sulfur-atom and the aryl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio. The term "alkoxy" as used herein refers to the O(alkyl) group, where the point of attachment is through the oxygen-atom and the alkyl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio. The term "aryloxy" as used herein refers to the O(aryl) group, where the point of attachment is through the oxygen-atom and the aryl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio.

The term "alkylcarbonyl" as used herein refers to the C(O)(alkyl) group, where the point of attachment is through the carbon-atom of the carbonyl moiety and the alkyl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio.

The term "alkylcarboxy" as used herein refers to the C(O)O(alkyl) group, where the point of attachment is through the carbon-atom of the carboxy moiety and the alkyl group can be substituted, e.g., by 1 to 4 substituents, the same or different, selected from among hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio.

The term "alkylamino" as used herein refers to both secondary and tertiary amines where the point of attachment is through the nitrogen-atom and the alkyl groups can be substituted, e.g., by 1 to 4 substituents, the same or different, selected from hydrogen, halogen, CN, OH, $NO_2$, amino, phenyl, $C_1$-$C_4$ alkyloxy, phenoxy, $C_1$-$C_4$ alkylcarbonyl, $C_1$-$C_4$ alkylcarboxyl and phenylthio. The alkyl groups can be the same or different.

The term "halogen" as used herein refers to Cl, Br, F, or I.

The term "aryl" as used herein refers to an aromatic, carbocyclic system, e.g., of 6 to 14 carbon atoms, which can include a single ring or multiple aromatic rings fused or linked together where at least one part of the fused or linked rings forms the conjugated aromatic system. The aryl groups include, but are not limited to, phenyl, naphthyl, biphenyl, anthryl, tetrahydronaphthyl, phenanthryl, indene, benzonaphthyl, and fluorenyl.

The term "substituted aryl" refers to an aryl group which is substituted with one or more substituents selected from halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, aryloxy, alkoxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl. Desirably, a substituted aryl group is substituted with 1 to 4 substituents which may be the same or different.

The term "heterocycle" or "heterocyclic" as used herein can be used interchangeably to refer to a stable, saturated or partially unsaturated 3- to 9-membered monocyclic or multicyclic heterocyclic ring. The heterocyclic ring has in its backbone carbon atoms and one or more heteroatoms including nitrogen, oxygen, and sulfur atoms. In one embodiment, the heterocyclic ring has 1 tot 4 heteroatoms in the backbone of the ring. When the heterocyclic ring contains nitrogen or sulfur atoms in the backbone of the ring, the nitrogen or sulfur atoms can be oxidized. The term "heterocycle" or "heterocyclic" also refers to multicyclic rings in which a heterocyclic ring is fused to an aryl ring of 6 to 14 carbon atoms. The heterocyclic ring can be attached to the aryl ring through a heteroatom or carbon atom provided the resultant heterocyclic ring structure is chemically stable. In one embodiment, the heterocyclic ring includes multicyclic systems having 1 to 5 rings. Suitable heterocyclic rings include those having 6 to 12, preferably 6 to 10 ring members containing 1 to 3 heteroatoms selected from N, O and S. Suitable heteroaryl rings include those having 5 to 12 preferably 5 to 10 ring members containing 1 to 3 heteroatoms selected from N, O and S.

A variety of heterocyclic groups are known in the art and include, without limitation, oxygen-containing rings, nitrogen-containing rings, sulfur-containing rings, mixed heteroatom-containing rings, fused heteroatom containing rings, and combinations thereof. Examples of heterocyclic groups include, without limitation, tetrahydrofuranyl, piperidinyl, 2-oxopiperidinyl, pyrrolidinyl, morpholinyl, thiamorpholinyl, thiamorpholinyl sulfoxide, pyranyl, pyronyl, dioxinyl, piperazinyl, dithiolyl, oxathiolyl, dioxazolyl, oxathiazolyl, oxazinyl, oxathiazinyl, benzopyranyl, benzoxazinyl and xanthenyl.

The term "heteroaryl" as used herein refers to a stable, aromatic 5- to 14-membered monocyclic or multicyclic heteroatom-containing ring. The heteroaryl ring has in its backbone carbon atoms and one or more heteroatoms including nitrogen, oxygen, and sulfur atoms. In one embodiment, the heteroaryl ring contains 1 to 4 heteroatoms in the backbone of the ring which may suitably be selected from O, S and N. When the heteroaryl ring contains nitrogen or sulfur atoms in the backbone of the ring, the nitrogen or sulfur atoms can be oxidized. The term "heteroaryl" also refers to multicyclic rings in which a heteroaryl ring is fused to an aryl ring. The heteroaryl ring can be attached to the aryl ring through a heteroatom or carbon atom provided the resultant heterocyclic ring structure is chemically stable. In one embodiment, the heteroaryl ring includes multicyclic systems having 1 to 5 rings.

A variety of heteroaryl groups are known in the art and include, without limitation, oxygen-containing rings, nitrogen-containing rings, sulfur-containing rings, mixed heteroatom-containing rings, fused heteroatom containing rings, and combinations thereof. Examples of heteroaryl groups include, without limitation, furyl, pyrrolyl, pyrazolyl, imidazolyl, triazolyl, pyridyl, pyridazinyl, pyrimidinyl, pyrazinyl, triazinyl, azepinyl, thienyl, dithiolyl, oxathiolyl, oxazolyl, thiazolyl, oxadiazolyl, oxatriazolyl, oxepinyl, thiepinyl, diazepinyl, benzofuranyl, thionapthene, indolyl, benzazolyl, purindinyl, pyranopyrrolyl, isoindazolyl, indoxazinyl, benzoxazolyl, quinolinyl, isoquinolinyl, benzodiazonyl, napthylridinyl, benzothienyl, pyridopyridinyl, acridinyl, carbazolyl, and purinyl rings.

The term "substituted heterocycle" and "substituted heteroaryl" as used herein refers to a heterocycle or heteroaryl group having one or more substituents, the same or different selected from halogen, CN, OH, $NO_2$, amino, alkyl, cycloalkyl, alkenyl, alkynyl, $C_1$ to $C_3$ perfluoroalkyl, $C_1$ to $C_3$ perfluoroalkoxy, aryloxy, alkoxy including —O—($C_1$ to $C_{10}$ alkyl) or —O—($C_1$ to $C_{10}$ substituted alkyl), alkylcarbonyl including —CO—($C_1$ to $C_{10}$ alkyl) or —CO—($C_1$ to $C_{10}$ substituted alkyl), alkylcarboxy including —COO—($C_1$ to $C_{10}$ alkyl) or —COO—($C_1$ to $C_{10}$ substituted alkyl), —C($NH_2$)=N—OH, —$SO_2$—($C_1$ to $C_{10}$ alkyl), —$SO_2$—($C_1$ to $C_{10}$ substituted alkyl), —O—$CH_2$-aryl, alkylamino, arylthio, aryl, or heteroaryl. A substituted heterocycle or heteroaryl group may have 1, 2, 3, or 4 substituents.

The compounds may encompass tautomeric forms of the structures provided herein characterized by the bioactivity of the drawn structures. Further, the compounds may also be used in the form of salts derived from pharmaceutically or physiologically acceptable acids, bases, alkali metals and alkaline earth metals.

Pharmaceutically acceptable salts can be formed from organic and inorganic acids including, e.g., acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids. Salts may also be formed from inorganic bases, desirably alkali metal salts including, e.g., sodium, lithium, or potassium, and organic bases, such as ammonium salts, mono-, di-, and trimethylammonium, mono-, di- and triethylammonium, mono-, di- and tripropylammonium (iso and normal), ethyldimethylammonium, benzyldimethylammonium, cyclohexylammonium, benzylammonium, dibenzylammonium, piperidinium, morpholinium, pyrrolidinium, piperazinium, 1-methylpiperidinium, 4-ethylmorpholinium, 1-isopropylpyrrolidinium, 1,4-dimethylpiperazinium, 1-n-butyl piperidinium, 2-methylpiperidinium, 1-ethyl-2-methylpiperidinium, mono-, di- and triethanolammonium, ethyl diethanolammonium, n-butylmonoethanolammonium, tris(hydroxymethyl)methylammonium, phenylmonoethanolammonium, and the like.

Physiologically acceptable alkali salts and alkaline earth metal salts can include, without limitation, sodium, potassium, calcium and magnesium salts in the form of esters, and carbamates.

These salts, as well as other compounds, can be in the form of esters, carbamates and other conventional "pro-drug" forms, which, when administered in such form, convert to the active moiety in vivo. In one embodiment, the prodrugs are esters. In another embodiment, the prodrugs are carbamates. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The compounds discussed herein also encompass "metabolites" which are unique products formed by processing the compounds by the cell or subject. Desirably, metabolites are formed in vivo.

II. Methods of Preparing the Compounds

The compounds described herein are readily prepared by one of skill in the art according to the following schemes using commercially available starting materials or starting materials which can be prepared using literature procedures. These schemes show the preparation of representative compounds. Variations on these methods, or other methods known in the art, can be readily performed by one of skill in the art given the information provided herein.

As shown in Scheme 1, an appropriately substituted aryl or heteroaryl bromomethylketone 1 is reacted with potassium thiocyanate in a solvent such as ethanol to give the thiocyanate 2. Reaction of 2 with 30% HBr in acetic acid provides the 2-bromo-4-aryl or heteroaryl thiazole 3. For compounds whereby W is oxygen, 3 is heated with amine 4 to provide 5. Cyclization of 5 using a variety of activated reagents, including triphosgene and 1,1'-carbonyldiimidazole, gives 7. Additional activated reagents can be used to prepare 7 and are provided in the examples set forth below.

For compounds whereby W is $NR_{10}$, alcohol 8 is oxidized to give 9. Reaction of 9 with an amine, such as $NH_2R_{10}$, followed by a reduction provides 10. Cyclization of 10, using the cyclization described above for 7, provides compound 11.

For compounds whereby W is $CR_{11}R_{12}$ and V is O, carbonyl 9 is reacted with a phosphonate ester, such as $(CH_3O)_2P(O)CH_2CO_2CH_3$, using a base, such as sodium hydride, in a suitable solvent, such as tetrahydrofuran (THF), to give unsaturated ester 12. Reduction of 12 with a catalyst, such as 10% palladium on carbon in a suitable solvent, provides saturated ester 13. Cyclization of 13 under basic conditions, including using a base such as sodium bis(trimethylsilyl)amide in a solvent such as THF, provides saturated amide 14. Alternatively, 12 can be treated with a base such as sodium methoxide in a solvent such as THF to give unsaturated amide 14.

Scheme 1

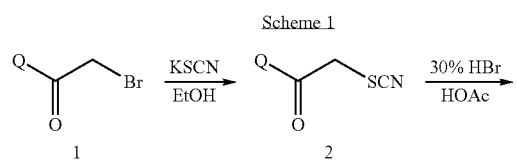

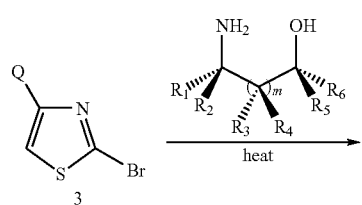

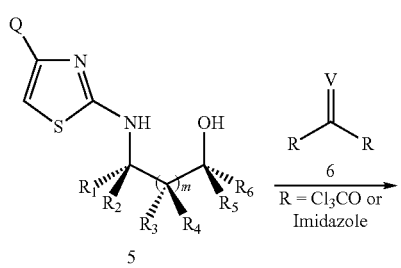

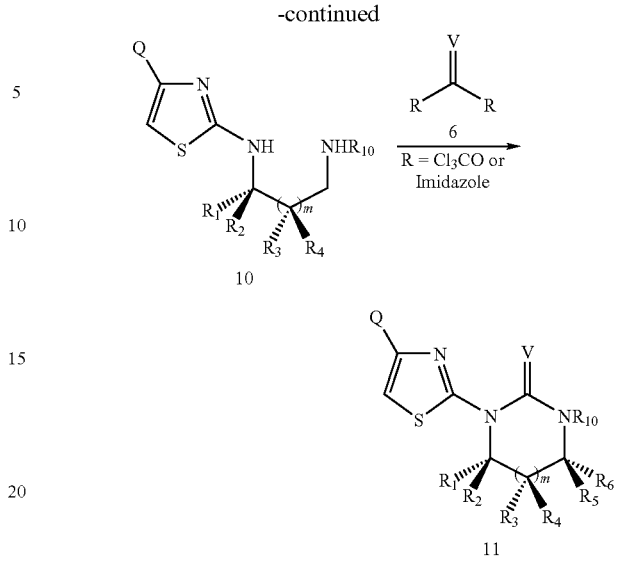

For W = NR$_{10}$

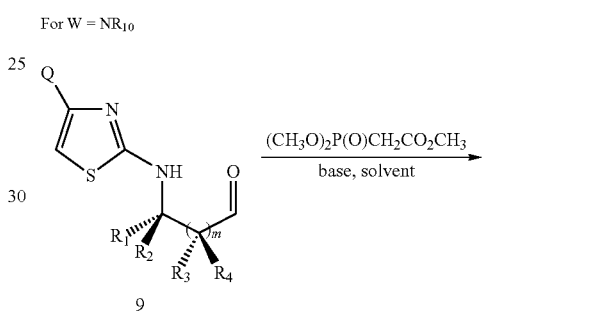

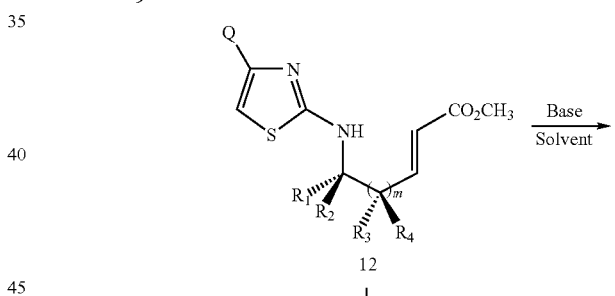

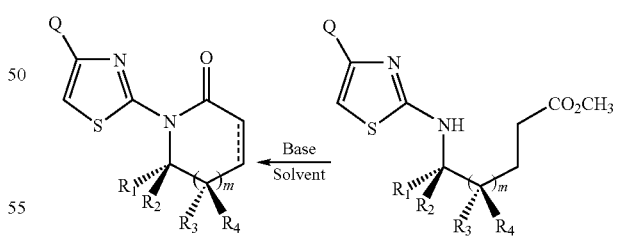

For W = CR$_{11}$R$_{12}$ and V = O

For W = O

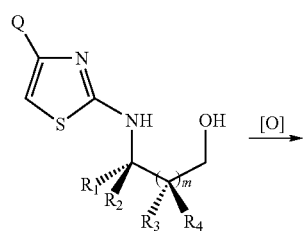

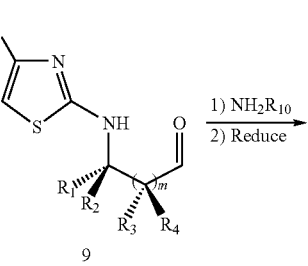

An alternate route to the thiazole derivatives is shown in Scheme 2. Reaction of amine 4 with benzoyl isothiocyanate 15 provides benzoyl thiourea 16, which is then hydrolyzed to thiourea 17. Reaction of 17 with the appropriately substituted aryl or heteroaryl bromomethylketone 1 provides thiazole 5, which is cyclized to 7 as previously described in Scheme 1.

Scheme 2

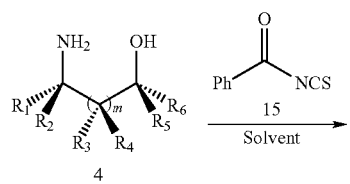

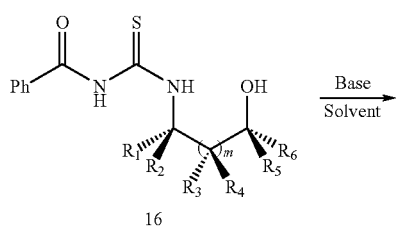

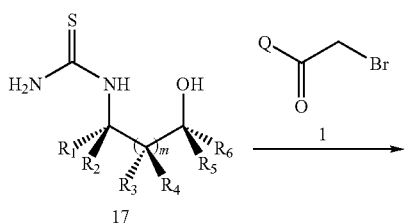

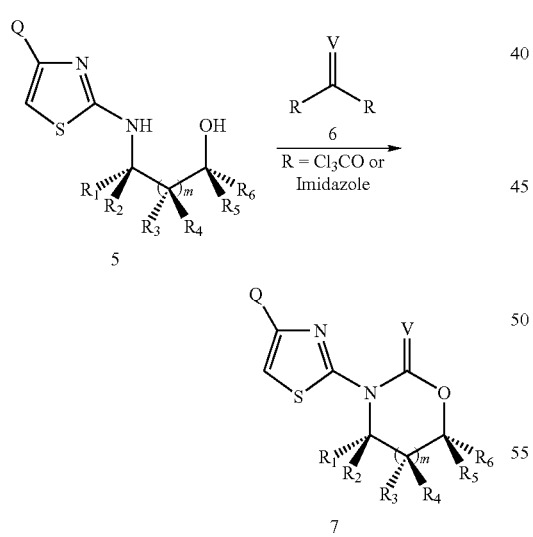

A third route to the thiazole derivatives is shown in Scheme 3. Reaction of amino ester salt 18 with thiocyanate 2 using a base, such as triethylamine, and an appropriate solvent, such as ethanol, gives aminothiazole 19. Reduction of 19 with a reducing agent, such as lithium aluminum hydride, and subsequent cyclization as previously described in Scheme 1 provides thiazole 20.

Scheme 3

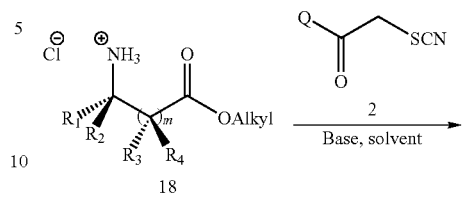

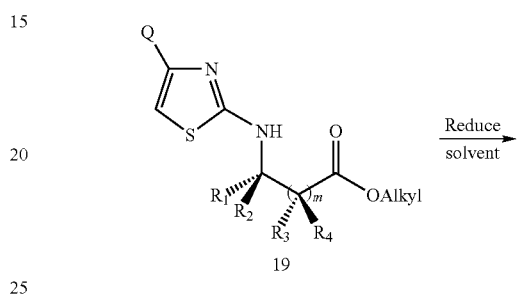

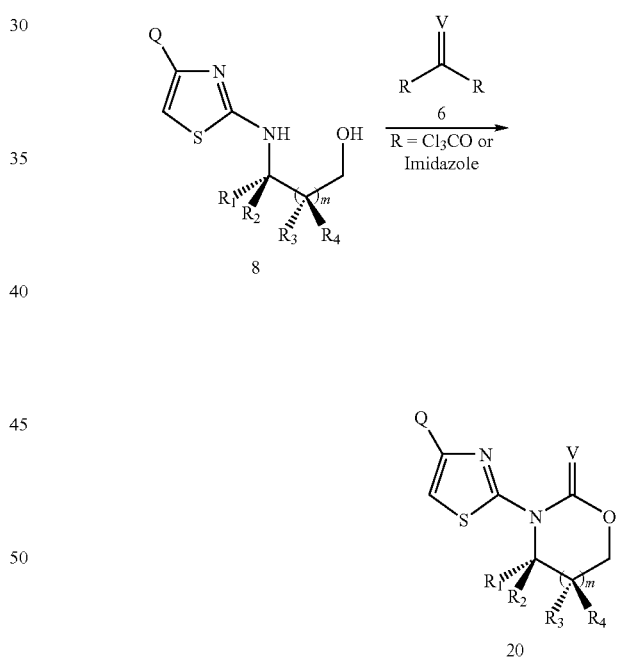

The introduction of either fluorine or chlorine at the five position of the thiazole ring is shown in Scheme 4. In the case of fluorine, reaction of cyclized thiazole 22 with an electrophilic fluorinating agent, such as the Selectfluor® reagent, directly provides fluoro derivative 25. However, in the case of the chlorine, aminothiazole 21 is first reacted with a positive source of chlorine, such as N-chlorosuccinimide, to give the five substituted thiazole 23, which is cyclized as previously described in Scheme 1 to give 24.

Scheme 4

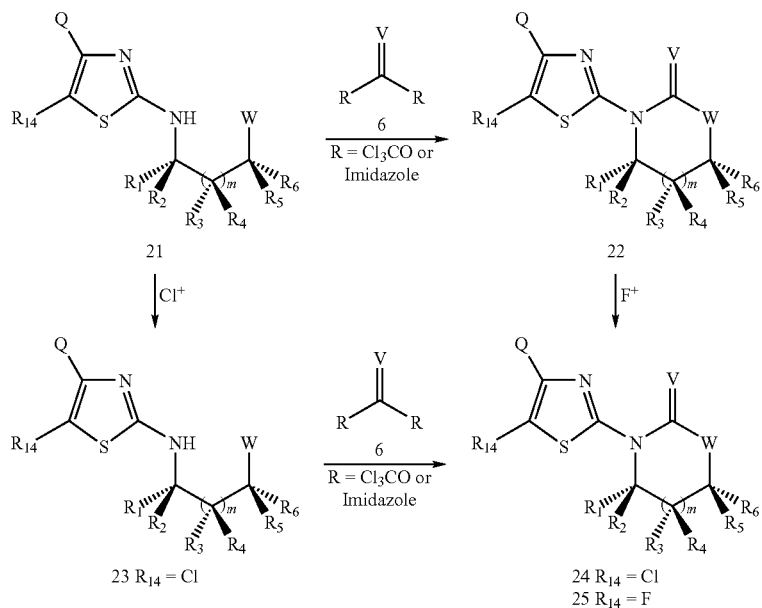

The preparation of derivatives having a trifluoromethyl group in the four position of the oxazolidinone ring is shown in Scheme 5. Reaction of 26 with the ethyl trifluoropyruvate 27 in the presence titanium (IV) chloride in a suitable solvent, such as methylene chloride, followed by reduction with a reducing agent, such as sodium cyanoborohydride, provides trifluoromethyl methyl ester 28. Further reduction of ester 28 to the alcohol 29, using, e.g, lithium aluminum hydride, followed by cyclization as previously described in Scheme 1, provides trifluoromethyl derivative 30.

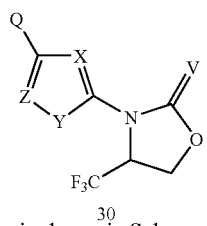

The preparation of oxazole derivatives is shown in Scheme 6. Heating an appropriately substituted aryl bromomethylketone 1 with an amide, such as formamide, provides oxazole 32. Reaction of 32 with a base, such as sodium bis(trimethylsilyl)amide in THF, followed by the addition of iodine, provides 2-iodooxazole 33. Reaction of 34 with sodium hydride, followed by the addition of 33, and heating at 170° C. for 2 hours gives oxazole 35.

Scheme 5

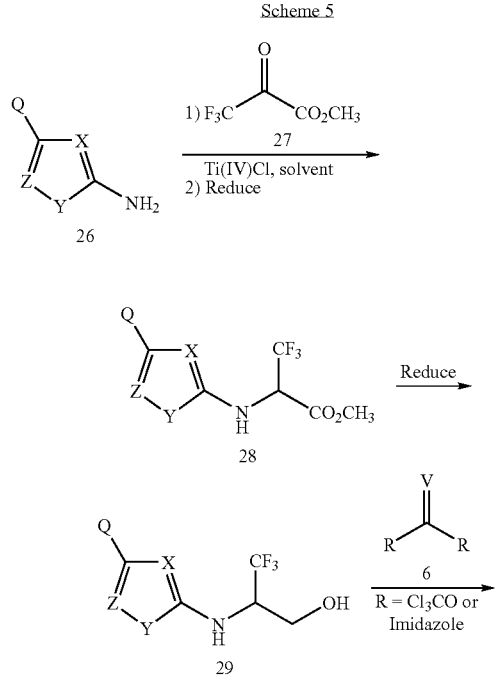

Scheme 6

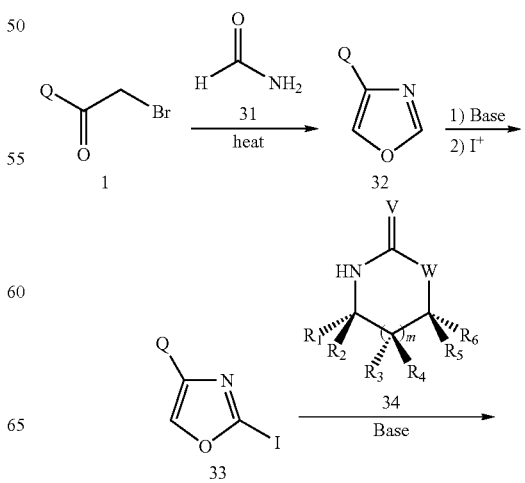

-continued

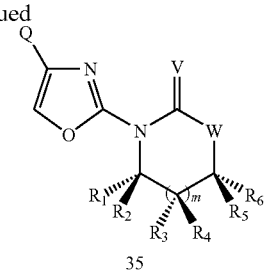
35

The preparation of thiadiazole derivatives is shown in Scheme 7. Reaction of an appropriately substituted amidine 36 with trichloromethanesulfenyl chloride in the presence of a base, such as triethylamine, and a suitable solvent, such as methylene chloride, gives 5-chloro substituted thiadiazole 37. Heating 37 with amine 38 at elevated temperatures of about 125° C. gives thiadiazole 39. The thiadiazole 39 is then cyclized to 40 as previously described in Scheme 1.

Scheme 7

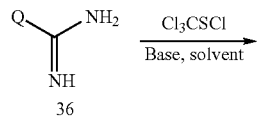
36

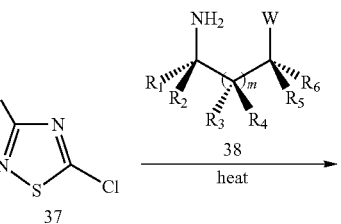
37

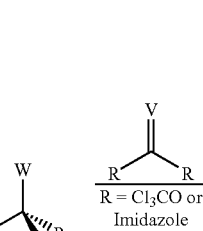
39

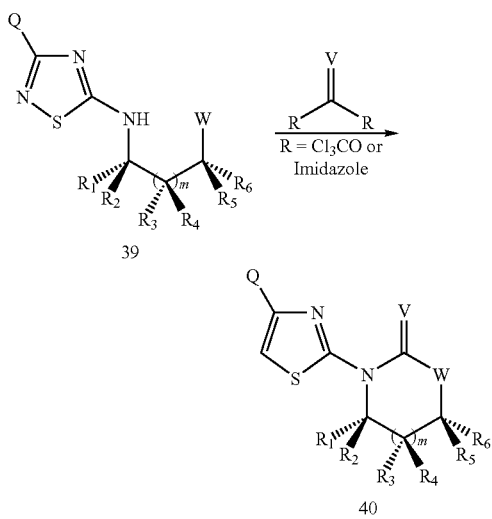
40

An alternative method for introducing the aryl group is shown in Scheme 8. Reaction of triflate 41 with the appropriately substituted arylboronic acid 42 in the presence of a catalyst, such as tetrakis(triphenylphosphine)palladium (0), in a solvent containing a base, gives 43.

Scheme 8

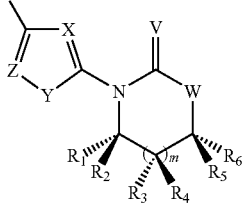
41

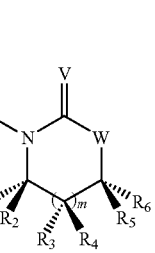
43

The preparation of thiophene derivatives is described in Scheme 9. Specifically, 2,4-dibromothiophene 44 is reacted with amine 34 in the presence of copper (I) iodide, in a solvent, such as dioxane, containing an amine base and cesium carbonate, at elevated temperature of about 110° C. provides the 2-substituted-4-bromothiophene 45. Reaction of 45 with the appropriately substituted arylboronic acid 42, in a similar manner as described in Scheme 8, gives thiophene 46.

Scheme 9

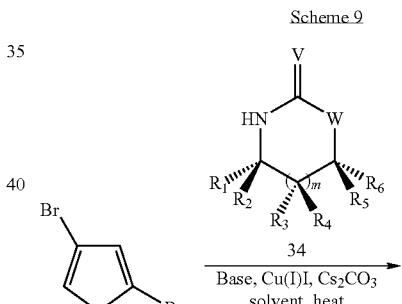
44

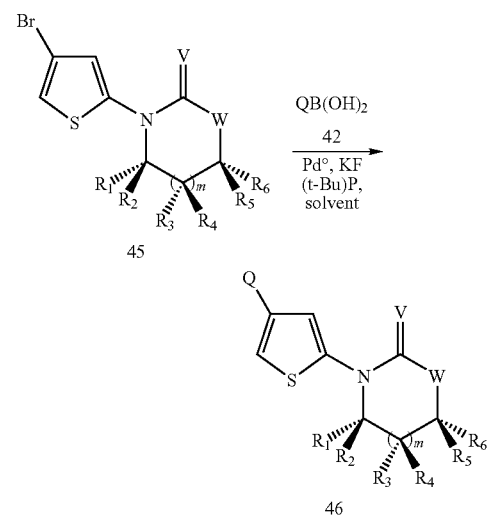
45

46

III. Methods of Using the Compounds

Also provided are pharmaceutical compositions containing one or more compounds described herein and a pharmaceutically acceptable carrier or excipient. In one embodiment, the methods of treatment include administering to a mammal a pharmaceutically effective amount of one or more compounds as described herein as progesterone receptor modulators.

The compounds may be combined with one or more pharmaceutically acceptable carriers or excipients, e.g., solvents, diluents and the like. Suitably, the compounds are formulated for delivery to a subject by any suitable route including, e.g., transdermal, mucosal (intranasal, buccal, vaginal), oral, parenteral, among others. A variety of suitable delivery devices can be utilized for these delivery routes and include, without limitation, tablets, caplets, capsules, gel tabs, dispersible powders, granules, suspensions, injectable solutions, transdermal patches, topical creams or gels, and vaginal rings, among others.

In preparing the compositions described herein, the compounds may be combined with one or more of a solid carrier, liquid carrier, adjuvant, suspending agent, syrup, and elixir, among others, the selection of which is dependent on the nature of the active ingredient and the particular form of administration desired.

Solid carriers include, without limitation, starch, lactose, dicalcium phosphate, microcrystalline cellulose, sucrose and kaolin.

Liquid carriers include, without limitation, sterile water, dimethylsulfoxide (DMSO), polyethylene glycols, non-ionic surfactants and edible oils such as corn, peanut and sesame oils.

Adjuvants can include, without limitation, flavoring agents, coloring agents, preserving agents, and antioxidants, e.g., vitamin E, ascorbic acid, butylatedhydroxytoluene (BHT) and butylatedhydroxyanisole (BHA).

In one embodiment, the compound may be combined with a suspending agent, including about 0.05 to about 5% of suspending agent.

In another embodiment, the compound may be combined with a syrup containing, e.g., about 10 to about 50% of sugar.

In a further embodiment, the compound may be combined with an elixir containing, e.g., about 20 to about 50% ethanol, and the like.

When formulated for oral delivery, the compounds can be in the form of a tablet, capsule, caplet, gel tab, dispersible powder, granule, or suspension. One particularly desirable pharmaceutical composition, from the standpoint of ease of preparation and administration, are solid compositions, particularly tablets and hard-filled or liquid-filled capsules.

The compounds may also be administered parenterally or intraperitoneally as solutions, suspensions, dispersions, or the like. Such pharmaceutical preparations may contain, e.g., about 25 to about 90% of the compound in combination with the carrier. Desirably, the pharmaceutical preparation contains about 5% and 60% by weight of the compound. In one embodiment, the compounds are administered in solutions or suspensions, whereby the compounds are present as free bases or pharmacologically acceptable salts and are prepared in water suitably mixed with a surfactant such as hydroxypropylcellulose. In another embodiment, the solutions or suspensions containing the compound may contain about 0.05 to about 5% of a suspending agent in an isotonic medium. In a further embodiment, the compounds are administered in dispersions, which may be prepared in glycerol, polyethylene glycols and mixtures thereof in oils.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringe ability exits. It must be stable under conditions of manufacture and storage and must be preserved against the contaminating action of microorganisms such as bacterial and fungi. The carrier utilized in the injectable form may be a solvent or dispersion medium containing, e.g., water, ethanol (e.g., glycerol, propylene glycol and liquid polyethylene glycol), suitable mixtures thereof, and vegetable oil.

The compounds may also be administered via a vaginal ring. Suitably, use of the vaginal ring is timed to cycle to which the compound is being administered, including a 28-day cycle. However, the vaginal ring can be inserted for longer or shorter periods of time. See, U.S. Pat. Nos. 5,972, 372; 6,126,958; and 6,125,850, which are hereby incorporated by reference, for formulations of the vaginal ring that can be used.

The compounds can also be delivered via a transdermal patch. Suitably, use of the patch is timed to the length of the cycle, including a 28 day cycle. However, the patch can remain in place for longer or shorter periods of time.

The compounds may be utilized in methods of contraception, hormone replacement therapy, and the treatment and/or prevention of benign and malignant neoplastic disease; cycle-related symptoms; fibroids, including uterine fibroids; leiomyomata; endometriosis; benign prostatic hypertrophy; carcinomas and adenocarcinomas of the endometrium, ovary, breast, colon, prostate, pituitary, meningioma and other hormone-dependent tumors; dysmenorrhea; dysfunctional uterine bleeding; symptoms of premenstrual syndrome and premenstrual dysphoric disorder; and for inducing amenorrhea. Additional uses of the present progesterone receptor modulators include the synchronization of estrus in livestock. In one embodiment, the neoplastic disease is hormone-dependent.

The term "cycle-related symptoms" refers to psychological symptoms (e.g., mood change, irritability, anxiety, lack of concentration, or decrease in sexual desire) and physical symptoms (e.g., dysmenorrhea, breast tenderness, bloating, fatigue, or food cravings) associated with a woman's menstrual cycle. Cycle-related symptoms include, but are not limited to, dysmenorrhea and moderate to severe cycle-related symptoms.

When utilized for these purposes, the compounds can be administered in combination with other agents, as well as in combination with each other. Such agents include, without limitation, progestins, antiprogestins, estrogens, antiestrogens, selective estrogen receptor modulators (SERMS), among others. Progestins can include, without limitation, tanaproget, levonorgestrel, norgestrel, desogestrel, 3-ketodesogestrel, norethindrone, gestodene, norethindrone acetate, norgestimate, osaterone, cyproterone acetate, trimegestone, dienogest, drospirenone, nomegestrol, (17-deacetyl)norgestimate. Estrogens can include, without limitation, ethinyl estradiol. The compounds described herein can be combined with one or more of these agents, delivered concurrently therewith one or more of these agents, delivered prior to one or more of these agents, or delivered subsequent to one or more of these agents.

A patient or subject being treated is a mammalian subject and typically a female. Desirably, the subject is a human. However, as used herein, a female can include non-human mammals, e.g., cattle or livestock, horses, pigs, domestic animals, etc.

The effective dosage of the compound may vary depending on the particular compound employed, the mode of administration and the severity of the condition being treated. However, in general, satisfactory results are obtained when the compounds are administered at a daily dosage of about 0.5 to about 500 mg/kg of animal body weight, about 1 to about 400 mg/kg, about 5 to about 300 mg/kg, about 10 to about 250 mg/kg, about 50 to about 200 mg/kg, or about 100 to 150 mg/kg. For most large mammals, the total daily dosage is from about 1 to 100 mg. In one embodiment, the total daily dosage is from about 2 to 80 mg. This dosage regimen may be adjusted to provide the optimal therapeutic response. For example, several divided doses may be administered daily or the dose may be proportionally reduced as indicated by the exigencies of the therapeutic situation.

As previously noted, the compounds may be administered via a vaginal ring. In one embodiment, the ring is inserted into the vagina and it remains in place for 3 weeks. During the fourth week, the vaginal ring is removed and menses occurs. The following week, a new ring is inserted to be worn another 3 weeks until it is time for the next period. In another embodiment, the vaginal ring is inserted weekly and is replaced for 3 consecutive weeks. Then, following 1 week without the ring, a new ring is inserted to begin a new regimen. In yet another embodiment, the vaginal ring is inserted for longer or shorter periods of time.

Further, the previously mentioned transdermal patch is applied via a suitable adhesive on the skin, where it remains in place for at least one week. In one embodiment, the transdermal patch remains in place for one week and is replaced weekly for a total of 3 weeks. In another embodiment, the transdermal patch remains in place for two weeks. In a further embodiment, the transdermal patch remains in place for three weeks. During the fourth week, no patch is applied and menses occurs. The following week, a new patch is applied to be worn to begin a new regimen. In yet another embodiment, the patch remains in place for longer or shorter periods of time.

When used for contraception, the method typically includes delivering a daily dosage unit containing a compound for 28 consecutive days to a female of child-bearing age. Desirably, the method includes delivering the compound over a period of 21 to 27 consecutive days followed by 1 to 7 consecutive days in which no effective amount or no amount of the compound is delivered. Optionally, the period of 1 to 7 days in which no effective amount of the compound is delivered to the subject can involve delivery of a second phase of daily dosage units of 1 to 7 days of a pharmaceutically acceptable placebo. Alternatively, during this "placebo period", no placebo is administered. The compound may optionally be administered in combination with a progestin, antiprogestin, estrogen, or combination thereof.

In another embodiment, the method includes delivering a compound for 21 consecutive days, followed by 7 days in which no effective amount of the compound is delivered. Optionally, during these 7 days, a second phase of 7 daily dosage units of an orally and pharmaceutically acceptable placebo can be delivered. The compound may optionally be administered in combination with a progestin, antiprogestin, estrogen, anti-estrogen, SERM or combination thereof.

In a further embodiment, the method includes delivering a compound for 23 consecutive days, followed by 5 days in which no effective amount of the compound is delivered. Optionally, during these 5 days, a second phase of 5 daily dosage units of an orally and pharmaceutically acceptable placebo can be delivered. The compound may optionally be administered in combination with a progestin, antiprogestin, estrogen, anti-estrogen, SERM or combination thereof.

In yet another embodiment, the method includes delivering a compound for 25 consecutive days, followed by 3 days in which no effective amount of the compound is delivered. Optionally, during these 3 days, a second phase of 3 daily dosage units of an orally and pharmaceutically acceptable placebo can be delivered. The compound may optionally be administered in combination with a progestin, antiprogestin, estrogen, anti-estrogen, SERM, or combination thereof.

In still a further embodiment, the method includes delivering a compound for 27 consecutive days, followed by 1 day in which no effective amount of the compound is delivered. Optionally, a second phase of 1 daily dosage unit of an orally and pharmaceutically acceptable placebo can be delivered. The compound may optionally be administered in combination with a progestin, antiprogestin, estrogen, anti-estrogen, SERM, or combination thereof.

In another embodiment, a method of contraception includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound described herein; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In yet a further embodiment, a method of contraception includes administering to a female of child bearing age for 28 consecutive days: (a) a first phase of from 14 to 24 daily dosage units of a compound described herein; (b) a second phase of from 1 to 11 daily dosage units of an antiprogestin; and (c) optionally, a third phase of daily dosage units of an orally and pharmaceutically acceptable placebo for the remaining days of the 28 consecutive days in which no antiprogestin, progestin, estrogen, anti-estrogen or SERM is administered; wherein the total daily dosage units of the first, second and third phases equals 28.

In yet a further embodiment, a method of contraception is provided and includes administering to a female of child bearing age for 28 consecutive days: (a) a first phase of from 14 to 24 daily dosage units of a progestational agent equal in progestational activity to about 35 to about 100 µg levonorgestrel; (b) a second phase of from 1 to 11 daily dosage units, at a daily dosage of from about 2 to 50 mg, of a compound described herein; and (c) optionally, a third phase of daily dosage units of an orally and pharmaceutically acceptable placebo for the remaining days of the 28 consecutive days in which no antiprogestin, progestin or estrogen is administered; wherein the total daily dosage units of the first, second and third phases equals 28.

In another embodiment, a method of contraception is provided and includes administering to a female of child bearing age for 28 consecutive days: (a) a first phase of from 14 to 24 daily dosage units of a compound described herein; (b) a second phase of from 1 to 11 daily dosage units of an antiprogestin; and (c) optionally, a third phase of daily dosage units of an orally and pharmaceutically acceptable placebo for the remaining days of the 28 consecutive days in which no antiprogestin, progestin, estrogen, anti-estrogen or SERM is administered; wherein the total daily dosage units of the first, second and third phases equals 28.

Also provided are kits or packages of pharmaceutical formulations designed for use in the regimens described herein. Suitably, the kits contain one or more compounds as described herein.

Advantageously, for use in the kits, the compound is formulated for the desired delivery vehicle and route. For example, the compound can be formulated for oral delivery, parenteral delivery, vaginal ring, transdermal delivery, or mucosal delivery, as discussed in detail above. The kit is preferably a pack (e.g. a blister pack) containing daily doses arranged in the order in which they are to be taken.

In each of the regimens and kits described herein, it is preferred that the daily dosage of each pharmaceutically active component of the regimen remain fixed in each particular phase in which it is administered. It is also understood that the daily dose units described are to be administered in the order described, with the first phase followed in order by the optional phases, including any second and third phases. To help facilitate compliance with each regimen, it is also preferred that the kits contain the placebo described for the final days of the cycle. It is further preferred that each package or kit contain a pharmaceutically acceptable package having indicators for each day of the 28-day cycle, such as a labeled blister package, dial dispenser, or other packages known in the art.

These dosage regimens may be adjusted to provide the optimal therapeutic response. For example, several divided doses of each component may be administered daily or the dose may be proportionally increased or reduced as indicated by the exigencies of the therapeutic situation. In the descriptions herein, reference to a daily dosage unit may also include divided units which are administered over the course of each day of the cycle contemplated.

In one embodiment, the kit is designed for daily oral administration over a 28-day cycle, desirably for one oral administration per day, and organized so as to indicate a single oral formulation or combination of oral formulations to be taken on each day of the 28-day cycle. Desirably each kit will include oral tablets to be taken on each the days specified; desirably one oral tablet will contain each of the combined daily dosages indicated. For example, a kit can contain 21 to 27 daily dosage units of an effective amount of the compound, optionally, 1 to 7 daily dosage units of a placebo and other appropriate components including, e.g., instructions for use.

In another embodiment, the kit is designed for weekly or monthly administration via a vaginal ring over a 28-day cycle. Suitably, such a kit contains individual packaging for each of the vaginal rings, i.e. one to three, required for a monthly cycle and other appropriate components, including, e.g., instructions for use.

In a further embodiment, the kit is designed for weekly or monthly administration via a transdermal patch over a 28-day cycle. Suitably, such a kit contains individual packaging for each of the patches, i.e. one to three, required for a monthly cycle and other appropriate components, including, e.g., instructions for use.

In still another embodiment, the kit is designed for parenteral delivery of the compound. Such a kit is typically designed for delivery at home and may include needles, syringes, and other appropriate packaging and instructions for use.

In yet another embodiment, the kit contains the compound in a gel or cream formulation. Optionally, the kit can include appropriate packaging such as a tube or other container, an applicator, and/or instructions for use.

In a further embodiment, the kit includes (a) a first phase of from 14 to 21 daily dosage units of a progestational agent equal in progestational activity to about 35 to about 150 μg levonorgestrel; (b) a second phase of from 1 to 11 daily dosage units of a compound described herein; and (c) a third phase of daily dosage units of an orally and pharmaceutically acceptable placebo; wherein the total number of the daily dosage units in the first phase, second phase and third phase equals 28.

In still another embodiment, a kit contains (a) a first phase of from 14 to 21 daily dosage units of a compound described herein; (b) a second phase of from 1 to 11 daily dosage units of an antiprogestin compound; and (c) a third phase of daily dosage units of an orally and pharmaceutically acceptable placebo; wherein the total number of the daily dosage units in the first phase, second phase and third phase equals 28.

The following examples are illustrative only and are not intended to be a limitation on the present invention.

EXAMPLES

Example 1

(4R)-3-[4-(4-Bromophenyl)-1,3-thiazol-2-yl]-4-methyl-1,3-oxazolidin-2-one

Step 1: 2-(4-Bromophenyl)-2-oxoethyl thiocyanate

A mixture of 2,4'-dibromoacetophenone (56.08 g, 0.20 mol) and potassium thiocyanate (21.57 g, 0.22 mol) in 1 L of absolute ethanol was stirred under nitrogen at room temperature for 5 h. The reaction was added to 2 L of water and the mixture stirred at room temperature for 2 h. The solid present was collected by filtration, rinsed with water, ice-cold ethanol, hexane, and then dried under high vacuum to give 2-(4-bromophenyl)-2-oxoethyl thiocyanate (50.39 g, 98%) as a white solid, mp 148-149° C.

Step 2: 2-Bromo-4-(4-bromophenyl)-1,3-thiazole

A suspension of 2-(4-bromophenyl)-2-oxoethyl thiocyanate (5.12 g, 20.0 mmol), prepared in the previous step, in 30 mL of 30% hydrogen bromide in acetic acid was stirred under nitrogen at room temperature for 7 h. The yellow suspension was poured into 200 mL of 1 N NaOH (exotherm) and the mixture stirred at room temperature for 17 h. The solid present was collected by filtration, rinsed with water, ice-cold ethanol, hexane and then dried under high vacuum to give 2-bromo-4-(4-bromophenyl)-1,3-thiazole (5.36 g, 84%) as a light yellow solid, mp 117-119° C.; MS (ES) m/z 318/320/322 [M+H]$^+$.

Step 3: (2R)-2-{[4-(4-Bromophenyl)-1,3-thiazol-2-yl]amino}propan-1-ol

A mixture of 2-bromo-4-(4-bromophenyl)-1,3-thiazole (3.00 g, 9.41 mmol), prepared in the previous step, and (R)-(−)-2-amino-1-propanol (2.20 mL, 28.3 mmol) was stirred under nitrogen at 150° C. for 11.5 h. The product was dissolved in 20% methanol-methylene chloride and extracted with 5% NaHCO$_3$. The organic layer was separated and the aqueous layer was extracted three times with 20% methanol-methylene chloride. The combined extracts were dried (anhydrous MgSO$_4$), filtered and the solvent removed under reduced pressure to give 3.08 g of a yellow residue. Purification of the residue on 500 g of silica gel (230-400 mesh) using 1:1 methylene chloride-hexane to methylene chloride as the eluents to remove starting material and non-polar impurities and then 30% ethyl acetate-methylene chloride gave (2R)-2-{[4-(4-bromophenyl)-1,3-thiazol-2-yl]amino}propan-1-ol (2.09 g, 71%) as a yellow oil, MS (ES) m/z 313.0 [M+H]$^+$.

Step 4: (4R)-3-[4-(4-Bromophenyl)-1,3-thiazol-2-yl]-4-methyl-1,3-oxazolidin-2-one Triphosgene (2.62 g, 8.82 mmol) in 60 mL of methylene chloride was added under nitrogen dropwise over 1.75 h to a solution of (2R)-2-{[4-(4-bromophenyl)-1,3-thiazol-2-yl]amino}propan-1-ol (2.30 g, 7.33 mmol), prepared in the previous step, and N,N-diisopropylethylamine in 125 mL of methylene chloride at ice-bath temperature. After the addition, the reaction was stirred at ice-bath temperature for 3.5 h.

The ice bath was removed and the stirring continued for 15 h. The reaction was extracted with 2 N HCl, dried (anhydrous MgSO$_4$), filtered and the solvent removed under reduced pressure to give 2.81 g of a yellow solid. Purification of the solid on 500 g of silica gel (230-400 mesh) using 30% methylene chloride-hexane to methylene chloride as the eluents gave the title compound (2.07 g, 83%) as a white solid, mp 197-199° C.; MS (ES) m/z 339.0 [M+H]$^+$; Anal. Calcd for C$_{13}$H$_{11}$BrN$_2$O$_2$S: C, 46.03; H, 3.27; N, 8.26. Found: C, 45.80; H, 3.13; N, 8.16.

Example 2

4-{2-[(4R)-4-Methyl-2-oxo-1,3-oxazolidin-3-yl]-1,3-thiazol-4-yl}benzonitrile

A mixture of (4R)-3-[4-(4-bromophenyl)-1,3-thiazol-2-yl]-4-methyl-1,3-oxazolidin-2-one (1.36 g, 4.01 mmol), prepared in step 4 of Example 1, and zinc cyanide (283.4 mg, 2.41 mmol) in 35 mL of anhydrous N,N-dimethylformamide was degassed and put under a nitrogen atmosphere. Tetrakis (triphenylphosphine)palladium(0) was added and the mixture again degassed and put under a nitrogen atmosphere. The mixture was then stirred at 120° C. for 1.5 h. After cooling to room temperature, the reaction was partitioned between ethyl acetate and water. The organic layer was separated, extracted one time with 2 N NaOH, five times with water, dried (anhydrous MgSO$_4$), filtered and the solvent removed under reduced pressure to give 1.30 g of a brown solid. Purification of the solid on 500 g of silica gel (230-400 mesh) using 70% methylene chloride-hexane to 5% ethyl acetate-methylene chloride as the eluents gave the title compound (1.03 g, 91%) as a white solid, mp 227-228° C.; MS m/z 286 [M+H$^+$]; Anal. Calcd for C$_{14}$H$_{11}$N$_3$O$_2$S.0.03 CH$_2$Cl$_2$: C, 58.54; H, 3.87; N, 14.60. Found: C, 58.41; H, 3.82; N, 14.40.

Example 3

(4S)-3-[4-(4-Bromophenyl)-1,3-thiazol-2-yl]-4-methyl-1,3-oxazolidin-2-one

Step 1: (2S)-2-{[4-(4-Bromophenyl)-1,3-thiazol-2-yl]amino}propan-1-ol

A mixture of 2-bromo-4-(4-bromophenyl)-1,3-thiazole (1.01 g, 3.16 mmol), prepared in step 2 of Example 1, and (S)-(+)-2-amino-1-propanol (738 µL, 9.48 mmol) was stirred under nitrogen at 150° C. for 1 h. After cooling to room temperature, the solid was taken up in methylene chloride and purified on a Horizon™ Flash Collector (the Biotage FLASH 40+™ cartridge) using a linear gradient of 10% ethyl acetate-methylene chloride to 40% ethyl acetate-methylene chloride as the eluent. Isolation of the more polar fraction gave (2S)-2-{[4-(4-bromophenyl)-1,3-thiazol-2-yl]amino}propan-1-ol (415 mg, 42%) as a yellow oil; MS (ES) m/z 313.0 [M+H]$^+$.

Step 2: (4S)-3-[4-(4-Bromophenyl)-1,3-thiazol-2-yl]-4-methyl-1,3-oxazolidin-2-one In the same manner as described in step 4 of Example 1, replacing (2R)-2-{[4-(4-bromophenyl)-1,3-thiazol-2-yl]amino}propan-1-ol with (2S)-2-{[4-(4-bromophenyl)-1,3-thiazol-2-yl]amino}propan-1-ol, prepared in the previous step, and purification of the residue on a Horizon™ Flash Collector (the Biotage FLASH 25+™ cartridge) using a linear gradient of 30% methylene-chloride-hexane-50% methylene-chloride-hexane as the eluent gave the title compound (284 mg, 71%) as a white solid; mp 196-198; MS (ES) m/z 339.0 [M+H]$^+$. Anal. Calcd for C$_{13}$H$_{11}$BrN$_2$O$_2$S: C, 46.03; H, 3.27; N, 8.26. Found: C, 47.06; H, 3.39; N, 7.90.

Example 4

4-{2-[(4S)-4-Methyl-2-oxo-1,3-oxazolidin-3-yl]-1,3-thiazol-4-yl}benzonitrile

In the manner as described in Example 2, replacing (4R)-3-[4-(4-bromophenyl)-1,3-thiazol-2-yl]-4-methyl-1,3-oxazolidin-2-one with (4S)-3-[4-(4-bromophenyl)-1,3-thiazol-2-yl]-4-methyl-1,3-oxazolidin-2-one, prepared in step 2 of Example 3, and purification of the residue on a Horizon™ Flash Collector (the Biotage FLASH 25+ cartridge) using a linear gradient of 5% ethyl acetate-hexane to 100% ethyl acetate gave the title compound (14.7 mg, 73%) as a white solid, mp 205-207° C.; MS (ESI) m/z 286 [M+H]$^+$.

Example 5

3-[4-(4-Bromophenyl)-1,3-thiazol-2-yl]-4,4-dimethyl-1,3-oxazolidin-2-one

Step 1: 2-{[4-(4-Bromophenyl)-1,3-thiazol-2-yl]amino}-2-methylpropan-1-ol

A mixture of 2-bromo-4-(4-bromophenyl)-1,3-thiazole (4.01 g, 12.6 mmol), prepared in step 2 of Example 1, and 2-amino-2-methyl-1-propanol (3.6 mL, 37.7 mmol) was stirred under nitrogen at 150° C. for 4.5 h. An additional 3.6 mL (37.7 mmol) of 2-amino-2-methyl-1-propanol was added and the mixture stirred under nitrogen at 150° C. for 52 h. The reaction was dissolved in 20% methanol-methylene chloride and extracted with 5% NaHCO$_3$. The organic layer was separated and the aqueous layer was extracted three times with 20% methanol-methylene chloride. The combined extracts were dried (anhydrous MgSO$_4$), filtered and the solvent removed under reduced pressure to give 4.30 g of a brown oil. Purification of the oil on 500 g of silica gel (230-400 mesh) using 1% ethyl acetate-methylene chloride to 8% ethyl acetate-methylene chloride as the eluent gave 2-{[4-(4-bromophenyl)-1,3-thiazol-2-yl]amino}-2-methylpropan-1-ol (1.41 g, 34%) as a yellow solid, mp 151-153° C.; MS (ESI) m/z 327/329 [M+H]$^+$.

Step 2: 3-[4-(4-Bromophenyl)-1,3-thiazol-2-yl]-4,4-dimethyl-1,3-oxazolidin-2-one In the same manner as described in step 4 of Example 1, replacing (2R)-2-{[4-(4-bromophenyl)-1,3-thiazol-2-yl]amino}propan-1-ol with 2-{[4-(4-bromophenyl)-1,3-thiazol-2-yl]amino}-2-methylpropan-1-ol, prepared in the previous step, gave 1.74 g of a yellow solid. Purification of the solid on 300 g of silica gel (230-400 mesh) using 2:1 methylene chloride:hexane as the eluents gave the title compound (1.24 g, 84%) as a white solid, mp 165-167° C.; MS (ES) m/z 353.0; [M+H]$^+$. Anal. Calcd for C$_{14}$H$_{13}$BrN$_2$O$_2$S: C, 47.60; H, 3.71; N, 7.93. Found: C, 47.70; H, 3.24; N, 7.79.

Example 6

4-[2-(4,4-Dimethyl-2-oxo-1,3-oxazolidin-3-yl)-1,3-thiazol-4-yl]benzonitrile

In the manner as described in Example 2, replacing (4R)-3-[4-(4-bromophenyl)-1,3-thiazol-2-yl]-4-methyl-1,3-oxazolidin-2-one with 3-[4-(4-bromophenyl)-1,3-thiazol-2-yl]-4,4-dimethyl-1,3-oxazolidin-2-one, prepared in step 2 of Example 5, gave 824 mg of a brown solid. Purification of the solid on 250 g of silica gel (230-400 mesh) using 1:1 methylene chloride:hexane to 2:1 methylene chloride:hexane as the eluent gave the title compound (593 mg, 79%) as a white solid, mp 183-185° C.; MS (ES) m/z 300.1 [M+H]+. Anal. Calcd for $C_{15}H_{13}N_3O_2S$: C, 60.19; H, 4.38; N, 14.04. Found: C, 60.05; H, 4.15; N, 14.03.

Example 7

(4S)-3-[4-(4-Bromophenyl)-1,3-thiazol-2-yl]-4-ethyl-1,3-oxazolidin-2-one

Step 1: (2S)-2-{[4-(4-Bromophenyl)-1,3-thiazol-2-yl]amino}butan-1-ol

A mixture of 2-bromo-4-(4-bromophenyl)-1,3-thiazole (5.01 g, 15.7 mmol), prepared in step 2 of Example 1, and (S)-(+)-2-amino-1-butanol (4.45 mL, 47.1 mmol) was stirred under nitrogen at 150° C. for 12.5 h. After cooling to room temperature, the reaction was dissolved in 20% methanol-methylene chloride and extracted with 5% $NaHCO_3$. The organic layer was separated and the aqueous layer was extracted three times with 20% methanol-methylene chloride. The combined extracts were dried (anhydrous $MgSO_4$), filtered and the solvent removed under reduced pressure to give 5.40 g of a yellow oil. Purification of the oil on 500 g of silica gel (230-400 mesh) using 5% ethyl acetate-methylene chloride to 40% ethyl acetate-methylene as the eluent gave (2S)-2-{[4-(4-bromophenyl)-1,3-thiazol-2-yl]amino}butan-1-ol (4.22 g, 82%) as a yellow solid, mp 91-93° C.; MS (ES) m/z 326.9 [M+H]+.

Step 2: (4S)-3-[4-(4-Bromophenyl)-1,3-thiazol-2-yl]-4-ethyl-1,3-oxazolidin-2-one In the same manner as described in step 4 of Example 1, replacing (2R)-2-{[4-(4-bromophenyl)-1,3-thiazol-2-yl]amino}propan-1-ol with (2S)-2-{[4-(4-bromophenyl)-1,3-thiazol-2-yl]amino}butan-1-ol, prepared in the previous step, gave 4.68 g of a yellow solid. Purification of the solid on 500 g of silica gel (230-400 mesh) using methylene chloride as the eluent gave the title compound (3.83 g, 91%) as a white solid, mp 138-140° C.; MS (ES) m/z 352.8 [M+H]+. Anal. Calcd for $C_{14}H_{13}BrN_2O_2S$: C, 47.60; H, 3.71; N, 7.93. Found: C, 47.35; H, 3.50; N, 7.79.

Example 8

4-{2-[(4S)-4-Ethyl-2-oxo-1,3-oxazolidin-3-yl]-1,3-thiazol-4-yl}benzonitrile

In the manner as described in Example 2, replacing (4R)-3-[4-(4-bromophenyl)-1,3-thiazol-2-yl]-4-methyl-1,3-oxazolidin-2-one with (4S)-3-[4-(4-bromophenyl)-1,3-thiazol-2-yl]-4-ethyl-1,3-oxazolidin-2-one, prepared in step 2 of Example 7, gave 2.05 g of a green solid. Purification of the solid on 500 g of silica gel (230-400 mesh) using 70% methylene chloride-hexane to 100% methylene chloride as the eluents gave the title compound (1.59 g, 91%) as a white solid, mp 173-175; MS (ES) m/z 300.0 [M+H]+.

Example 9

(4R)-3-[4-(4-Bromophenyl)-1,3-thiazol-2-yl]-4-ethyl-1,3-oxazolidin-2-one

Step 1: (2R)-2-{[4-(4-Bromophenyl)-1,3-thiazol-2-yl]amino}butan-1-ol

A mixture of R-2-aminobutanol (2.88 g, 32.4 mmol) and 2-bromo-4-(4-bromophenyl)-thiazole (3.45 g, 10.8 mmol) was heated at 160° C. for 17 h. The mixture was cooled to room temperature, diluted with ethyl acetate, washed with a saturated aqueous sodium hydrogen carbonate solution, dried (anhydrous $MgSO_4$) and evaporated. The residue was purified by silica gel column chromatography (ethyl acetate:hexanes, 1:3) to afford (2R)-2-{[4-(4-bromophenyl)-1,3-thiazol-2-yl]amino}butan-1-ol (2.80 g, 79%) which was used without further characterization.

Step 2: (4R)-3-[4-(4-Bromophenyl)-1,3-thiazol-2-yl]-4-ethyl-1,3-oxazolidin-2-one (2R)-2-{[4-(4-bromophenyl)-1,3-thiazol-2-yl]amino}butan-1-ol (2.80 g, 8.56 mmol), prepared in the previous step, and triethylamine (10.5 mL, 60 mmol) in dry dichloromethane (75 mL) was cooled to 0° C. under a nitrogen atmosphere. Triphosgene (5.90 g, 20 mmol) in dry dichloromethane (25 mL) was then added drop wise. After 16 h, the mixture was washed with water and dried (anhydrous $MgSO_4$). The crude product was recrystallized from diethyl ether to afford (4R)-3-[4-(4-bromophenyl)-1,3-thiazol-2-yl]-4-ethyl-1,3-oxazolidin-2-one (1.46 g, 4.1 mmol). mp 134-135° C.; $[\alpha]D25=-46°$ (c=0.0107 g/mL, DMSO); MS (ES) m/z 353.0; HPLC purity 100% at 210-370 nm, 10.8 min; 100% at 270 nm, 10.8 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min. Anal. Calcd for $C_{14}H_{13}BrN_2O_2S$: C, 47.60; H, 3.71; N, 7.93. Found: C, 47.45; H, 3.43; N, 7.74.

Example 10

4-{2-[(4R)-4-Ethyl-2-oxo-1,3-oxazolidin-3-yl]-1,3-thiazol-4-yl}benzonitrile

To a solution of (4R)-3-[4-(4-bromophenyl)-1,3-thiazol-2-yl]-4-ethyl-1,3-oxazolidin-2-one (1.46 g, 4.13 mmol), prepared in step 2 of Example 9, in dry DMF (15 mL) was added zinc cyanide (0.266 g, 2.27 mmol) and tetrakis(triphenylphosphine)palladium (0) (150 mg), under nitrogen, and the mixture heated to 145° C. After 1 h, the mixture was cooled to room temperature, diluted with ethyl acetate, which was then washed with water, brine, dried (anhydrous sodium sulfate) and evaporated. The residue was purified by silica gel column chromatography (ethyl acetate:hexanes, gradient elution) to afford the title compound (0.67 g, 54%), mp 153-157° C., MS m/z 300 [M+H]+. ANLC 100% at 210-370 nm, 9.5 min; 100% at 240 nm, 9.5 min, Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Example 11

(4S)-3-[4-(4-Bromophenyl)-5-fluoro-1,3-thiazol-2-yl]-4-ethyl-1,3-oxazolidin-2-one The Selectfluor® reagent (2.2125 g, 6.25 mmol) in 250 mL of acetonitrile was added under nitrogen dropwise over 1.5 h to a solution of (4S)-3-[4-(4-bromophenyl)-1,3-thiazol-2-yl]-4-ethyl-1,3-oxazolidin-2-one (2.0015 g, 5.67 mmol), prepared in step 2 of Example 7, in 250 mL of acetonitrile at room temperature. After the addition, the reaction was stirred at room temperature for 21.5 h. The reaction was concentrated under reduced pressure to remove the acetonitrile. The residue was partitioned between methylene chloride and 2 N HCl. The organic layer was separated and the aqueous layer extracted three times with methylene chloride. The combined extracts were dried (anhydrous $MgSO_4$), filtered and the solvent removed under reduced pressure to give 2.11 g of a tan foam. Purification of the foam on 800 g of silica gel (230-400 mesh) using 50% methylene chloride-hexane to 100% methylene chloride as the eluents gave the title compound (914.8 mg, 44%) as a white solid, mp 105-107° C.; MS (ES) m/z 370.9 [M+H]$^+$; Anal. Calcd for $C_{14}H_{12}BrFN_2O_2S$: C, 45.30; H, 3.26; N, 7.55. Found: C, 45.53; H, 3.09; N, 7.37.

Example 12

4-{2-[(4S)-4-Ethyl-2-oxo-1,3-oxazolidin-3-yl]-5-fluoro-1,3-thiazol-4-yl}benzonitrile In the same manner as described in Example 11, and replacing (4S)-3-[4-(4-bromophenyl)-1,3-thiazol-2-yl]-4-ethyl-1,3-oxazolidin-2-one with 4-{2-[(4S)-4-ethyl-2-oxo-1,3-oxazolidin-3-yl]-1,3-thiazol-4-yl}benzonitrile, prepared in Example 8, gave the title compound (521.5 mg, 32%) as a white solid, mp 157-159° C.; MS (ES) m/z 317.9 [M+H]$^+$; Anal. Calcd for $C_{15}H_{12}FN_3O_2S$: C, 56.77; H, 3.81; N, 13.24. Found: C, 56.63; H, 3.12; N, 12.93

Example 13

(4S)-3-[4-(4-Bromophenyl)-5-chloro-1,3-thiazol-2-yl]-4-ethyl-1,3-oxazolidin-2-one Step 1: (2S)-2-{[4-(4-Bromophenyl)-5-chloro-1,3-thiazol-2-yl]amino}butan-1-ol A solution of N-chlorosuccinimide (975.0 mg, 7.30 mmol) in 50 mL of methylene chloride was added under nitrogen at room temperature dropwise over 45 min to a solution of (2S)-2-{[4-(4-bromophenyl)-1,3-thiazol-2-yl]amino}butan-1-ol (2.1611 g, 6.60 mmol), prepared in step 1 of Example 7, in 50 mL of methylene chloride. After the addition, the reaction was stirred at room temperature for 3 h. The reaction was poured directly onto a column of silica gel (230-400 mesh). Elution of the column with 5% ethyl acetate-methylene chloride to 15% ethyl acetate-methylene chloride gave (2S)-2-{[4-(4-bromophenyl)-5-chloro-1,3-thiazol-2-yl]amino}butan-1-ol (1.5371 g, 64%) as a yellow foam, MS (ES) m/z 358.8 [M+H]$^+$.

Step 2: (4S)-3-[4-(4-Bromophenyl)-5-chloro-1,3-thiazol-2-yl]-4-ethyl-1,3-oxazolidin-2-one In the same manner as described in step 4 of Example 1, and replacing (2R)-2-{[4-(4-bromophenyl)-1,3-thiazol-2-yl]amino}propan-1-ol with (2S)-2-{[4-(4-bromophenyl)-5-chloro-1,3-thiazol-2-yl]amino}butan-1-ol (1.4708 g, 4.07 mmol), prepared in the previous step, gave 1.87 g of a yellow solid. Purification of the solid on 400 g of silica gel (230-400 mesh) using 50% methylene chloride-hexane to 60% methylene chloride-hexane as the eluents gave the title compound (1.0806 g, 68%) as a white solid, mp 137-139° C.; MS (ES) m/z 386.9 [M+H]$^+$; Anal. Calcd for $C_{14}H_{12}BrClN_2O_2S$: C, 43.37; H, 3.12; N, 7.23. Found: C, 43.53; H, 2.74; N, 7.17.

Example 14

4-{5-Chloro-2-[(4S)-4-ethyl-2-oxo-1,3-oxazolidin-3-yl]-1,3-thiazol-4-yl}benzonitrile In the manner as described in Example 2, replacing (4R)-3-[4-(4-bromophenyl)-1,3-thiazol-2-yl]-4-methyl-1,3-oxazolidin-2-one with (4S)-3-[4-(4-bromophenyl)-5-chloro-1,3-thiazol-2-yl]-4-ethyl-1,3-oxazolidin-2-one (823.9 mg, 2.13 mmol), prepared in step 2 of Example 13, gave 821.1 mg of a yellow solid. The solid was purified on 400 g of silica gel (230-400 mesh) using 70% methylene chloride-hexane to 100% methylene chloride as the eluents. Isolation of the major component from the column gave the title compound (550.4 mg, 77%) as a white solid, mp 157-159° C.; MS (ES) m/z 333.9 [M+H]$^+$. Anal. Calcd for $C_{15}H_{12}ClN_3O_2S$: C, 53.97; H, 3.62; N, 12.59. Found: C, 53.89; H, 3.26; N, 12.44.

Example 15

4-(4-Cyanophenyl)-2-[(4S)-4-ethyl-2-oxo-1,3-oxazolidin-3-yl]-1,3-thiazole-5-carbonitrile In the manner as described in Example 2, replacing (4R)-3-[4-(4-bromophenyl)-1,3-thiazol-2-yl]-4-methyl-1,3-oxazolidin-2-one with (4S)-3-[4-(4-bromophenyl)-5-chloro-1,3-thiazol-2-yl]-4-ethyl-1,3-oxazolidin-2-one (823.9 mg, 2.13 mmol), prepared in step 2 of Example 13, gave 821.1 mg of a yellow solid. The solid was purified on 400 g of silica gel (230-400 mesh) using 70% methylene chloride-hexane to 100% methylene chloride as the eluents. Isolation of a minor component from the column gave the title compound (65.9 mg, 10%) as a white solid, mp 201-203° C.; MS (ES) m/z 324.9 [M+H]$^+$. Anal. Calcd for $C_{16}H_{12}N_4O_2S$: C, 59.25; H, 3.73; N, 17.27. Found: C, 59.05; H, 3.10; N, 16.83.

Example 16

(4R)-3-[4-(3-bromophenyl)-1,3-thiazol-2-yl]-4-methyl-1,3-oxazolidin-2-one

Step 1: 2-(3-Bromophenyl)-2-oxoethyl thiocyanate

A mixture of 2,3'-dibromoacetophenone (13.5436 g, 48.7 mmol) and potassium thiocyanate (5.2125 g, 53.6 mmol) in 200 mL of absolute ethanol was stirred under nitrogen at room temperature for 5.5 h. The reaction was added to 600 mL of water and the mixture stirred at room temperature for 2 h. The solid present was collected by filtration, rinsed with water, ice-cold ethanol, hexane and then dried under high vacuum to give 2-(3-bromophenyl)-2-oxoethyl thiocyanate (11.5591 g, 93%) as a white solid, mp 91-93° C.; MS (ES) m/z 253.8 [M+H]$^+$.

Step 2: 2-Bromo-4-(3-bromophenyl)-1,3-thiazole

A suspension of 2-(3-bromophenyl)-2-oxoethyl thiocyanate (10.9075 g, 42.6 mmol), prepared in the previous step, in 64 mL of 30% hydrogen bromide in acetic acid was stirred under nitrogen at room temperature for 17 h. The yellow suspension was poured into 500 mL of 1 N NaOH (exotherm) and the mixture stirred at room temperature for 21 h. The solid present was collected by filtration, rinsed with water, ice-cold ethanol, hexane and then dried under high vacuum to give 2-bromo-4-(3-bromophenyl)-1,3-thiazole (11.3069 g, 83%) as a yellow solid, mp 88-90° C.; MS (ES) m/z 317.9 [M+H$^+$].

Step 3: (2R)-2-{[4-(3-Bromophenyl)-1,3-thiazol-2-yl]amino}propan-1-ol

In the same manner as described in step 3 of Example 1, and replacing 2-bromo-4-(4-bromophenyl)-1,3-thiazole with 2-bromo-4-(3-bromophenyl)-1,3-thiazole (1.0490 g, 3.29 mmol), prepared in the previous step, gave 1.0292 g of a brown oil. Purification of the oil on a Horizon™ Flash Collector (the Biotage FLASH 40+™ cartridge) using a linear gradient of 5% ethyl acetate-methylene chloride to 30% ethyl acetate-methylene chloride as the eluents gave (2R)-2-{[4-(3-bromophenyl)-1,3-thiazol-2-yl]amino}propan-1-ol (799.0 mg, 78%) as a brown oil, MS (ES) m/z 313.0 [M+H]$^+$.

Step 4: (4R)-3-[4-(3-Bromophenyl)-1,3-thiazol-2-yl]-4-methyl-1,3-oxazolidin-2-one In the same manner as described in step 4 of Example 1, replacing (2R)-2-{[4-(4-bromophenyl)-1,3-thiazol-2-yl]amino}propan-1-ol with (2R)-2-{[4-(3-bromophenyl)-1,3-thiazol-2-yl]amino}propan-1-ol (722.2 mg, 2.31 mmol), prepared in the previous step, gave 908.9 mg of a yellow solid. Purification of the solid on a Horizon™ Flash Collector (the Biotage FLASH 40+™ cartridge) using a linear gradient of 30% methylene chloride-hexane to 70% methylene chloride-hexane as the eluents gave the title compound as a white solid, mp 126-128° C.; MS (ESI) m/z 339/341 [M+H]$^+$. Anal. Calcd for $C_{13}H_{\phantom{0}}BrN_2O_2S.0.04 CH_2Cl_2$: C, 45.72; H, 3.26; N, 8.18. Found: C, 45.79; H, 2.48; N, 8.05.

Example 17

3-{2-[(4R)-4-Methyl-2-oxo-1,3-oxazolidin-3-yl]-1,3-thiazol-4-yl}benzonitrile In the same manner as described in Example 2, replacing (4R)-3-[4-(4-bromophenyl)-1,3-thiazol-2-yl]-4-methyl-1,3-oxazolidin-2-one with (4R)-3-[4-(3-bromophenyl)-1,3-thiazol-2-yl]-4-methyl-1,3-oxazolidin-2-one (464.3 mg, 1.37 mmol), prepared in step 4 of Example 16, gave 447.2 mg of a brown solid. Purification of the solid on a Horizon™ Flash Collector (the Biotage FLASH 40+™ cartridge) using a linear gradient of 70% methylene chloride-hexane to 100% methylene chloride as the eluents gave the title compound as a white solid, mp 187-189° C.; MS (ES) m/z 286.0 [M+H]$^+$. Anal. Calcd for $C_{14}H_{11}N_3O_2S$: C, 58.93; H, 3.89; N, 14.73. Found: C, 58.66; H, 3.60; N, 14.54.

Example 18

3-[4-(3-Bromophenyl)-1,3-thiazol-2-yl]-4,4-dimethyl-1,3-oxazolidin-2-one

Step 1: 2-{[4-(3-Bromophenyl)-1,3-thiazol-2-yl]amino}-2-methylpropan-1-ol

A mixture of 2-bromo-4-(3-bromophenyl)-1,3-thiazole (605.0 mg, 1.90 mmol), prepared in step 2 of Example 16, and 2-amino-2-methyl-1-propanol (5.0 mL, 52.4 mmol) was heated in a Emrys™ Optimizer microwave reactor at 200° C. for 2.5 h. The reaction was partitioned between ethyl acetate and water. The ethyl acetate layer was separated, washed four times with water, dried (anhydrous $MgSO_4$) and the solvent removed under reduced pressure to give 581.2 mg of a brown oil. Purification of the solid on a Horizon™ Flash Collector (the Biotage FLASH 40+™ cartridge) using a linear gradient of 5% ethyl acetate-methylene chloride to 10% ethyl acetate-methylene chloride as the eluents gave 2-{[4-(3-bromophenyl)-1,3-thiazol-2-yl]amino}-2-methylpropan-1-ol (120.9 mg, 19%) as a tan solid, mp 116-120° C.; MS (ESI) m/z 327/329 [M+H]$^+$.

Step 2: 3-[4-(3-Bromophenyl)-1,3-thiazol-2-yl]-4,4-dimethyl-1,3-oxazolidin-2-one In the same manner as described in step 4 of Example 1, replacing (2R)-2-{[4-(4-bromophenyl)-1,3-thiazol-2-yl]amino}propan-1-ol with 2-{[4-(3-bromophenyl)-1,3-thiazol-2-yl]amino}-2-methylpropan-1-ol (91.5 mg, 0.280 mmol), prepared in the previous step, gave 107.8 mg of a tan solid. Purification on a Horizon™ Flash Collector (the Biotage FLASH 25+™ cartridge) using a linear gradient of 50% methylene chloride-hexane to 80% methylene chloride-hexane as the eluents gave the title compound (83.5 mg, 84%) as a white solid, mp 142-144° C.; MS (ES) m/z 352.9 [M+H]$^+$. Anal. Calcd for $C_{14}H_{13}BrN_2O_2S$: C, 47.60; H, 3.71; N, 7.93. Found: C, 47.75; H, 3.77; N, 7.71.

Example 19

4-[2-(4,4-Diethyl-2-oxo-1,3-oxazolidin-3-yl)-1,3-thiazol-4-yl]benzonitrile

Step 1: Ethyl 2-[(diphenylmethylene)amino]-2-ethylbutanoate

A solution of potassium bis(trimethylsilyl)amide (15.02 g, 75.3 mmol) in 80 mL of anhydrous tetrahydrofuran was added under nitrogen dropwise over 30 min to a solution of N-(diphenylmethylene)glycine ethyl ester (18.34 g, 68.6 mmol) in 300 mL of anhydrous tetrahydrofuran at dry ice-acetone temperature. After the addition, the reaction was stirred at dry ice-acetone temperature for 1 h. Iodoethane (6.60 mL, 82.5 mmol) was added over 2 min. The cooling bath was removed and the stirring continued for 3.5 h. Reaction cooled to dry ice-acetone temperature. A solution of potassium bis(trimethylsilyl)amide (15.02 g, 75.3 mmol) in 100 mL of anhydrous tetrahydrofuran was added dropwise over 30 min. After the addition, the reaction was stirred at dry ice-acetone temperature for 1 h. Iodoethane (6.60 mL, 82.5 mmol) was added over 2 min. The cooling bath was removed and the reaction stirred for 17 h. The reaction was concentrated under reduced pressure to remove most of the tetrahydrofuran. The residue was partitioned between methylene chloride and water. The organic layer was separated and the aqueous layer extracted three times with methylene chloride. The combined extracts were washed with saturated sodium chloride, dried (anhydrous $MgSO_4$), filtered and the solvent removed under reduced pressure to give ethyl 2-[(diphenylmethylene)amino]-2-ethylbutanoate (21.50 g, 97%) as a yellow oil, MS (ESI) m/z 324 [M+H]$^+$.

Step 2: Ethyl 2-amino-2-ethylbutanoate

A solution of ethyl 2-[(diphenylmethylene)amino]-2-ethylbutanoate (20.79 g, 64.3 mmol), prepared in the previous step, in 200 mL of diethyl ether was cooled under nitrogen to ice-bath temperature. 1 N HCl (96 mL, 96.0 mmol) was added dropwise over 45 min. After the addition, the ice-bath was removed and the stirring continued for 15 h. The diethyl ether layer was separated and the aqueous layer was extracted two times with 50 mL of methylene chloride. The methylene chloride extracts were extracted two times with 40 mL of 2 N HCl. The aqueous layers were combined and concentrated under reduced pressure to give an oil. The oil was taken up in 200 mL of saturated $NaHCO_3$ and stirred for 30 min. The aqueous layer was then extracted five times with methylene chloride. The organic extracts were dried (anhydrous $MgSO_4$), filtered and the solvent removed under reduced pressure to give ethyl 2-amino-2-ethylbutanoate (9.3799 g, 92%) as a yellow liquid.

Step 3: 2-Amino-2-ethylbutan-1-ol

A solution of ethyl 2-amino-2-ethylbutanoate (9.0256 g, 56.7 mmol), prepared in the previous step, in 150 mL of anhydrous diethyl ether was added under nitrogen to a suspension of lithium aluminum hydride (10.78 g, 284 mmol) in 300 mL of anhydrous diethyl ether. The addition was at a rate that maintained a gentle reflux (1.5 h). After the addition, the reaction was stirred at room temperature for 15 h. The reaction was cooled to ice-bath temperature. Water (14 mL) was added dropwise, followed by the dropwise addition of 14 mL of 15% NaOH and then 42 mL of water. The cooling bath was removed and the stirring continued for 2 h. The reaction was filtered and the solid rinsed with diethyl ether. The combined diethyl ether filtrates were dried (anhydrous $MgSO_4$), filtered and the solvent removed under reduced pressure to give 2-amino-2-ethylbutan-1-ol (6.5330 g, 98%) as a yellow oil, MS (EI) m/z 118.1233 $[M+H]^+$.

Step 4: N-({[1-Ethyl-1-(hydroxymethyl)propyl]amino}carbonothioyl)benzamide

Benzoyl isothiocyanate (4.28 mL, 31.8 mmol) was added under nitrogen to a solution of 2-amino-2-ethylbutan-1-ol (3.7315 g, 31.8 mmol), prepared in the previous step, in 100 mL of anhydrous tetrahydrofuran (exotherm on addition). After the addition, the reaction was refluxed for 2.5 h. After cooling to room temperature, 100 mL of hexane was added. The solid that formed was collected by filtration and dried under reduced pressure to give N-({[1-ethyl-1-(hydroxymethyl)propyl]amino}carbonothioyl)benzamide (7.1406 g, 80%) as a white solid. mp 161-163° C.; MS (ESI) m/z 281 $[M+H]^+$.

Step 5: N-[1-ethyl-1-(hydroxymethyl)propyl]thiourea

A solution of N-({[1-ethyl-1-(hydroxymethyl)propyl]amino}carbonothioyl)benzamide (6.8779 g, 24.5 mmol), prepared in the previous step, and 1 M LiOH (29.4 mL, 29.4 mmol) in 200 mL of tetrahydrofuran plus 200 mL of methanol plus 100 mL of water was stirred under nitrogen at room temperature for 21 h. The reaction was concentrated under reduced pressure to remove most of the tetrahydrofuran and methanol. The solid present was collected by filtration and dried under reduced pressure to give N-[1-ethyl-1-(hydroxymethyl)propyl]thiourea (2.9228 g, 68%) as a white solid, mp 148-151° C.; MS (ESI) m/z 177 $[M+H]^+$.

Step 6: 4-(2-{[1-Ethyl-1-(hydroxymethyl)propyl]amino}-1,3-thiazol-4-yl)benzonitrile A solution of N-[1-ethyl-1-(hydroxymethyl)propyl]thiourea (1.5047 g, 8.54 mmol), prepared in the previous step, and 2-bromo-4'-cyano-acetophenone (1.9109 g, 8.53 mmol) in 100 mL of absolute ethanol was refluxed under nitrogen for 4 h. The solvent was removed under reduced pressure to give a yellow solid. The solid was dissolved in 10% methanol-methylene chloride and extracted with 5% $NaHCO_3$. The organic layer was separated and the aqueous layer was extracted three times with 10% methanol-methylene chloride. The combined organic extracts were dried (anhydrous $MgSO_4$), filtered and the solvent removed under reduced pressure to give 2.46 g of a yellow foam. Purification of the foam on 300 g of silica gel (230-400 mesh) using 10% ethyl acetate-methylene chloride as the eluent gave 4-(2-{[1-ethyl-1-(hydroxymethyl)propyl]amino}-1,3-thiazol-4-yl)benzonitrile (2.2236 g, 87%) as a yellow solid, mp 118-120° C.; MS (ES) m/z 302.1 $[M+H]^+$.

Step 7: 4-[2-(4,4-Diethyl-2-oxo-1,3-oxazolidin-3-yl)-1,3-thiazol-4-yl]benzonitrile In the same manner as described in step 4 of Example 1, and replacing (2R)-2-{[4-(4-bromophenyl)-1,3-thiazol-2-yl]amino}propan-1-ol with 4-(2-{[1-ethyl-1-(hydroxymethyl)propyl]amino}-1,3-thiazol-4-yl)benzonitrile (1.9527 g, 6.48 mmol), prepared in the previous step, gave 2.1824 g of a yellow solid. Purification of the solid on 300 g of silica gel (230-400 mesh) using methylene chloride as the eluent gave the title compound (2.0424 g, 93%) as a white solid, mp 145-147° C.; MS (ESI) m/z 328 $[M+H]^+$. Anal. Calcd for $C_{17}H_{17}N_3O_2S \cdot 0.12\ CH_2Cl_2$: C, 60.91; H, 5.15; N, 12.45. Found: C, 61.19; H, 5.28; N, 12.55.

Example 20

(4R)-3-[4-(4-Bromophenyl)-1,3-thiazol-2-yl]-4-propyl-1,3-oxazolidin-2-one

Step 1: (2R)-2-{[4-(4-Bromophenyl)-1,3-thiazol-2-yl]amino}pentan-1-ol

A mixture of 2-bromo-4-(4-bromophenyl)-1,3-thiazole (2.9 g, 9.09 mmol), prepared in step 2 of Example 1, and (R)-(−)-2-amino-pentanol (2.82 g, 27.2 mmol) was stirred under nitrogen at 150° C. for 18 h. After cooling to room temperature, the residue was taken up in methylene chloride, applied to a Biotage FLASH 40+™ cartridge and the methylene chloride allowed to evaporate. Purification of the residue on the samplet on a Horizon™ Flash Collector (the Biotage FLASH 40+™ cartridge) using a linear gradient of 5% ethyl acetate-hexane to 100% ethyl acetate gave (2R)-2-{[4-(4-bromophenyl)-1,3-thiazol-2-yl]amino}pentan-1-ol (2.56 g, 83%) as a yellow solid, mp 63-65° C.; MS (ESI) m/z 341 $[M+H]^+$.

Step 2: (4R)-3-[4-(4-Bromophenyl)-1,3-thiazol-2-yl]-4-propyl-1,3-oxazolidin-2-one In the same manner as described in step 4 of Example 1, and replacing (2R)-2-{[4-(4-bromophenyl)-1,3-thiazol-2-yl]amino}propan-1-ol with (2R)-2-{[4-(4-bromophenyl)-1,3-thiazol-2-yl]amino}pentan-1-ol (2.4688 g, 7.23 mmol), prepared in the previous step, gave a brown residue. The residue was taken up in methylene chloride, applied to a Biotage FLASH 40+™ cartridge and the methylene chloride allowed to evaporate. Purification of the residue on the samplet on a Horizon™ Flash Collector (the Biotage FLASH 40+™ cartridge) using a linear gradient of 5% ethyl acetate-hexane to 100% ethyl acetate gave the title compound (2.172 g, 84%) as a white solid, mp 114-116° C.; MS (ESI) m/z 367 $[M+H]^+$. Anal. Calcd for $C_{15}H_{15}BrN_2O_2S$: C, 49.06; H, 4.12; N, 7.63. Found: C, 49.13; H, 3.91; N, 7.57.

Example 21

4-{2-[(4R)-2-oxo-4-propyl-1,3-oxazolidin-3-yl]-1,3-thiazol-4-yl}benzonitrile

In the manner as described in Example 2, and replacing (4R)-3-[4-(4-bromophenyl)-1,3-thiazol-2-yl]-4-methyl-1,3-oxazolidin-2-one with (4R)-3-[4-(4-bromophenyl)-1,3-thiazol-2-yl]-4-propyl-1,3-oxazolidin-2-one (1.3016 g, 3.54 mmol), prepared in step 2 of Example 20, gave a brown solid. The solid was taken up in methylene chloride, applied to a Biotage FLASH 40+™ cartridge and the methylene chloride allowed to evaporate. Purification of the residue on the samplet on a Horizon™ Flash Collector (the Biotage FLASH 40+™ cartridge) using a linear gradient of 5% ethyl acetate-hexane to 100% ethyl acetate gave the title compound (765 mg, 69%) as a white solid, mp 131-133° C.; MS (ES) m/z 314.0 $[M+H]^+$. Anal. Calcd for $C_{16}H_{15}N_3O_2S$: C, 61.32; H, 4.82; N, 13.41. Found: C, 61.28; H, 4.60; N, 13.34.

Example 22

(4S)-3-[4-(4-Bromophenyl)-1,3-thiazol-2-yl]-4-propyl-1,3-oxazolidin-2-one

Step 1: (2S)-2-{[4-(4-Bromophenyl)-1,3-thiazol-2-yl]amino}pentan-1-ol

In the same manner as described in step 1 of Example 20, and replacing (R)-(–)-2-amino-pentanol with (S)-(–)-2-amino-pentanol (2.81 g, 27.2 mmol) gave (2S)-2-{[4-(4-bromophenyl)-1,3-thiazol-2-yl]amino}pentan-1-ol (2.48 g, 80%) as a yellow solid, mp 61-63° C.; MS (ESI) m/z 341 [M+H]+.

Step 2: (4S)-3-[4-(4-Bromophenyl)-1,3-thiazol-2-yl]-4-propyl-1,3-oxazolidin-2-one In the same manner as described in step 2 of Example 20, and replacing (2R)-2-{[4-(4-bromophenyl)-1,3-thiazol-2-yl]amino}pentan-1-ol with (2S)-2-{[4-(4-bromophenyl)-1,3-thiazol-2-yl]amino}pentan-1-ol (2.4 g, 7.03 mmol), prepared in the previous step, gave the title compound (2.223 g, 84%) as a white solid, mp 116-118° C.; MS (ESI) m/z 367 [M+H]+; Anal. Calcd for $C_{15}H_{15}BrN_2O_2S$: C, 49.06; H, 4.12; N, 7.63. Found: C, 49.14; H, 3.92; N, 7.53.

Example 23

4-{2-[(4S)-2-oxo-4-propyl-1,3-oxazolidin-3-yl]-1,3-thiazol-4-yl}benzonitrile In the manner as described in Example 21, and replacing (4R)-3-[4-(4-bromophenyl)-1,3-thiazol-2-yl]-4-propyl-1,3-oxazolidin-2-one with (4S)-3-[4-(4-bromophenyl)-1,3-thiazol-2-yl]-4-propyl-1,3-oxazolidin-2-one (801.9 mg, 2.18 mmol), prepared in step 2 of Example 22, gave the title compound (456 mg, 67%) as a white solid, mp 132-135° C.; MS (ES) m/z 314.0 [M+H]+. Anal. Calcd for $C_{16}H_{15}N_3O_2S$: C, 61.32; H, 4.82; N, 13.41. Found: C, 61.34; H, 4.66; N, 13.35.

Example 24

4-[4-(4-Bromophenyl)-1,3-thiazol-2-yl]-6-oxa-4-azaspiro[2.4]heptane-5-one

Step 1: 1,1-Cyclopropanedicarboxylic acid monoethyl ester

1 N NaOH (275 mL, 275 mmol) was added under nitrogen dropwise to a solution of 1,1-cyclopropanedicarboxylic acid diethyl ester (51.3121 g, 275 mmol) in 400 mL of absolute ethanol at room temperature. After the addition, the reaction was allowed to stir at room temperature overnight. The reaction was concentrated under reduced pressure to remove most of the ethanol. The residue was partitioned between water and ether. The aqueous layer was separated, extracted with ether, acidified with 2 N HCl and extracted four times with ether. The combined extracts were dried (anhydrous $MgSO_4$) and the solvent removed under reduced pressure to give a yellow oil. The oil was dissolved in methylene chloride, dried ($MgSO_4$), filtered and the solvent removed under reduced pressure to give 1,1-cyclopropanedicarboxylic acid monoethyl ester (39.8275 g, 91%) as a yellow oil.

Step 2: 1-[[(1,1-Dimethylethoxy)carbonyl]amino] cyclopropane carboxylic acid ethyl ester Triethylamine (29.82 mL, 214 mmol) was added under nitrogen dropwise to a mixture of 1,1-cyclopropanedicarboxylic acid monoethyl ester (31.518 g, 199 mmol), prepared in the previous step, and diphenylphosphoryl azide (47.4 mL, 219 mmol) in 40 mL of tert-butanol at room temperature. After the addition, the reaction was refluxed for 5 h. The reaction was concentrated under reduced pressure. The residue was taken up in ethyl acetate and extracted three times each with 5% citric acid, saturated $NaHCO_3$ and saturated NaCl. The ethyl acetate layer was dried (anhydrous $MgSO_4$), filtered and the solvent removed under reduced pressure to give 1-[[(1,1-dimethylethoxy)carbonyl]amino]cyclopropane carboxylic acid ethyl ester (41.3931 g, 91%) as a yellow oil, MS (ES) m/z 130.0 [M+H-tBoc].

Step 3: 1-Ethoxycarbonyl-cyclopropyl-ammonium chloride

A saturated solution of HCl in ethyl acetate (20 mL) was added under nitrogen to a solution of 1-[[(1,1-dimethylethoxy)carbonyl]amino]cyclopropane carboxylic acid ethyl ester (10.07 g, 43.9 mmol), prepared in the previous step, in 20 mL of ethyl acetate at room temperature. After the addition, the reaction was stirred at room temperature for 1 h. The solid present was collected by filtration, rinsed with ethyl acetate and dried under reduced pressure to give 1-ethoxycarbonyl-cyclopropyl-ammonium chloride as a white solid.

Step 4: Ethyl 1-{[4-(4-bromophenyl)-1,3-thiazol-2-yl]amino}cyclopropane carboxylate Triethylamine (3.1 mL, 22.3 mmol) was added under nitrogen to a mixture of 2-(4-bromophenyl)-2-oxoethyl thiocyanate (5.2024 g, 20.3 mmol), prepared in step 1 of Example 1, and 1-ethoxycarbonyl-cyclopropyl-ammonium chloride (3.7001 g, 22.3 mmol), prepared in the previous step, in 400 mL of absolute ethanol. After the addition, the reaction was stirred at 65° C. for 4 days. The reaction was concentrated under reduced pressure to remove the ethanol. The residue was taken up in methylene chloride, applied to a Biotage FLASH 25+™ cartridge and the methylene chloride allowed to evaporate. Purification of the residue on the samplet on a Horizon™ Flash Collector (the Biotage FLASH 25+™ cartridge) using a linear gradient of 5% ethyl acetate-hexane to 100% ethyl acetate gave ethyl 1-{[4-(4-bromophenyl)-1,3-thiazol-2-yl]amino}cyclopropane carboxylate (2.66 g, 36%) as a light yellow solid, mp 152-154° C.; MS m/z 367.

Step 5: (1-{[4-(4-bromophenyl)-1,3-thiazol-2-yl]amino}cyclopropyl)methanol

A solution of ethyl 1-{[4-(4-bromophenyl)-1,3-thiazol-2-yl]amino}cyclopropane carboxylate (3.91 g, 10.6 mmol), prepared in the previous step, in 50 mL of anhydrous tetrahydrofuran was added under nitrogen dropwise to a suspension of lithium aluminum hydride (1.00 g, 26.3 mmol) in 20 mL of anhydrous tetrahydrofuran at ice-bath temperature. After the addition, the cooling bath was removed and the stirring continued for 1 h. Water (1 mL) was slowly added to the reaction, followed by the addition of 1 mL of 15% NaOH and then 3 mL of water. After the additions, the reaction was stirred for 1 h. The reaction was diluted with ethyl acetate and filtered through the Celite™ reagent. The filtrate was extracted two times with water, dried (anhydrous $MgSO_4$), filtered and the solvent removed under reduced pressure to give a crude residue. The residue was taken up in methylene chloride, applied to a Biotage FLASH 40+™ cartridge and the methylene chloride allowed to evaporate. Purification of the residue on the samplet on a Horizon™ Flash Collector (the Biotage FLASH 40+™ cartridge) using a linear gradient of 5% methylene chloride-hexane to 100% methylene chloride gave a material which was recrystallized from methylene chloride to give (1-{[4-(4-bromophenyl)-1,3-thiazol-2-yl] amino}cyclopropyl)methanol (0.4867 g, 14%) as a white solid mp 129-131° C.; MS (ES) m/z 324.9.

Step 6: 4-[4-(4-Bromophenyl)-1,3-thiazol-2-yl]-6-oxa-4-azaspiro[2.4]heptane-5-one A mixture of (1-{[4-(4-bromophenyl)-1,3-thiazol-2-yl] amino}cyclopropyl)methanol (0.7598 g 2.34 mmol), prepared in previous step, and 15 mL of anhydrous acetonitrile were sonicated for 1 min and then stirred on a vortex stirrer for 2 min. To the resulting solution, carbonyldiimidazole (0.5683 g, 3.5 mmol) was added and the mixture again sonicated for 1 min and stirred on a vortex stirrer for 2 min. The resulting solution was then heated in an Emrys™ Optimizer microwave oven at 165° C. for 20 min. Upon cooling to room temperature crystals began to form. The crystals were collected by filtration and the filtrate was concentrated under reduced pressure. The residue was partitioned between methylene chloride and 2N HCl. The organic layer was separated, washed with water, dried over anhydrous $MgSO_4$, filtered and concentrated under reduced pressure. The material obtained was combined with the crystalline material previously isolated to give the title compound (607.9 mg 75%) as a white solid, mp 201-202° C.; MS (ESI) m/z 351. HRMS: calcd for $C_{14}H_{11}BrN_2O_2S+H+$, 350.97973; found (ESI, [M+H]$^+$), 350.9806.

Example 25

4-[2-(5-oxo-6-oxa-4-azaspiro[2.4]hept-4-yl)-1,3-thiazol-4-yl]benzonitrile

In the manner as described in Example 2, replacing (4R)-3-[4-(4-bromophenyl)-1,3-thiazol-2-yl]-4-methyl-1,3-oxazolidin-2-one with 4-[4-(4-bromophenyl)-1,3-thiazol-2-yl]-6-oxa-4-azaspiro[2.4]heptane-5-one (272.8 mg, 0.776 mmol), prepared in the previous step, gave a solid. The solid was taken up in methylene chloride, applied to a Biotage FLASH 25+™ cartridge and the methylene chloride allowed to evaporate. Purification of the residue on the samplet on a Horizon™ Flash Collector (the Biotage FLASH 25+™ cartridge) using a linear gradient of 5% ethyl acetate-hexane to 100% ethyl acetate gave the title compound (173.5 mg, 75%) as a white solid, mp 219-221° C.; MS (ES) m/z 297.9. Anal. Calcd for $C_{15}H_{11}N_3O_2S$: C, 60.59; H, 3.73; N, 14.13. Found: C, 60.38; H, 3.12; N, 13.90.

Example 26

5-[4-(4-Bromophenyl)-1,3-thiazol-2-yl]-7-oxa-5-azaspiro[3.4]octan-6-one

Step 1: Ethyl 1-{[4-(4-bromophenyl)-1,3-thiazol-2-yl]amino}cyclobutane carboxylate Triethylamine (3.30 mL, 23.7 mmol) was added under nitrogen to a mixture of 2-(4-bromophenyl)-2-oxoethyl thiocyanate (5.50 g, 21.6 mmol), prepared in step 1 of Example 1, and ethyl 1-aminocyclobutanecarboxylate hydrochloride (4.24 g, 23.6 mmol) in 130 mL of absolute ethanol. The mixture was then stirred at 68° C. overnight. The reaction was concentrated under reduced pressure to remove the ethanol. The residue was partitioned between ethyl acetate and water. The aqueous layer was made basic by the addition of 2 N NaOH. The organic layer was separated, washed two times with water, dried ($MgSO_4$), filtered and the solvent removed under reduced pressure. Purification of the residue on a Horizon™ Flash Collector (the Biotage FLASH 40+™ cartridge) using a linear gradient of 45% methylene chloride in hexane to 100% methylene chloride as the eluent gave ethyl 1-{[4-(4-bromophenyl)-1,3-thiazol-2-yl]amino}cyclobutane carboxylate (1.0 g, 12%) as a brown oil, MS (ESI) m/z 381 [M+H]$^+$.

Step 2: (1-{[4-(4-Bromophenyl)-1,3-thiazol-2-yl]amino}cyclobutyl)methanol

Lithium aluminum hydride (290 mg, 7.6 mmol) was added under nitrogen in portions to a solution of ethyl 1-{[4-(4-bromophenyl)-1,3-thiazol-2-yl]amino}cyclobutane carboxylate (990 mg, 2.6 mmol), prepared in the previous step, in 15 mL of tetrahydrofuran at ice bath temperature. After the addition, the reaction was stirred at ice bath temperature for 3 h. Water (290 µL) was added dropwise, followed by the addition of 290 µL of 15% NaOH and then 870 µL of water. After the addition, the reaction was stirred for 40 min. The reaction was filtered through the Celite™ reagent and the Celite™ reagent washed with ethyl acetate. The filtrate was partitioned with water. The organic layer was separated, washed one time with water, one time with saturated sodium chloride, dried ($MgSO_4$), filtered and the solvent removed under reduced pressure. Purification of the residue on a Horizon™ Flash Collector (the Biotage FLASH 40+™ cartridge) using a linear gradient of ethyl acetate in methylene chloride gave (1-{[4-(4-bromophenyl)-1,3-thiazol-2-yl]amino}cyclobutyl)methanol (483 mg, 55%) as a light yellow solid, MS (ESI) m/z 339 [M+H]$^+$.

Step 3: 5-[4-(4-Bromophenyl)-1,3-thiazol-2-yl]-7-oxa-5-azaspiro[3.4]octan-6-one

In the same manner as described in step 4 of Example 1, replacing (2R)-2-{[4-(4-bromophenyl)-1,3-thiazol-2-yl]amino}propan-1-ol with (1-{[4-(4-bromophenyl)-1,3-thiazol-2-yl]amino}cyclobutyl)methanol (423.6 mg, 1.25 mmol), prepared in the previous step, gave the title compound (450 mg, 99%) as a white solid, MS (ESI) m/z 365 [M+H]$^+$. Anal. Calcd for $C_{15}H_{13}BrN_2O_2S$: C, 49.33; H, 3.59; N, 7.67. Found: C, 49.26; H, 3.18; N, 7.58.

Example 27

4-[2-(6-Oxo-7-oxa-5-azaspiro[3.4]oct-5-yl)-1,3-thiazol-4-yl]benzonitrile

In the same manner as described in Example 2, replacing (4R)-3-[4-(4-bromophenyl)-1,3-thiazol-2-yl]-4-methyl-1,3-oxazolidin-2-one with 5-[4-(4-bromophenyl)-1,3-thiazol-2-yl]-7-oxa-5-azaspiro[3.4]octan-6-one (410 mg, 1.1 mmol), prepared in step 3 of Example 26, gave 340 mg of a brown solid. Purification of the solid on a Horizon™ Flash Collector (the Biotage FLASH 40+™ cartridge) using a linear gradient of 50% methylene chloride in hexane to 100% methylene chloride gave the title compound (238.2 mg, 70%) as a white solid, MS (ESI) m/z 312 [M+H]$^+$. Anal. Calcd for $C_{16}H_{13}N_3O_2S$: C, 61.72; H, 4.21; N, 13.50. Found: C, 61.53; H, 4.65; N, 13.45.

Examples 28-39 were performed in a similar manner as described in Example 1. In step 3 of Example 1 (R)-(−)-2-amino-1-propanol is replaced with the appropriate amine. After heating at 150° C. for the required period of time, the crude reaction product can be purified in a manner similar to that described in either step 3 of Example 1 or step 1 of Example 20. The purified products are then treated with triphosgene in the same manner as described in step 4 of Example 1. The crude products can be purified in a manner similar to that described in either step 4 of Example 1 or step 2 of Example 20.

Example 28

3-[4-(4-Bromophenyl)-1,3-thiazol-2-yl]-1,3-oxazolidin-2-one mp 197-199° C.; MS (ES) m/z 324.9 [M+H]+.

Example 29

3-[4-(4-Bromophenyl)-1,3-thiazol-2-yl]-4-propyl-1,3-oxazolidin-2-one mp 156-157° C.; MS (ESI) m/z 367 [M+H]+.

Example 30

3-[4-(4-Bromophenyl)-1,3-thiazol-2-yl]-4-butyl-1,3-oxazolidin-2-one mp 153-155° C.; MS (ES) m/z 381.0 [M+H]+.

Example 31

3-[4-(4-Bromophenyl)-1,3-thiazol-2-yl]-5-methyl-1,3-oxazolidin-2-one mp 191-193° C.; MS (ESI) m/z 339 [M+H]+.

Example 32

3-[4-(4-Bromophenyl)-1,3-thiazol-2-yl]-5-ethyl-1,3-oxazolidin-2-one mp 141-142° C.; MS (ES) m/z 352.9 [M+H]+.

Example 33

3-[4-(4-Bromophenyl)-1,3-thiazol-2-yl]-1,3-oxazinan-2-one mp 225-227° C.; MS (ESI) m/z 339 [M+H]+.

Example 34

1-[4-(4-Bromophenyl)-1,3-thiazol-2-yl]-3-oxa-1-azaspiro[4.4]nonan-2-one mp 138-139° C.; MS (ES) m/z 379.0 [M+H]+.

Example 35

(4R)-3-[4-(4-Bromophenyl)-1,3-thiazol-2-yl]-4-phenyl-1,3-oxazolidin-2-one mp 218-220° C.; MS (ES) m/z 401.0 [M+H]+.

Example 36

(4R)-4-Benzyl-3-[4-(4-bromophenyl)-1,3-thiazol-2-yl]-1,3-oxazolidin-2-one mp 177-179° C.; MS m/z 415 [M+H]+.

Example 37

(4S)-3-[4-(4-Bromophenyl)-1,3-thiazol-2-yl]-4-isobutyl-1,3-oxazolidin-2-one mp 144-146° C.; MS m/z 381 [M+H]+.

Example 38

3-[4-(4-Bromophenyl)-1,3-thiazol-2-yl]-4-isopropyl-1,3-oxazolidin-2-one mp 174-176° C.; MS (ES) m/z 366.9 [M+H]+.

Example 39

3-[4-(4-Bromophenyl)-1,3-thiazol-2-yl]-5,5-dimethyl-1,3-oxazinan-2-one mp 169-171° C.; MS (ESI) m/z 367 [M+H]+.

Examples 40-48 were prepared in a similar manner as described in Example 2. The reaction products can be purified in a manner similar to that described in either Example 2 or Example 21.

Example 40

4-[2-(2-Oxo-4-propyl-1,3-oxazolidin-3-yl)-1,3-thiazol-4-yl]benzonitrile mp 132-134° C.; MS (ESI) m/z 314 [M+H]+.

Example 41

4-[2-(5-Methyl-2-oxo-1,3-oxazolidin-3-yl)-1,3-thiazol-4-yl]benzonitrile mp 214-216° C.; MS (ESI) m/z 286 [M+H]+.

Example 42

4-[2-(5-Ethyl-2-oxo-1,3-oxazolidin-3-yl)-1,3-thiazol-4-yl]benzonitrile mp 168-170° C.; MS (ESI) m/z 300 [M+H]+.

Example 43

4-[2-(4-Isopropyl-2-oxo-1,3-oxazolidin-3-yl)-1,3-thiazol-4-yl]benzonitrile mp 126-128° C.; MS (ES) m/z 314.0 [M+H]+.

Example 44

4-{2-[(4R)-4-Benzyl-2-oxo-1,3-oxazolidin-3-yl]-1,3-thiazol-4-yl}benzonitrile mp 174-176° C.; MS (ES) m/z 362.0 [M+H]+.

Example 45

4-{2-[(4R)-2-Oxo-4-phenyl-1,3-oxazolidin-3-yl]-1,3-thiazol-4-yl}benzonitrile mp 243-245° C.; MS (ES) m/z 347.9 [M+H]$^+$.

Example 46

4-{2-[(4S)-2-Oxo-4-phenyl-1,3-oxazolidin-3-yl]-1,3-thiazol-4-yl}benzonitrile mp 242-244° C.; MS (ES) m/z 347.9 [M+H]$^+$.

Example 47

4-[2-(2-Oxo-3-oxa-1-azaspiro[4.4]non-1-yl)-1,3-thiazol-4-yl]benzonitrile mp 196-198° C.; MS (ESI) m/z 326 [M+H]$^+$. Anal. Calcd for $C_{17}H_{15}N_3O_2S$: C, 62.75; H, 4.65; N, 12.91. Found: C, 61.53; H, 4.48; N, 12.38.

Example 48

4-[2-(4-Butyl-2-oxo-1,3-oxazolidin-3-yl)-1,3-thiazol-4-yl]benzonitrile mp 134-137° C.; MS (ESI) m/z 328 [M+H]$^+$. Anal. Calcd for $C_{17}H_{17}N_3O_2S$: C, 62.37; H, 5.23; N, 12.83. Found: C, 62.07; H, 4.61; N, 12.68.

Example 49

3-[4-(4-Bromophenyl)-1,3-thiazol-2-yl]-4-ethyl-1,3-oxazolidin-2-one

Step 1: 2-[4-(4-Bromo-phenyl)-thiazol-2-ylamino]-butan-1-ol

A mixture of 2-bromo-4-(4-bromophenyl)-1,3-thiazole (604 mg, 2.37 mmol), prepared in step 2 of Example 1, and 2-amino-1-butanol (5 mL) was heated to 200° C. for 30 min under microwave irradiation. The cooled reaction mixture was then poured into water (125 mL) and the mixture stirred vigorously for 30 min. The resulting oily suspension was extracted with ethyl acetate, the organic phase washed with water (2×125 mL) and brine (125 mL), dried (anhydrous $MgSO_4$), filtered and the solvent removed under reduced pressure to give a yellow solid (0.78 g). Purification by flash chromatography using a solvent gradient of 0 to 2% methanol in methylene chloride gave a cream solid that was recrystallized from diethyl ether/hexane to give 2-[4-(4-bromophenyl)-thiazol-2-ylamino]-butan-1-ol (405 mg, 65%) as cream needles; mp 94° C.; MS (ESI) m/z 325 [M–H]$^-$. Anal. Calcd for $C_{13}H_{15}BrN_2OS$: C, 47.71; H, 4.62; N, 8.56. Found: C, 48.43; H, 4.57; N, 8.31. HRMS: calcd for $C_{13}H_{15}BrN_2OS+H^+$, 327.01612; found (ESI, [M+H]$^+$), 327.015.

Step 2: 3-[4-(4-Bromophenyl)-1,3-thiazol-2-yl]-4-ethyl-1,3-oxazolidin-2-one

In the same manner as described in step 4 of Example 1, replacing (2R)-2-{[4-(4-bromophenyl)-1,3-thiazol-2-yl]amino}propan-1-ol with 2-[4-(4-bromo-phenyl)-thiazol-2-ylamino]-butan-1-ol, prepared in the previous step, and purification by flash chromatography using a solvent gradient of 10 to 20% ethyl acetate in hexane gave the title compound (155 mg, 72%) as a white solid; mp 148.5° C.; MS (ESI) m/z 353 [M+H]$^+$. Anal. Calcd for $C_{14}H_{13}BrN_2O_2S$: C, 47.60; H, 3.71; N, 7.93. Found: C, 47.25; H, 3.64; N, 7.74. HRMS: calcd for $C_{14}H_{13}BrN_2O_2S+H^+$, 352.99538; found (ESI, [M+H]$^+$), 352.9939.

Example 50

3-[4-(4-Bromophenyl)-1,3-thiazol-2-yl]-4-methyl-1,3-oxazolidin-2-one

Step 1: 2-{[4-(4-Bromophenyl)-1,3-thiazol-2-yl]amino}propan-1-ol

In the same manner as described in step 1 of Example 49, replacing 2-amino-1-butanol with 2-amino-1-propanol and purification by flash chromatography using a solvent gradient of 0 to 2% methanol in methylene chloride gave 2-{[4-(4-bromophenyl)-1,3-thiazol-2-yl]amino}propan-1-ol (495 mg, 84%) as a white solid; mp 100-101° C.; MS (ESI) m/z 313 [M+H]$^+$. Anal. Calcd for $C_{12}H_{13}BrN_2OS$: C, 46.02; H, 4.18; N, 8.94. Found: C, 46.05; H, 3.96; N, 8.83. HRMS: calcd for $C_{12}H_{13}BrN_2OS-H^+$, 310.98592; found (ESI, [M–H]$^-$), 310.9861.

Step 2: 3-[4-(4-Bromophenyl)-1,3-thiazol-2-yl]-4-methyl-1,3-oxazolidin-2-one In the same manner as described in step 4 of Example 1, replacing (2R)-2-{[4-(4-bromophenyl)-1,3-thiazol-2-yl]amino}propan-1-ol with 2-{[4-(4-bromophenyl)-1,3-thiazol-2-yl]amino}propan-1-ol, prepared in the previous step, and purification by flash chromatography using a solvent gradient of 10 to 30% ethyl acetate in hexane gave the title compound (293 mg, 64%) as a white solid; mp 189-190° C.; MS (ESI) m/z 339 [M+H]$^+$. Anal. Calcd for $C_{13}H_{11}BrN_2O_2S$: C, 46.03; H, 3.27; N, 8.26. Found: C, 45.83; H, 3.25; N, 8.07. HRMS: calcd for $C_{13}H_{11}BrN_2O_2S+H^+$, 338.97973; found (ESI, [M+H]$^+$), 338.9784.

Example 51

4-[2-(4-Methyl-2-oxo-1,3-oxazolidin-3-yl)-1,3-thiazol-4-yl]benzonitrile

In the same manner as described in Example 2, replacing (4R)-3-[4-(4-bromophenyl)-1,3-thiazol-2-yl]-4-methyl-1,3-oxazolidin-2-one with 3-[4-(4-bromophenyl)-1,3-thiazol-2-yl]-4-methyl-1,3-oxazolidin-2-one, prepared in step 2 of Example 50, and purification by flash chromatography using a solvent gradient of 10 to 50% ethyl acetate in hexane gave the title compound (91 mg, 86%) as a white solid, mp 215-216° C.; MS (ESI) m/z 286 [M+H]$^+$. Anal. Calcd for $C_{14}H_{11}N_3O_2S$: C, 58.93; H, 3.89; N, 14.73. Found: C, 57.68; H, 3.66; N, 14.24. HRMS: calcd for $C_{14}H_{11}N_3O_2S+H^+$, 286.06502; found (ESI, [M+H]$^+$), 286.0643.

Example 52

3-[2-(4,4-dimethyl-2-oxo-1,3-oxazolidin-3-yl)-1,3-thiazol-4-yl]benzonitrile

Step 1: N-({[1-Methyl-1-(hydroxymethyl)ethyl]amino}carbonothioyl)benzamide

In the same manner as described in step 4 of Example 19, replacing 2-amino-2-ethylbutan-1-ol with 2-amino-2-methyl-1-propanol, gave N-({[1-methyl-1-(hydroxymethyl)ethyl]amino}carbonothioyl)benzamide (13.40 g, 100%) as an off-white solid, mp 116-118° C., MS (ES) m/z 253 [M+H]$^+$.

Step 2: N-(2-Hydroxy-1,1-dimethylethyl)thiourea

A solution of N-({[1-methyl-1-(hydroxymethyl)ethyl]amino}carbonothioyl)benzamide (12.00 g, 47.6 mmol), prepared in the previous step, and 1 M LiOH (57.1 mL, 57.1 mmol) in 400 mL of tetrahydrofuran plus 400 mL of methanol plus 200 mL of water was stirred under nitrogen at room temperature for 16 h. The reaction was concentrated under reduced pressure to remove most of the tetrahydrofuran and methanol. The residual aqueous layer was extracted multiple times with 20% methanol in methylene chloride. The combined extracts were dried (MgSO$_4$), filtered and the solvent removed under reduced pressure to give 4.91 g of a brown solid. Recrystallization of the solid from ethyl acetate gave N-(2-hydroxy-1,1-dimethylethyl)thiourea (2.562 g, 36%) as a white solid, mp 127-129° C.; MS (ES) m/z 149 [M+H]$^+$.

Step 3: 3-{2-[(2-Hydroxy-1,1-dimethylethyl)amino]-1,3-thiazol-4-yl}benzonitrile A suspension of 3-(2-bromoacetyl)benzonitrile (809.0 mg, 3.61 mmol) in 50 mL of absolute ethanol was warmed to dissolve all of the solid. N-(2-hydroxy-1,1-dimethylethyl)thiourea (534.4 mg, 3.61 mmol), prepared in the previous step, was added and the reaction refluxed under nitrogen for 4 h. The reaction was concentrated under reduced pressure to remove the ethanol and the residue was dissolved in 10% methanol in methylene chloride and then extracted with 5% NaHCO$_3$. The aqueous layer was separated and extracted three times with 10% methanol in methylene chloride. The combined extracts were dried (MgSO$_4$) and the solvent removed under reduced pressure to give 981.1 mg of a yellow foam. Purification of the foam on 300 g of silica gel (230-400 mesh) using 20% ethyl acetate in methylene chloride as the eluent gave 3-{2-[(2-hydroxy-1,1-dimethylethyl)amino]-1,3-thiazol-4-yl}benzonitrile (854.0 mg, 87%) as a yellow solid, mp 124-126° C.; MS (ESI) m/z 274 [M+H]$^+$.

Step 4: 3-[2-(4,4-Dimethyl-2-oxo-1,3-oxazolidin-3-yl)-1,3-thiazol-4-yl]benzonitrile In the same manner as described in step 4 of Example 1, replacing (2R)-2-{[4-(4-bromophenyl)-1,3-thiazol-2-yl]amino}propan-1-ol with 3-{2-[(2-hydroxy-1,1-dimethylethyl)amino]-1,3-thiazol-4-yl}benzonitrile, prepared in the previous step, gave 911.5 mg of a light tan solid. Purification of the solid on 300 g of silica gel (230-400 mesh) using methylene chloride as the eluent gave the title compound (783.2 mg, 92%) as a white solid, mp 181-183° C.; MS (ES) m/z 300.0 [M+H]$^+$. Anal. Calcd for C$_{15}$H$_{13}$N$_3$O$_2$S: C, 60.19; H, 4.38; N, 14.04. Found: C, 60.11; H, 3.99; N, 13.95.

Example 53

4-[2-(4,4-Diethyl-2-oxo-1,3-oxazolidin-3-yl)-5-fluoro-1,3-thiazol-4-yl]benzonitrile In the same manner as described in Example 11, and replacing (4S)-3-[4-(4-bromophenyl)-1,3-thiazol-2-yl]-4-ethyl-1,3-oxazolidin-2-one with 4-[2-(4,4-diethyl-2-oxo-1,3-oxazolidin-3-yl)-1,3-thiazol-4-yl]benzonitrile, prepared in step 7 of Example 19, gave 1.1502 g of a white solid. Purification of the solid on 600 g of silica gel (230-400 mesh) using 50% hexane in methylene chloride to 100% methylene chloride gave the title compound (428.3 mg, 28%) as a white solid, mp 151-153° C.; MS (ESI) m/z 346 [M+H]$^+$. Anal. Calcd for C$_{17}$H$_{16}$FN$_3$O$_2$S: C, 59.12; H, 4.67; N, 12.17. Found: C, 59.22; H, 4.62; N, 12.20.

Example 54

4-[2-(2-Oxo-1,3-benzoxazol-3(2H)-yl)-1,3-thiazol-4-yl]benzonitrile

Step 1: 4-{2-[(2-Hydroxyphenyl)amino]-1,3-thiazol-4-yl}benzonitrile

2-Bromo-4'-cyano-acetophone (1.009 g, 4.50 mmol) was suspended in 25 mL of absolute ethanol and the mixture heated under nitrogen to 70° C., at which time the solid dissolved. 2-Hydroxyphenylthiourea (750.4 mg, 4.46 mmol) was added at 70° C. The solid appeared to completely dissolve and then within a few minutes a large amount of solid precipitated from the reaction. The mixture was then refluxed for 2 h. The solid was collected by filtration, rinsed with absolute ethanol and dried under reduced pressure to give 4-{2-[(2-hydroxyphenyl)amino]-1,3-thiazol-4-yl}benzonitrile (1.174 g, 89%) as a greenish-white solid, mp 278-280° C.; MS (ES) m/z 291.8 [M−H]$^-$.

Step 2: 4-[2-(2-Oxo-1,3-benzoxazol-3(2H)-yl)-1,3-thiazol-4-yl]benzonitrile

In the same manner as described in step 4 of Example 1, replacing (2R)-2-{[4-(4-bromophenyl)-1,3-thiazol-2-yl]amino}propan-1-ol with 4-{2-[(2-hydroxyphenyl)amino]-1,3-thiazol-4-yl}benzonitrile, prepared in the previous step, and purification of the residue on a Horizon™ Flash Collector (the Biotage FLASH 25+™ cartridge) using a linear gradient of hexane in methylene-chloride as the eluent gave the title compound (924.3 mg, 78%) as a white solid, mp 244-245° C.; MS m/z 320 [M−H]$^-$.

Example 55

4-[5-Fluoro-2-(5-oxo-6-oxa-4-azaspiro[2.4]hept-4-yl)-1,3-thiazol-4-yl]benzonitrile In the same manner as described in Example 11, and replacing (4S)-3-[4-(4-bromophenyl)-1,3-thiazol-2-yl]-4-ethyl-1,3-oxazolidin-2-one with 4-[2-(5-oxo-6-oxa-4-azaspiro[2.4]hept-4-yl)-1,3-thiazol-4-yl]benzonitrile, prepared in Example 25, gave a white solid. Purification of the solid on a Horizon™ Flash Collector (the Biotage FLASH 40+™ cartridge) using a linear gradient of hexane in methylene-chloride as the eluent gave the title compound (102.1 mg, 37%) as a white solid, mp 222-224° C.; MS (APCI) m/z 316; Anal. Calcd for C$_{15}$H$_{10}$FN$_3$O$_2$S: C, 57.14; H, 3.20; N, 13.33. Found: C, 56.69; H, 2.83; N, 13.04.

Example 56

3-[4-(4-Bromophenyl)-5-methyl-1,3-thiazol-2-yl]-4,4-dimethyl-1,3-oxazolidin-2-one

Step 1: 2-{[4-(4-Bromophenyl)-5-methyl-1,3-thiazol-2-yl]amino}-2-methylpropan-1-ol hydrobromide A mixture of 2,4'-dibromopropiophenone (3.940 g, 13.5 mmol) and N-(2-hydroxy-1,1-dimethylethyl)thiourea (2.000 g, 13.5 mmol), prepared in step 2 of Example 52, in 80 mL of absolute ethanol was refluxed under nitrogen for 3 h. The solvent was removed under reduced pressure to give 2-{[4-(4-bromophenyl)-5-methyl-1,3-thiazol-2-yl]amino}-2-methylpropan-1-ol hydrobromide (5.717 g, 100%) as a tan oil, MS (ESI) m/z 341.

Step 2: 3-[4-(4-bromophenyl)-5-methyl-1,3-thiazol-2-yl]-4,4-dimethyl-1,3-oxazolidin-2-one Diisopropylethylamine (10.0 mL, 57.4 mmol) was added under nitrogen to a mixture of 2-{[4-(4-bromophenyl)-5-methyl-1,3-thiazol-2-yl]amino}-2-methylpropan-1-ol hydrobromide (5.2 g, 1.2 mmol), prepared in the previous step, and 120 mL of methylene chloride at room temperature. A white solid formed. The mixture was cooled to ice bath temperature and triphosgene (5.2 g, 1.8 mmol) in 60 mL of methylene chloride was added dropwise over approximately 2 h. After the addition, the reaction became homogeneous. The reaction was stirred at ice bath temperature for approximately 2 h and then at room temperature overnight. The reaction was extracted with aqueous sodium hydroxide and the solvent removed under reduced pressure to give 5.6 g of a solid. Purification of the solid on a Horizon™ Flash Collector (the Biotage FLASH 25+™ cartridge) using a linear gradient of 36% methylene chloride in hexane to 75% methylene chloride in hexane gave the title compound (2.77 g, 63%) as a white solid, mp 175-176.5° C.; MS (ESI) m/z 367 [M+H]$^+$. Anal. Calcd for $C_{15}H_{15}BrN_2O_2S$: C, 49.06; H, 4.12; N, 7.63. Found: C, 48.94; H, 4.19; N, 7.56.

Example 57

4-[2-(4,4-Dimethyl-2-oxo-1,3-oxazolidin-3-yl)-5-methyl-1,3-thiazol-4-yl]benzonitrile In the same manner as described in Example 2, replacing (4R)-3-[4-(4-bromophenyl)-1,3-thiazol-2-yl]-4-methyl-1,3-oxazolidin-2-one with 3-[4-(4-bromophenyl)-5-methyl-1,3-thiazol-2-yl]-4,4-dimethyl-1,3-oxazolidin-2-one (1.23 g, 3.35 mmol), prepared in step 2 of Example 56, gave a solid. Purification of the solid on a Horizon™ Flash Collector (the Biotage FLASH 25+™ cartridge) using a linear gradient of 30% methylene chloride in hexane to 80% methylene chloride in hexane as the eluent gave the title compound (730 mg, 70%) as a white solid, mp 192.5-193° C.; MS (ESI) m/z 314 [M+H]$^+$. Anal. Calcd for $C_{16}H_{15}N_3O_2S$: C, 61.32; H, 4.82; N, 13.41. Found: C, 60.93; H, 4.99; N, 13.23.

Example 58

4-[2-(4,4-dimethyl-2-oxo-1,3-oxazolidin-3-yl)-5-fluoro-1,3-thiazol-4-yl]benzonitrile The Selectfluor® reagent (2.042 g, 5.76 mmol) in 250 mL of acetonitrile was added under nitrogen dropwise to a solution of 4-[2-(4,4-dimethyl-2-oxo-1,3-oxazolidin-3-yl)-1,3-thiazol-4-yl]benzonitrile (1.566 g, 5.23 mmol), prepared in Example 6, in 250 mL of acetonitrile at room temperature. After the addition, the reaction was stirred at room temperature overnight. The reaction was concentrated under reduced pressure to remove the acetonitrile. The residue was partitioned between ethyl acetate and water. The organic layer was separated, washed once with water, and the solvent removed under reduced pressure. Purification of the residue on a Horizon™ Flash Collector (the Biotage FLASH 25+™ cartridge) using a linear gradient of methylene chloride in hexane as the eluent gave the title compound (566.7 mg, 34%) as a white solid, mp 177-178° C.; MS (ESI) m/z 318 [M+H]$^+$. Anal. Calcd for $C_{15}H_{12}FN_3O_2S$: C, 56.77; H, 3.81; N, 13.24. Found: C, 56.53; H, 3.91; N, 13.12.

Example 59

4-Bromo-5-[2-(4,4-dimethyl-2-oxo-1,3-oxazolidin-3-yl)-1,3-thiazol-4-yl]thiophene-2-carbonitrile

Step 1: 4-Bromo-5-(chloroacetyl)thiophene-2-carbonitrile

Butyllithium (2.5 M solution in hexanes; 14.5 mL, 36.3 mmol) was added under nitrogen over approximately 5 min to a solution of 4-bromo-thiophene-2-carbonitrile (5.95 g, 31.6 mmol) in 300 mL of anhydrous tetrahydrofuran at dry ice-acetone temperature. After the addition, the reaction was stirred at dry ice-acetone temperature for 30 min. 2-Chloro-N-methoxy-N-methyl acetamide (4.80 g, 32.7 mmol) in 40 mL of anhydrous tetrahydrofuran was then added dropwise over 30 min. After the addition, the reaction was stirred at dry ice-acetone temperature for 4 h. 6 M HCl (36 mL) was added and the reaction allowed to warm to room temperature. The reaction was concentrated under reduced pressure to remove the tetrahydrofuran. The residue was partitioned between ethyl acetate and water. Saturated sodium chloride was added to aid in the separation of an emulsion. The organic layer was separated, washed with water, saturated sodium chloride, dried ($MgSO_4$), filtered and the solvent removed under reduced pressure. The residue was purified on 800 g of silica gel (230-400 mesh) using a gradient of 30% methylene chloride in hexane to 60% methylene chloride in hexane as the eluent. Isolation of the major component gave 4-bromo-5-(chloroacetyl)thiophene-2-carbonitrile (1.81 g, 22%) as a white solid, mp 126-128° C.; MS (ESI) m/z 262.

Isolation of a minor component gave 4-(chloroacetyl)thiophene-2-carbonitrile (1.02 g, 17%) as a light yellow solid, mp 94-98° C.; MS (ESI) m/z 184.

Step 2: 4-Bromo-5-{2-[(2-hydroxy-1,1-dimethylethyl)amino]-1,3-thiazol-4-yl}thiophene-2-carbonitrile hydrochloride A mixture of 4-bromo-5-(chloroacetyl)thiophene-2-carbonitrile (430 mg, 1.6 mmol), prepared in the previous step, and N-(2-hydroxy-1,1-dimethylethyl)thiourea (241.2 mg, 1.6 mmol), prepared in step 2 of Example 52, in 10 mL of absolute ethanol was refluxed under nitrogen for 2.5 h. The solvent was concentrated to approximately two thirds its volume. The solid present was collected by filtration and dried under reduced pressure to give 4-bromo-5-{2-[(2-hydroxy-1,1-dimethylethyl)amino]-1,3-thiazol-4-yl}thiophene-2-carbonitrile hydrochloride (367.8 mg, 58%) as a yellow solid, mp 177.5-178.5° C.; MS (ESI) m/z 358 [M+H]$^+$.

Step 3: 4-Bromo-5-[2-(4,4-dimethyl-2-oxo-1,3-oxazolidin-3-yl)-1,3-thiazol-4-yl]thiophene-2-carbonitrile In the same manner as described in step 2 of Example 56 and replacing 2-{[4-(4-bromophenyl)-5-methyl-1,3-thiazol-2-yl]amino}-2-methylpropan-1-ol hydrobromide with 4-bromo-5-{2-[(2-hydroxy-1,1-dimethylethyl)amino]-1,3-thiazol-4-yl}thiophene-2-carbonitrile hydrochloride (550 mg, 1.3 mmol), prepared in the previous step, gave the title compound (250 mg, 50%) as a light yellow solid, mp 230-234° C.; MS (ESI) m/z 384 [M+H]$^+$. Anal. Calcd for $C_{13}H_{10}BrN_3O_2S_2$: C, 40.63; H, 2.62; N, 10.93. Found: C, 40.53; H, 1.82; N, 10.61.

Example 60

5-[2-(4,4-dimethyl-2-oxo-1,3-oxazolidin-3-yl)-1,3-thiazol-4-yl]thiophene-2-carbonitrile A mixture of 4-bromo-5-[2-(4,4-dimethyl-2-oxo-1,3-oxazolidin-3-yl)-1,3-thiazol-4-yl]thiophene-2-carbonitrile (380 mg, 0.99 mmol), prepared in step 3 of Example 59, and 10% Pd (410 mg) on carbon in 25 mL of ethanol was hydrogenated under a balloon atmosphere of hydrogen for one day. The reaction was filtered through the Celite™ reagent and the filtrate concentrated under reduced pressure to give 130 mg of a yellow solid. The Celite™ reagent was then rinsed with 100 mL of 20% methanol in methylene chloride followed by 20 mL of ammonium hydroxide. The filtrates were concentrated under reduced pressure and the residue combined with the 130 mg of yellow solid. Purification of the residue on a Horizon™ Flash Collector (the Biotage FLASH 40+™ cartridge) using a linear gradient of 100% hexane to 40% methylene chloride in hexane as the eluent gave the title compound (69.7 mg, 23%) as a white solid, mp 250-251° C.; MS (ESI) m/z 306 [M+H]$^+$. Anal. Calcd for $C_{13}H_{11}N_3O_2S_2 \cdot 0.10\ CH_2Cl_2$: C, 50.13; H, 3.60; N, 13.39. Found: C, 49.86; H, 3.61; N, 13.01.

Example 61

4-[2-(4,4-Dimethyl-2-oxo-1,3-oxazolidin-3-yl)-1,3-thiazol-4-yl]thiophene-2-carbonitrile

Step 1: 4-{2-[(2-Hydroxy-1,1-dimethylethyl)amino]-1,3-thiazol-4-yl}thiophene-2-carbonitrile hydrochloride A mixture of 4-(chloroacetyl)thiophene-2-carbonitrile (500.5 mg, 2.73 mmol), prepared in step 1 of Example 59, and N-(2-hydroxy-1,1-dimethylethyl)thiourea (399.4 mg, 2.69 mmol), prepared in step 2 of Example 52, in 20 mL of ethanol was stirred under nitrogen at room temperature overnight. The solid was collected by filtration and dried under reduced pressure to give 4-{2-[(2-hydroxy-1,1-dimethylethyl)amino]-1,3-thiazol-4-yl}thiophene-2-carbonitrile hydrochloride (738.1 mg, 86%) as a light tan solid, mp 197-201° C.; MS (ES) m/z 277.9 [M–H]$^-$.

Step 2: 4-[2-(4,4-Dimethyl-2-oxo-1,3-oxazolidin-3-yl)-1,3-thiazol-4-yl]thiophene-2-carbonitrile In the same manner as described in step 2 of Example 56 and replacing 2-{[4-(4-bromophenyl)-5-methyl-1,3-thiazol-2-yl]amino}-2-methylpropan-1-ol hydrobromide with 4-{2-[(2-hydroxy-1,1-dimethylethyl)amino]-1,3-thiazol-4-yl}thiophene-2-carbonitrile hydrochloride (556.0 mg, 1.54 mmol), prepared in the previous step, gave the title compound (458.9 mg, 85%) as a white solid, mp 249-251.5° C.; MS (ESI) m/z 306 [M+H]$^+$.

Example 62

4-[2-(4,4,5-Trimethyl-2-oxo-1,3-oxazolidin-3-yl)-1,3-thiazol-4-yl]benzonitrile

Step 1: N-{[(2-hydroxy-1,1-dimethylpropyl)amino]carbonothioyl}benzamide

3-Amino-3-methyl-butan-2-ol (5.39 g, 52.2 mmol) in 30 mL of tetrahydrofuran was added under nitrogen over approximately 1 min to a solution of benzoyl isothiocyanate (8.40 g, 51.5 mmol) in 60 mL of tetrahydrofuran at room temperature. After the addition, the reaction was refluxed for 1 h. Concentration of the reaction under reduced pressure gave 14.42 g of a yellow solid. Purification of the solid on 1.1 Kg of silica gel (230-400 mesh) using a gradient of 15% hexane in methylene chloride to 12% ethyl acetate in methylene chloride gave N-{[(2-hydroxy-1,1-dimethylpropyl)amino]carbonothioyl}benzamide (8.59 g, 63%) as an off-white solid, mp 136-138° C.; MS (ESI) m/z 267 [M+H]$^+$.

Step 2: N-(2-hydroxy-1,1-dimethylpropyl)thiourea

Lithium hydroxide (759.1 mg, 31.7 mmol) in 30 mL of water was added under nitrogen to a solution of N-{[(2-hydroxy-1,1-dimethylpropyl)amino]carbonothioyl}benzamide (8.44 g, 31.7 mmol), prepared in the previous step, in 55 mL of tetrahydrofuran at room temperature. After the addition, the reaction was refluxed for 2 h. The reaction was concentrated under reduced pressure to remove the tetrahydrofuran. The residue was partitioned between ethyl acetate and water. The aqueous layer was separated, saturated with sodium chloride and extracted with ethyl acetate. The extracts were combined and the solvent removed under reduced pressure to give 4.89 g of a yellow gel like solid. Purification of the solid on a Horizon™ Flash Collector (the Biotage FLASH 40+™ cartridge) using a linear gradient of ethyl acetate in methylene chloride as the eluent gave N-(2-hydroxy-1,1-dimethylpropyl)thiourea (0.95 g, 18%) as a white solid, mp 148-151° C.; MS (ES) m/z 160.9 [M–H]$^-$.

Step 3: 4-{2-[(2-hydroxy-1,1-dimethylpropyl)amino]-1,3-thiazol-4-yl}benzonitrile hydrobromide A mixture of N-(2-hydroxy-1,1-dimethylpropyl)thiourea (720 mg, 4.4 mmol), prepared in the previous step, and 2-bromo-4'-cyano-acetophenone (980 mg, 4.4 mmol) in 20 mL of ethanol was heated under nitrogen to dissolve all of the solids. The reaction was allowed to come to room temperature and then stirred at room temperature overnight. The solid was collected by filtration and dried under reduced pressure to give 4-{2-[(2-hydroxy-1,1-dimethylpropyl)amino]-1,3-thiazol-4-yl}benzonitrile hydrobromide (1.3157 g, 81%) as a white solid, mp 208-210° C.; MS (ES) m/z 286.0 [M–H]$^-$.

Step 4: 4-[2-(4,4,5-Trimethyl-2-oxo-1,3-oxazolidin-3-yl)-1,3-thiazol-4-yl]benzonitrile In the manner as described in step 2 of Example 56, and replacing 2-{[4-(4-bromophenyl)-5-methyl-1,3-thiazol-2-yl]amino}-2-methylpropan-1-ol hydrobromide with 4-{2-[(2-hydroxy-1,1-dimethylpropyl)amino]-1,3-thiazol-4-yl}benzonitrile hydrobromide (1.07 g, 2.91 mmol), prepared in the previous step, gave the title compound (690 mg, 76%) as a white solid, mp 166-167° C.; MS (ESI) m/z 314 [M+H]$^+$.

Example 63

4-[2-(2-imino-4,4-dimethyl-1,3-oxazolidin-3-yl)-1,3-thiazol-4-yl]benzonitrile A mixture of 4-{2-[(2-hydroxy-1,1-dimethylethyl)amino]-1,3-thiazol-4-yl}benzonitrile (2.00 g, 7.31 mmol), prepared in the same manner as described in step 3 of Example 52, and replacing 3-(2-bromoacetyl)benzonitrile with 4-(2-bromoacetyl)benzonitrile, and C-(di-imidazol-1-yl)-methyleneamine (1.30 g, 8.07 mmol) in 35 mL of tetrahydrofuran was refluxed under nitrogen for three days. The reaction was concentrated under reduced pressure to remove the tetrahydrofuran. The residue was partitioned between methylene chloride and water. The organic layer was separated, dried (MgSO$_4$), filtered and the solvent removed under reduced pressure. Purification of the residue on a Horizon™ Flash Collector (the Biotage FLASH 40+™ cartridge) using a linear gradient of hexane in methylene chloride as the eluent gave the title compound (417.2 mg, 19%) as an off-white solid, mp 158-161° C.; MS (ES) m/z 299.0 [M+H]$^+$. Anal. Calcd for $C_{15}H_{14}N_4OS$: C, 60.38; H, 4.73; N, 18.78. Found: C, 60.38; H, 4.82; N, 18.67.

Example 64

3-[4-(4-Bromophenyl)-1,3-thiazol-2-yl]-4-(trifluoromethyl)-1,3-oxazolidin-2-one

Step 1: Methyl N-[4-(4-bromophenyl)-1,3-thiazol-2-yl]-3,3,3-trifluoroalaninate 4-(4-Bromophenyl)-1,3-thiazol-2-ylamine (510 mg, 2.0 mmol) and methyl-3,3,3-trifluoropyruvate (0.10 mL, 1.0 mmol) were dissolved in 50 mL methylene chloride. Titanium (IV) chloride (1M in toluene, 1.6 mL, 1.6 mmol) was added dropwise to give an orange-brown suspension. The mixture was stirred for 15 min and then added by cannula to a solution of sodium cyanoborohydride (0.26 g, 3.0 mmol) in 50 mL of methanol. The mixture was stirred for 15 min and then quenched by the addition of $H_2O$ and saturated aqueous sodium bicarbonate. The mixture was extracted three times with methylene chloride. The organics were combined, washed with water, brine, dried over anhydrous $MgSO_4$, filtered and concentrated under reduced pressure. Flash chromatography (100% methylene chloride) afforded methyl N-[4-(4-bromophenyl)-1,3-thiazol-2-yl]-3,3,3-trifluoroalaninate (0.17 g, 44%) as a white solid. MS (ES) m/z 392.8. HRMS: calcd for $C_{13}H_{10}BrF_3N_2O_2S+H$, 394.96767; found (ESI, [M+H]$^+$), 394.9671. Analytical HPLC: retention time 10.8 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Step 2: 2-{[4-(4-Bromophenyl)-1,3-thiazol-2-yl] amino}-3,3,3-trifluoropropan-1-ol Methyl N-[4-(4-bromophenyl)-1,3-thiazol-2-yl]-3,3,3-trifluoroalaninate (1.08 g, 2.70 mmol), prepared in the previous step, was dissolved in 50 mL of tetrahydrofuran and cooled to 0° C. Lithium aluminum hydride (1M solution in tetrahydrofuran, 5.5 mL, 5.5 mmol) was added slowly and the mixture was stirred for 30 min. The reaction was then quenched by careful addition of 0.2 mL $H_2O$, followed by 0.2 mL of 15% aqueous KOH, then an additional 0.6 mL of $H_2O$ and the mixture was stirred for 30 min. The reaction mixture was diluted with ethyl acetate and filtered through the Celite™ reagent. The filtrate was washed with brine, dried over anhydrous $MgSO_4$, filtered and concentrated under reduced pressure. Flash chromatography (15% acetone/hexane) provided 2-{[4-(4-bromophenyl)-1,3-thiazol-2-yl]amino}-3,3,3-trifluoropropan-1-ol (0.67 g, 68%) as a white solid, mp 133-134° C.; MS (ESI) m/z 367. HRMS: calcd for $C_{12}H_{10}BrF_3N_2OS+H$, 366.97275; found (ESI, [M+H]$^+$), 366.9712. Analytical HPLC: retention time 10.0 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Step 3: 3-[4-(4-Bromophenyl)-1,3-thiazol-2-yl]-4-(trifluoromethyl)-1,3-oxazolidin-2-one 2-{[4-(4-Bromophenyl)-1,3-thiazol-2-yl]amino}-3,3,3-trifluoropropan-1-ol (0.61 g, 1.6 mmol), prepared in the previous step, was dissolved in 48 mL methylene chloride. Triethylamine (2.2 mL, 16 mmol) was added and the solution was cooled to 0° C. Triphosgene (1.20 g, 4.15 mmol) was added in two portions and the mixture was stirred at 0° C. for 45 min and then at 25° C. for 2 h. The mixture was poured into 250 mL of saturated aqueous sodium bicarbonate and the layers were separated. The organics were washed with water, brine, dried over anhydrous $MgSO_4$, filtered and concentrated under reduced pressure. Flash chromatography (gradient 2% acetone/hexane to 10% acetone/hexane) afforded the title compound (0.47 g, 75%) as a white solid, mp 154-156° C. HRMS: calcd for $C_{13}H_8BrF_3N_2O_2S+H$, 392.95202; found (ESI, [M+H]$^+$), 392.9518. Analytical HPLC: retention time 10.6 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min 1.2 mL/min 5 μL injection.

Example 65

4-{2-[(4S)-2-Oxo-4-(trifluoromethyl)-1,3-oxazolidin-3-yl]-1,3-thiazol-4-yl}benzonitrile 3-[4-(4-Bromophenyl)-1,3-thiazol-2-yl]-4-(trifluoromethyl)-1,3-oxazolidin-2-one, prepared in step 3 of Example 64, (0.455 g, 1.15 mmol) and zinc cyanide (81 mg, 0.69 mmol) were dissolved in 12 mL of DMF. The mixture was purged with nitrogen for 15 min and then tetrakis(triphenylphosphine)palladium(0) (66.5 mg, 0.058 mmol) was added and the mixture was heated to 120° C. for 1.5 h. The mixture was cooled and diluted with ethyl acetate and poured into 200 mL of water. The mixture was extracted with ethyl acetate, the organics were combined, washed with water, brine, dried over anhydrous $MgSO_4$, filtered and concentrated under reduced pressure. Flash chromatography (gradient 1% acetone/hexane to 10% acetone/hexane) afforded racemic 4-{2-[2-oxo-4-(trifluoromethyl)-1,3-oxazolidin-3-yl]-1,3-thiazol-4-yl}benzonitrile (278 mg, 72%) as a white solid.

The racemic mixture was resolved by preparative chiral HPLC:

| | |
|---|---|
| Instrumentation: | the Berger MultiGram SFC ® unit (Berger Instruments, Inc. Newark, DE, USA) |
| Chemicals: | Carbon dioxide (SFC grade) was from BOC Gases (Murray Hill, NJ, USA); Acetonitrile was HPLC-grade from Mallinckrodt Baker (Muskegon, MI, USA) |
| Column: | the Chiralcel ® OJ-H column, 25 cm L × 20 mm ID, 5 μm particle size (Chiral Technologies Corp, Exton, PA, USA) |
| Temperature: | 35° C. (isothermal) |
| Outlet Pressure: | 100 bar |
| Mobile Phase: | 40% acetonitrile in $CO_2$ |
| Flow rate: | 50 mL/min |
| Detection: | UV at 298 nm |
| Solvent: | 100% acetonitrile |

Chiral separation provided 0.12 g of the title compound as a white solid, mp 208-209° C. HRMS: calcd for $C_{14}H_8F_3N_3O_2S+H^+$, 340.03621; found (ESI, [M+H]$^+$), 340.0382. Analytical HPLC: retention time 9.5 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Example 66

4-{2-[(4R)-2-oxo-4-(trifluoromethyl)-1,3-oxazolidin-3-yl]-1,3-thiazol-4-yl}benzonitrile Isolation of the second component in the chiral separation from Example 65 provided 0.12 g of the title compound as a white solid, mp 208-209° C.
HRMS: calcd for $C_{14}H_8F_3N_3O_2S+H^+$, 340.0357; found (ESI, [M+H]$^+$), 340.0382. Analytical HPLC: retention time 9.5 min, 210-370 nm the Xterra® RP18 column, 3.5%, 150× 4.6 mm 40° C. 85/15-5/95 (Ammon. Form. Buff. pH=3.5/ACN+MeOH) for 10 min, hold 4 min, 1.2 mL/min 5 μL injection.

Example 67

3-[4-(4-Bromophenyl)-1,3-thiazol-2-yl]-4-(2,2,2-trifluoroethyl)-1,3-oxazolidin-2-one

Step 1: Methyl 2-{[4-(4-bromophenyl)-1,3-thiazol-2-yl]amino}-4,4,4-trifluorobutanoate 2-Amino-4,4,4-trifluoro-butyric acid methyl ester hydrochloride (1.1 g, 5.3 mmol) was dissolved in 30 mL of ethanol and 2-(4-bromophenyl)-2-oxoethyl thiocyanate, prepared in step 1 of Example 1, (1.23 g, 4.8 mmol) was added followed by triethylamine (0.73 mL, 5.3 mmol). The mixture was heated to 55° C. for 18 h then cooled and concentrated under reduced pressure. Flash chromatography (5% acetone/hexane) afforded methyl 2-{[4-(4-bromophenyl)-1,3-thiazol-2-yl]amino}-4,4,4-trifluorobutanoate (1.21 g, 56%) as a white solid. mp 113-114° C. HRMS: calcd for $C_{14}H_{12}BrF_3N_2O_2S+H^+$, 408.98277; found (ESI, [M+H]$^+$), 408.9831. Analytical HPLC: retention time 11.5 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Step 2: 2-{[4-(4-Bromophenyl)-1,3-thiazol-2-yl]amino}-4,4,4-trifluorobutan-1-ol Methyl 2-{[4-(4-bromophenyl)-1,3-thiazol-2-yl]amino}-4,4,4-trifluorobutanoate (1.15 g, 2.81 mmol), prepared in the previous step, was dissolved in 28 mL of anhydrous tetrahydrofuran and cooled to 0° C. Lithium aluminum hydride (1M solution in THF, 5.6 mL, 5.6 mmol) was added dropwise and the mixture was stirred for 1 h. The reaction was quenched by careful addition of 0.22 mL of water, 0.22 mL of 15% aqueous KOH, followed by 0.66 mL of water and the mixture was stirred for 20 min. The mixture was diluted with ethyl acetate and filtered through the Celite™ reagent. The filtrate was washed with water, brine, dried over anhydrous MgSO$_4$, filtered and concentrated under reduced pressure. Flash chromatography (gradient 2% acetone/hexane to 5% acetone/hexane) afforded 2-{[4-(4-bromophenyl)-1,3-thiazol-2-yl]amino}-4,4,4-trifluorobutan-1-ol (0.81 g, 76%) as a white solid. mp 120-121° C. HRMS: calcd for $C_{13}H_{12}BrF_3N_2OS+H^+$, 380.98785; found (ESI, [M+H]$^+$), 380.9886. Analytical HPLC: retention time 10.2 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Step 3: 3-[4-(4-Bromophenyl)-1,3-thiazol-2-yl]-4-(2,2,2-trifluoroethyl)-1,3-oxazolidin-2-one 2-{[4-(4-Bromophenyl)-1,3-thiazol-2-yl]amino}-4,4,4-trifluorobutan-1-ol (0.700 g, 1.83 mmol), prepared in the previous step, was dissolved in 20 mL of methylene chloride. Triethylamine (2.65 mL, 18.3 mmol) was added and the solution was cooled to 0° C. Triphosgene (1.36 g, 4.6 mmol) was added in two portions and the mixture was stirred at 0° C. for 45 min and then at 25° C. for 2 h. The mixture was diluted with methylene chloride and poured into 250 mL of saturated aqueous sodium bicarbonate and the layers were separated. The organics were washed with water, brine, dried over anhydrous MgSO$_4$, filtered and concentrated under reduced pressure. Flash chromatography (5% acetone/hexane) afforded the title compound (0.62 g, 83%) as a white solid. mp 163-165° C. HRMS: calcd for $C_{14}H_{10}BrF_3N_2O_2S+H^+$, 406.96712; found (ESI, [M+H]$^+$), 406.9679. Analytical HPLC: retention time 10.8 min, 210-370 nm the Xterra® RP18 column, 3.5%, 150×4.6 mm 40° C. 85/15-5/95 (Ammon. Form. Buff. pH=3.5/ACN+MeOH) for 10 min, hold 4 min, 1.2 mL/min 5 μL injection.

Example 68

4-{2-[(4S)-2-Oxo-4-(2,2,2-trifluoroethyl)-1,3-oxazolidin-3-yl]-1,3-thiazol-4-yl}benzonitrile 3-[4-(4-Bromophenyl)-1,3-thiazol-2-yl]-4-(2,2,2-trifluoroethyl)-1,3-oxazolidin-2-one (0.53 g, 1.3 mmol), prepared in step 3 of Example 67, and zinc cyanide (91 mg, 0.78 mmol) were dissolved in 15 mL of DMF. The mixture was purged with nitrogen for 15 min, tetrakis(triphenylphosphine)palladium(0) (75 mg, 0.065 mmol) was added, and the mixture was heated at 120° C. for 3 h. The mixture was cooled and diluted with ethyl acetate and poured into 200 mL of water. The mixture was extracted with ethyl acetate, the organics were combined, washed with water, brine, dried over anhydrous MgSO$_4$, filtered and concentrated under reduced pressure. Flash chromatography (25% hexane in methylene chloride) afforded racemic 4-{2-[2-oxo-4-(2,2,2-trifluoroethyl)-1,3-oxazolidin-3-yl]-1,3-thiazol-4-yl}benzonitrile (364 mg, 79%) as a white solid.

The racemic mixture was resolved by preparative chiral HPLC:

| | |
|---|---|
| Instrumentation: | Varian Semiprep-HPLC |
| Chemicals: | Ethanol and acetonitrile was HPLC-grade from Mallinckrodt Baker (Muskegon, MI, USA) |
| Column: | the Chiralcel ® OJ-H column, 25 cm L × 20 mm ID, 5 μm particle size (Chiral Technologies Corp, Exton, PA, USA) |
| Temperature: | Ambient |
| Mobile Phase: | 100% ethanol |
| Flow rate: | 12 mL/min |
| Detection: | UV at 298 nm |
| Solvent: | 100% acetonitrile |

Chiral separation provided the title compound as a white solid, mp 235-238° C. HRMS: calcd for $C_{15}H_{10}F_3N_3O_2S+H^+$, 354.05186; found (ESI, [M+H]$^+$), 354.053. Analytical HPLC: retention time 9.6 min, 210-370 nm the Xterra® RP18 column, 3.5%, 150×4.6 mm 40° C. 85/15-5/95 (Ammon. Form. Buff. pH=3.5/ACN+MeOH) for 10 min, hold 4 min, 1.2 mL/min 5 μL injection.

Example 69

4-{2-[(4R)-2-Oxo-4-(2,2,2-trifluoroethyl)-1,3-oxazolidin-3-yl]-1,3-thiazol-4-yl}benzonitrile Isolation of the second component in the chiral separation from Example 68 provided the title compound as a white solid, mp 235-238° C. HRMS: calcd for $C_{15}H_{10}F_3N_3O_2S+H^+$, 354.05186; found (ESI, [M+H]$^+$), 354.0522.

Analytical HPLC: retention time 9.6 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Example 70

Methyl (4S)-3-[4-(4-bromophenyl)-1,3-thiazol-2-yl]-2-oxo-1,3-oxazolidine-4-carboxylate Step 1: 2-[4-(4-Bromophenyl)-1,3-thiazol-2-ylamino]-3-hydroxy-propionic acid methyl ester Serine methyl ester hydrochloride (1.02 g, 4 mmol) was dissolved in 50 mL of ethanol and 2-(4-bromophenyl)-2-oxoethyl thiocyanate (0.686 g, 4.4 mmol), prepared in step 1 of Example 1, was added followed by triethylamine (0.63 mL, 4.4 mmol). The mixture was heated to 60° C. for 18 h and then cooled and concentrated under reduced pressure. Flash chromatography (1% methanol/chloroform) afforded 1.1 g of 2-[4-(4-bromophenyl)-1,3-thiazol-2-ylamino]-3-hydroxy-propionic acid methyl ester (1.1 g, 79%) as a white solid.

Step 2: Methyl (4S)-3-[4-(4-bromophenyl)-1,3-thiazol-2-yl]-2-oxo-1,3-oxazolidine-4-carboxylate 2-[4-(4-Bromophenyl)-1,3-thiazol-2-ylamino]-3-hydroxy-propionic acid methyl ester (1.1 g, 3.08 mmol), prepared in the previous step, was dissolved in 40 mL of methylene chloride and triethylamine (4.3 mL, 30.8 mmol) was added. The mixture was cooled to 0° C. and triphosgene (2.3 g, 7.7 mmol) was added. The mixture was stirred for 1 h and then diluted with methylene chloride, washed with saturated NaHCO$_3$, water, and brine, dried over anhydrous MgSO$_4$, filtered and concentrated under reduced pressure. Flash chromatography (gradient 2% acetone/hexane to 15% acetone/hexane) afforded the title compound (510 mg, 44%) as a white solid. mp 165-167° C. HRMS: calcd for $C_{14}H_{11}BrN_2O_4S+H^+$, 382.96956; found (ESI, [M+H]$^+$), 382.9718. Analytical HPLC: retention time 9.9 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Example 71

(4R)-3-[4-(4-Bromophenyl)-1,3-thiazol-2-yl]-4-(hydroxymethyl)-1,3-oxazolidin-2-one Methyl (4S)-3-[4-(4-bromophenyl)-1,3-thiazol-2-yl]-2-oxo-1,3-oxazolidine-4-carboxylate (0.20 g, 0.52 mmol), prepared in step 2 of Example 70, was dissolved in 5 mL of tetrahydrofuran and cooled to 0° C. Lithium borohydride (2M solution in tetrahydrofuran, 0.57 mL, 1.14 mmol) was added and the mixture was stirred for 2 h. The mixture was allowed to warm to 25° C. and stirred for an additional 30 min, quenched with H$_2$O and then 2 mL of 2N HCl was added. The mixture was diluted with 10 mL of water and poured into ethyl acetate. The layers were separated and the aqueous layer was extracted with ethyl acetate. The organics were combined and washed with water, brine, dried over anhydrous MgSO$_4$, filtered and concentrated under reduced pressure. Flash chromatography (25% acetone/hexane) afforded the title compound (124 mg, 69%) as a white solid. mp 189-192° C. HRMS: calcd for $C_{13}H_{11}BrN_2O_3S+H^+$, 354.97465; found (ESI, [M+H]$^+$), 354.9742. Analytical HPLC: retention time 9.2 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Example 72

(4S)-3-[4-(4-Bromophenyl)-1,3-thiazol-2-yl]-4-(chloromethyl)-1,3-oxazolidin-2-one (4R)-3-[4-(4-Bromophenyl)-1,3-thiazol-2-yl]-4-(hydroxymethyl)-1,3-oxazolidin-2-one (80 mg, 0.23 mmol), prepared in Example 71, was dissolved in 5 mL methylene chloride and cooled to −78° C. A solution of (diethylamino)sulfur trifluoride (0.034 mL, 0.25 mmol) in 5 mL of methylene chloride was added dropwise. The mixture was stirred at −78° C. for 1 h then warmed to 25° C. The reaction was quenched by pouring over ice and was then diluted with water and methylene chloride. The layers were separated and the aqueous layer was extracted with methylene chloride. The organics were combined and washed with water, brine, dried over anhydrous MgSO$_4$, filtered and concentrated under reduced pressure. Flash chromatography (gradient 10% acetone/hexane to 20% acetone/hexane) afforded the title compound (12 mg, 14%) as a white solid. HRMS: calcd for $C_{13}H_{10}BrClN_2O_2S+H^+$, 372.94076; found (ESI, [M+H]$^+$), 372.9406. Analytical HPLC: retention time 10.6 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Example 73

(4S)-3-[4-(4-Bromophenyl)-1,3-thiazol-2-yl]-4-(fluoromethyl)-1,3-oxazolidin-2-one (4R)-3-[4-(4-Bromophenyl)-1,3-thiazol-2-yl]-4-(hydroxymethyl)-1,3-oxazolidin-2-one (0.71 g, 2.0 mmol), prepared in Example 71, was dissolved in 20 mL methylene chloride and cooled to 0° C. (Diethylamino)sulfur trifluoride (0.295 mL, 2.20 mmol) was added dropwise. The mixture was warmed to 25° C. and stirred for 2.5 h. The reaction was quenched with water and saturated NaHCO$_3$ and the mixture was extracted with methylene chloride. The organics were combined and washed with water, brine, dried over anhydrous MgSO$_4$, filtered and concentrated under reduced pressure. Flash chromatography (8% acetone/hexane) afforded the title compound (243 mg, 34%) as a white solid. mp 148-150° C. HRMS: calcd for $C_{13}H_{10}BrFN_2O_2S+H^+$, 356.97031; found (ESI, [M+H]$^+$), 356.9705. Analytical HPLC: retention time 10.2 min, 210-370 nm the Xterra® RP18 column, 3.5μ, 150×4.6 mm 40° C. 85/15-5/95 (Ammon. Form. Buff. pH 3.5/ACN+MeOH) for 10 min, hold 4 min, 1.2 mL/min 5 μL injection.

Example 74

4-{2-[(4S)-4-(Fluoromethyl)-2-oxo-1,3-oxazolidin-3-yl]-1,3-thiazol-4-yl}benzonitrile (4S)-3-[4-(4-Bromophenyl)-1,3-thiazol-2-yl]-4-(fluoromethyl)-1,3-oxazolidin-2-one (0.21 g, 0.59 mmol), prepared in Example 73, and zinc cyanide (41 mg, 0.35 mmol) were dissolved in 8 mL of dimethylformamide. The mixture was purged with nitrogen for 15 min, tetrakis(triphenylphosphine)palladium(0) (34 mg, 0.029 mmol) was added and the mixture was heated to 120° C. for 2 h. The mixture was cooled and diluted with ethyl acetate, and washed with water, brine, dried over anhydrous $MgSO_4$, filtered and concentrated under reduced pressure. Flash chromatography (100% $CH_2Cl_2$) afforded the title compound (146 mg, 81%) as a white solid. mp 195-196° C. HRMS: calcd for $C_{14}H_{10}FN_3O_2S+H^+$, 304.05505; found (ESI, [M+H]$^+$), 304.0555. Analytical HPLC: retention time 8.8 min, 210-370 nm the Xterra® RP18 column, 3.5%, 150×4.6 mm 40° C. 85/15-5/95 (Ammon. Form. Buff. pH=3.5/ACN+MeOH) for 10 min, hold 4 min, 1.2 mL/min 5 μL injection.

Example 75

1-[4-(4-Bromophenyl)-1,3-thiazol-2-yl]imidazolidin-2-one

Step 1: N-[4-(4-Bromophenyl)-1,3-thiazol-2-yl]ethane-1,2-diamine

2-Bromo-4-(4-bromophenyl)-1,3-thiazole (2.0 g, 6.2 mmol), prepared in step 2 of Example 1, was dissolved in ethylenediamine (10.0 mL, 185 mmol) and heated to 130° C. for 2 h. The mixture was cooled and poured into saturated $NaHCO_3$ and extracted with ether. The ether extracts were combined and washed with water, brine, dried over anhydrous $MgSO_4$, filtered and concentrated under reduced pressure to give N-[4-(4-bromophenyl)-1,3-thiazol-2-yl]ethane-1,2-diamine (1.8 g, 97%) as a yellow solid. HRMS: calcd for $C_{11}H_{12}BrN_3S+H^+$, 298.00080; found (ESI, [M+H]$^+$), 298.0012. Analytical HPLC: retention time 7.0 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Step 2: 1-[4-(4-Bromophenyl)-1,3-thiazol-2-yl]imidazolidin-2-one

N-[4-(4-bromophenyl)-1,3-thiazol-2-yl]ethane-1,2-diamine (1.1 g, 3.7 mmol), prepared in the previous step, was dissolved in 30 mL methylene chloride and triethylamine (5.1 mL, 36.9 mmol) was added. The mixture was cooled to 0° C., triphosgene (2.7 g, 9.2 mmol) was added, and the mixture was stirred for 3 h. The mixture was diluted with ethyl acetate, washed with $NaHCO_3$, water, brine, dried over anhydrous $MgSO_4$, filtered and concentrated under reduced pressure. Flash chromatography (2% methanol/methylene chloride) afforded the title compound (250 mg, 21%) as a white solid; mp 230-233° C. HRMS: calcd for $C_{12}H_{10}BrN_3OS+H^+$, 323.98007; found (ESI, [M+H]$^+$), 323.9808. Analytical HPLC: retention time 9.7 min, 210-370 nm the Xterra® RP18 column, 3.5%, 150×4.6 mm 40° C. 85/15-5/95 (Ammon. Form. Buff. pH=3.5/ACN+MeOH) for 10 min, hold 4 min, 1.2 mL/min 5 μL injection.

Example 76

1-[4-(4-Bromophenyl)-1,3-thiazol-2-yl]-3-methylimidazolidin-2-one

1-[4-(4-Bromophenyl)-1,3-thiazol-2-yl]imidazolidin-2-one (0.155 g, 0.480 mmol), prepared in step 2 of Example 75, was dissolved in 2.4 mL of anhydrous tetrahydrofuran and sodium hydride (60% suspension in mineral oil, 20 mg, 0.53 mmol) was added. The mixture was stirred for 20 min and then methyl iodide (0.03 mL, 0.48 mmol) was added and stirring was continued for 4 h. The reaction was quenched with saturated aqueous $NH_4Cl$ and diluted with ethyl acetate. The mixture was washed with water, brine, dried over anhydrous $MgSO_4$, filtered and concentrated under reduced pressure. Flash chromatography (20% acetone/hexane) afforded the title compound (146 mg, 90%) as a white solid. HRMS: calcd for $C_{13}H_{12}BrN_3OS+H^+$, 337.99572; found (ESI, [M+H]$^+$), 337.9954. Analytical HPLC: retention time 10.1 min, 210-370 nm the Xterra® RP18 column, 3.5%, 150×4.6 mm 40° C. 85/15-5/95 (Ammon. Form. Buff. pH=3.5/ACN+MeOH) for 10 min, hold 4 min, 1.2 mL/min 5 μL injection.

Example 77

3-[4-(4-Bromophenyl)-1,3-thiazol-2-yl]-2,2-dimethyl-1,3-oxazolidin-4-one

Step 1: 2-{[4-(4-Bromophenyl)-1,3-thiazol-2-yl]amino}-2-oxoethyl acetate 4-(4-Bromophenyl)-1,3-thiazol-2-ylamine (2.00 g, 7.84 mmol) was dissolved in methylene chloride, diisopropylethylamine (1.50 mL, 8.62 mmol) was added and the mixture was cooled to 0° C. Acetoxy acetyl chloride (0.920 mL, 8.62 mmol) was added dropwise, the mixture was stirred for 2 h and then diluted with ethyl acetate. The mixture was washed with $NaHCO_3$, water, brine, dried over anhydrous $MgSO_4$, filtered and concentrated under reduced pressure. Flash chromatography (20% acetone/hexane) followed by recrystallization from acetone/hexane afforded 1.16 g of 2-{[4-(4-bromophenyl)-1,3-thiazol-2-yl]amino}-2-oxoethyl acetate (1.16 g, 42%) as a white solid. HRMS: calcd for $C_{13}H,BrN_2O_3S+H^+$, 354.97465; found (ESI, [M+H]$^+$), 354.9738. Analytical HPLC: retention time 9.8 min, 210-370 nm the Xterra® RP18 column, 3.5%, 150×4.6 mm 40° C. 85/15-5/95 (Ammon. Form. Buff. pH=3.5/ACN+MeOH) for 10 min, hold 4 min, 1.2 mL/min 5 μL injection.

Step 2: N-[4-(4-Bromophenyl)-1,3-thiazol-2-yl]-2-hydroxyacetamide

2-{[4-(4-Bromophenyl)-1,3-thiazol-2-yl]amino}-2-oxoethyl acetate (1.1 g, 3.1 mmol), prepared in the previous step, was suspended in 20 mL of methanol and $K_2CO_3$ (0.43 g, 3.1 mmol) was added. The mixture was stirred for 2 h, then diluted using methylene chloride. The mixture was washed with water, brine, dried over anhydrous $MgSO_4$, filtered and concentrated under reduced pressure. Flash chromatography (2% methanol/chloroform) provided N-[4-(4-bromophenyl)-1,3-thiazol-2-yl]-2-hydroxyacetamide (670 mg, 68%) as a white solid. mp 222-224° C. HRMS: calcd for $C_{11}H_9BrN_2O_2S+H^+$, 312.96408; found (ESI, [M+H]$^+$), 312.9651. Analytical HPLC: retention time 9.0 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Step 3: 3-[4-(4-Bromophenyl)-1,3-thiazol-2-yl]-2,2-dimethyl-1,3-oxazolidin-4-one N-[4-(4-Bromophenyl)-1,3-thiazol-2-yl]-2-hydroxyacetamide (0.35 g, 1.12 mmol), prepared in the previous step, was suspended in 10 mL of toluene, dimethoxypropane (2.0 mL, 16.7 mmol) was added, which was followed by a catalytic amount of p-toluenesulfonic acid monohydrate (20 mg). The mixture was heated to 90° C. for 16 h, then cooled and concentrated under reduced pressure. Flash chromatography (5% acetone/hexane) provided the title compound (210 mg, 53%) as a white solid. HRMS: calcd for $C_{14}H_{13}BrN_2O_2S+H^+$, 352.99538; found (ESI, [M+H]$^+$), 352.9957. Analytical HPLC: retention time 11.1 min, 210-370 nm the Xterra® RP18 column, 3.5μ, 150×4.6 mm 40° C. 85/15-5/95 (Ammon. Form. Buff. pH=3.5/ACN+MeOH) for 10 min, hold 4 min, 1.2 mL/min 5 μL injection.

Example 78

3-[4-(4-Bromo-2-fluorophenyl)-1,3-thiazol-2-yl]-4,4-dimethyl-1,3-oxazolidin-2-one

Step 1: 1-(4-Bromo-2-fluoro-phenyl)-ethanol

Methylmagnesium bromide (70 mL of a 1.4 M solution in toluene/tetrahydrofuran [75:25], 97.5 mmol) was added dropwise to a solution of 4-bromo-2-fluorobenzaldehyde (19.5 g, 88.6 mmol) in 110 mL of dry tetrahydrofuran at 0° C. The solution was warmed to room temperature. After 30 min, TLC (3:1 hexane:ethyl acetate) indicated the starting material was consumed. The reaction was quenched with saturated NH$_4$Cl dropwise at 0° C. The solution was concentrated to one-half volume, diluted with ethyl acetate and washed with water and brine. The organic layer was dried over anhydrous sodium sulfate, filtered and the solvent concentrated under reduced pressure to give 22.5 g of a yellow oil. The crude product was purified on silica gel using a stepwise gradient of 10:1 to 8:1 hexane:ethyl acetate to give 1-(4-bromo-2-fluorophenyl)-ethanol (8.9 g, 46%) as a white solid. MS (ES) m/z 220 [M+H]$^+$.

Step 2: 1-(4-Bromo-2-fluoro-phenyl)-ethanone

Jones reagent (26.72 g of chromic trioxide in 23 mL of sulfuric acid diluted with water to a volume of 100 mL; 6.3 mL) was added dropwise to a solution of 1-(4-bromo-2-fluoro-phenyl)-ethanol (5.9 g; 26.9 mmol), prepared in the previous step, in 110 mL of dry acetone at 0° C. The reaction was stirred for 30 min. TLC (3:1 hexane:ethyl acetate) indicated the starting material was consumed. Water was added to the reaction mixture, which was extracted with methylene chloride. The organic layer was dried over anhydrous sodium sulfate, filtered and concentrated under reduced pressure to give 6.0 g of a green oil. The crude product was purified on silica gel using a stepwise gradient of 6:1 to 3:1 hexane:ethyl acetate to give 1-(4-bromo-2-fluoro-phenyl)-ethanone (5.0 g, 86%), MS (ES) m/z 218 [M+H]$^+$.

Step 3: 2-Bromo-1-(4-bromo-2-fluoro-phenyl)-ethanone

Bromine (1.2 mL, 23.0 mmol) in 10 mL of glacial acetic acid was added drop-wise to a solution of 1-(4-bromo-2-fluoro-phenyl)-ethanone (5.0 g, 23.0 mmol), prepared in the previous step, in 150 mL of dry methylene chloride at 0° C. After the addition, the reaction was allowed to warm to room temperature. TLC (5% ethyl acetate:hexane) indicated the starting material was consumed. The reaction was diluted with methylene chloride and washed with 5% sodium thiosulfate and brine. The organic layer was dried over anhydrous sodium sulfate, filtered and concentrated under reduced pressure to give 2-bromo-1-(4-bromo-2-fluoro-phenyl)-ethanone (6.6 g, 97%) as a light green oil. This compound was used without further purification. MS (ES) m/z 297 [M+H]$^+$.

Step 4: 2-(4-Bromo-2-fluorophenyl)-2-oxoethyl thiocyanate

Potassium isothiocyanate (2.4 g, 24.5 mmol) was added in portions to a solution of 2-bromo-1-(4-bromo-2-fluoro-phenyl)-ethanone (6.6 g, 22.3 mmol), prepared in the previous step, in 280 mL of dry ethanol. The mixture was warmed to 50° C. for 1 h. The reaction was cooled to room temperature, diluted with water and the resulting precipitate was collected by suction filtration and air dried to give 5.9 g of a dark orange residue. The crude product was purified on silica gel using a stepwise gradient of 5% to 20% ethyl acetate:hexane to give 2-(4-bromo-2-fluorophenyl)-2-oxoethyl thiocyanate (4.0 g, 65%). MS (ES) m/z 275 [M+H]$^+$.

Step 5: 2-Bromo-4-(4-bromo-2-fluorophenyl)-1,3-thiazole 2-(4-Bromo-2-fluorophenyl)-2-oxoethyl thiocyanate (2.1 g, 7.6 mmol), prepared in the previous step, in 15 mL of 33% hydrogen bromide in acetic acid was stirred overnight. The reaction was neutralized with 60 mL of 2N NaOH and 60 mL of water. The resulting residue was collected by suction filtration and placed under high vacuum to give 2.6 g of a brown paste. The crude product was purified on silica gel using a stepwise gradient of 5-20% ethyl acetate:hexane to give 2-bromo-4-(4-bromo-2-fluorophenyl)-1,3-thiazole (2.5 g, 98%), MS (ES) m/z 338 [M+H]$^+$.

Step 6: 2-{[4-(4-Bromo-2-fluorophenyl)-1,3-thiazol-2-yl]amino}-2-methylpropan-1-ol 2-Bromo-4-(4-bromo-2-fluorophenyl)-1,3-thiazole (1.5 g, 4.4 mmol), prepared in the previous step, and 2-amino-2-methyl-1-propanol (2.5 mL, 26.7 mmol) were placed in a sealed tube and heated to 175° C. overnight. The reaction was concentrated under reduced pressure. The residue was purified on silica gel using a stepwise gradient of 5-40% ethyl acetate:hexane to give 2-{[4-(4-bromo-2-fluorophenyl)-1,3-thiazol-2-yl]amino}-2-methylpropan-1-ol (0.3 g, 22%), MS (ES) m/z 346 [M+H]$^+$.

Step 7: 3-[4-(4-Bromo-2-fluorophenyl)-1,3-thiazol-2-yl]-4,4-dimethyl-1,3-oxazolidin-2-one N,N-diisopropylethylamine (1.2 mL, 6.9 mmol) was added to a solution of 2-{[4-(4-bromo-2-fluorophenyl)-1,3-thiazol-2-yl]amino}-2-methylpropan-1-ol (1.0 g, 2.9 mmol), prepared in the previous step, in 50 mL of dry methylene chloride at 0° C. Triphosgene (1.0 g, 3.4 mmol) in 10 mL of dry methylene chloride was added drop-wise over 10 min. The orange solution was stirred at 0° C. for 3 h and then allowed to warm to room temperature. The reaction was washed with 2N HCl and the aqueous layer was extracted with methylene chloride. The organic layer was dried over anhydrous magnesium sulfate, filtered and concentrated under reduced pressure to give 1.2 g of a green residue. The crude product was

Example 79

4-[2-(4,4-Dimethyl-2-oxo-1,3-oxazolidin-3-yl)-1,3-thiazol-4-yl]-3-fluorobenzonitrile Copper (I) cyanide (0.09 g, 1.0 mmol) and pyridine (0.17 mL, 1.6 mmol) were added under a nitrogen atmosphere to a solution of 3-[4-(4-bromo-2-fluorophenyl)-1,3-thiazol-2-yl]-4,4-dimethyl-1,3-oxazolidin-2-one (0.4 g, 1.0 mmol), prepared in step 7 of Example 78, and tetrakis(triphenylphosphine)palladium(0) (115 mg, 0.1 mmol) in dimethylacetamide. The reaction solution was sealed and placed in a microwave reactor (200° C./1 h). LC/MS indicated the reaction was complete. The reaction was concentrated under reduced pressure. The residue was purified on silica gel using a stepwise gradient of 1-3% methanol:methylene chloride to give the title compound (370 mg, 55%) as a yellow solid, mp 237° C. (dec.).

Example 80

4,4-Dimethyl-3-[4-(4-nitrophenyl)-1,3-thiazol-2-yl]-1,3-oxazolidin-2-one

Step 1: 2-Bromo-4-(4-nitrophenyl)-1,3-thiazole 2-(4-Nitrophenyl)-2-oxoethyl thiocyanate (3.0 g; 15.4 mmol) and 50 mL of 30% HBr in acetic acid were stirred at room temperature under nitrogen overnight. The yellow paste was neutralized with 60 mL of 2N NaOH and 60 mL of $H_2O$. The residue was collected by suction filtration. Purification of the residue on silica gel using a stepwise gradient of 5-50% ethyl acetate:hexane gave 2-bromo-4-(4-nitrophenyl)-1,3-thiazole (2.0 g, 45%), MS (ES) m/z 286[M+H]$^+$.

Step 2: 2-{[4-(4-Nitrophenyl)-1,3-thiazol-2-yl]amino}-2-methylpropan-1-ol

2-Bromo-4-(4-nitrophenyl)-1,3-thiazole (1.0 g, 3.5 mmol), prepared in the previous step, and 2-amino-2-methylpropan-1-ol (2.0 mL, 21.0 mmol) were placed in a sealed tube and heated to 175° C. for 18 h. The crude product was pre-adsorbed onto silica gel and purified using a stepwise gradient of 1-5% methanol:methylene chloride to give 2-{[4-(4-nitrophenyl)-1,3-thiazol-2-yl]amino}-2-methylpropan-1-ol (700 mg, 69%), MS (ES) m/z 294[M+H]$^+$.

Step 3: 4,4-Dimethyl-3-[4-(4-nitrophenyl)-1,3-thiazol-2-yl]-1,3-oxazolidin-2-one N,N-diisopropylethylamine (1.0 mL, 5.7 mmol) was added dropwise to a solution of 2-{[4-(4-nitrophenyl)-1,3-thiazol-2-yl]amino}-2-methylpropan-1-ol (0.7 g, 2.4 mmol), prepared in the previous step, in 20 mL of dry methylene chloride at 0° C., followed by triphosgene (0.8 g, 2.8 mmol) in 20 mL of dry dichloromethane. The orange solution was stirred at 0° C. for 3 h, and then allowed to warm to room temperature. TLC (3:1 hexane:ethyl acetate) indicated the reaction was complete. The reaction was washed with 2N HCl and the aqueous layer was extracted with methylene chloride. The combined organic layer was dried (anhydrous $MgSO_4$), filtered and concentrated under reduced pressure to give 900 mg of a yellow solid. Purification of the solid on silica gel using a stepwise gradient of 6:1 to 5:1 hexane:ethyl acetate gave the title compound (268 mg, 35%), mp 176-179° C.

Example 81

4-[2-(4,4-Dimethyl-2-oxo-1,3-oxazolidin-3-yl)-1,3-thiazol-4-yl]-2-fluorobenzonitrile

Step 1: 4-Acetyl-2-fluorobenzonitrile

A mixture of 4-bromo-2-fluorobenzonitrile (10.6 g, 52.8 mmol), tributyl(1-ethoxyvinyl)tin (21 g, 58.1 mmol), and trans-dichlorobis(triphenylphosphine)palladium (II) (371 mg, 0.53 mmol) in 190 mL of dry toluene were refluxed for 2 h and then quenched with 5% HCl and stirred for 30 min. Ethyl acetate was added and the layers were separated. The organic layer was dried over anhydrous sodium sulfate, filtered and concentrated under reduced pressure to give 6.5 g of crude product. Purification of the product on silica gel using 5% ethyl acetate:hexane gave 4-acetyl-2-fluorobenzonitrile (1.0 g, 11%), MS (ES) m/z 164 [M+H]$^+$.

Step 2: 4-(2-Bromoacetyl)-2-fluorobenzonitrile

Bromine (315 µL, 6.1 mmol) in 400 µL of acetic acid was added to a solution of 4-acetyl-2-fluorobenzonitrile (1.0 g, 6.1 mmol), prepared in the previous step, in 50 mL of dry methylene chloride at room temperature. After 1.5 h, TLC (5-1, hexane:ethyl acetate) indicated the starting material was consumed. The reaction was diluted with ethyl acetate (100 mL) and washed with 10% aqueous sodium thiosulfate (2×100 mL) followed by saturated sodium bicarbonate (1×100 mL) and brine (1×100 mL). The organic layer was dried over anhydrous sodium sulfate, filtered and concentrated under reduced pressure to give 1.1 g of a yellow solid. Purification of the solid on silica gel using a stepwise gradient of 10% to 50% ethyl acetate-hexane gave 4-(2-bromoacetyl)-2-fluorobenzonitrile (800 mg, 53%), MS (ES) m/z 243[M+H]$^+$.

Step 3: 2-Fluoro-4-{2-[(2-hydroxy-1,1-dimethylethyl)amino]-1,3-thiazol-4-yl}benzonitrile 4-(2-Bromoacetyl)-2-fluorobenzonitrile (800 mg, 3.3 mmol), prepared in the previous step, and N-(2-hydroxy-1,1-dimethylethyl)thiourea (490 mg, 3.3 mmol), prepared in step 2 of Example 52, in 100 mL of ethanol were heated to reflux for 30 min and then concentrated under reduced pressure to give 1.1 g of a yellow residue. Purification of the residue on silica gel using a stepwise gradient of 1% to 8% methanol:methylene chloride gave 2-fluoro-4-{2-[(2-hydroxy-1,1-dimethylethyl)amino]-1,3-thiazol-4-yl}benzonitrile (955 mg, 99%), mp 128-130° C., MS (ES) m/z 292 [M+H]$^+$.

Step 4: 4-[2-(4,4-Dimethyl-2-oxo-1,3-oxazolidin-3-yl)-1,3-thiazol-4-yl]-2-fluorobenzonitrile N,N-diisopropylethylamine (1.4 mL, 7.9 mmol) and triphosgene (1.2 g, 3.9 mmol) in 20 mL of dry methylene chloride were added to a solution of 2-fluoro-4-{2-[(2-hydroxy-1,1-dimethylethyl)amino]-1,3-thiazol-4-yl}benzonitrile (955 mg, 3.3 mmol), prepared in the previous step, in 50 mL of dry methylene chloride at 0° C. The reaction was stirred at 0° C. for 3 h and then allowed to warm to room temperature. The reaction was washed with 1×100 mL of 2N HCl. The aqueous layer was extracted with methylene chloride (2×100 mL). The combined organic layers were dried over anhydrous $MgSO_4$, filtered and concentrated under reduced pressure to give 1.0 g of a yellow solid. Purification of the solid on silica gel using

--- purified on silica gel using a step-wise gradient of 5-30% ethyl acetate:hexane to give the title compound (0.9 g, 89%). MS (ES) m/z 372 [M+H]$^+$.

Example 82

4-[2-(4,4-Dimethyl-2-thioxo-1,3-oxazolidin-3-yl)-1,3-thiazol-4-yl]benzonitrile

Step 1: 4-{2-[(2-Hydroxy-1,1-dimethylethyl)amino]-1,3-thiazol-4-yl}benzonitrile This compound was prepared in the same manner as described in step 3 of Example 81. 4-(2-bromoacetyl)benzonitrile (1.7 g, 7.4 mmol) and N-(2-hydroxy-1,1-dimethylethyl)thiourea (1.1 g, 7.4 mmol), prepared in step 2 of Example 52, were heated to reflux in 45 mL of ethanol for 30 min. The reaction mixture was cooled to room temperature and the crude product was collected by suction filtration to give 4-{2-[(2-hydroxy-1,1-dimethylethyl)amino]-1,3-thiazol-4-yl}benzonitrile (2.0 g, 100%), MS (ES) m/z 274 [M+H]$^+$. No further purification was performed on this compound.

Step 2: 4-[2-(4,4-Dimethyl-2-thioxo-1,3-oxazolidin-3-yl)-1,3-thiazol-4-yl]benzonitrile 1,1-Thiocarbonyldiimidazole (652 mg, 3.6 mmol) was added to a solution of 4-{2-[(2-hydroxy-1,1-dimethylethyl)amino]-1,3-thiazol-4-yl}benzonitrile (1.0 g, 3.6 mmol), prepared in the previous step, in 60 mL of dry tetrahydrofuran at 0° C. The solution was allowed to warm to room temperature. After 2 h, starting material remained. The reaction was heated to reflux. After 12 h, the reaction was cooled to room temperature and concentrated under reduced pressure. Purification of the residue by reverse phase HPLC using a continuous gradient of 70-83% acetonitrile-water over 10 min gave the title compound (130 mg, 11%) as a tan solid. mp>240° C. (dec.)

Example 83

4-[2-(3,5,5-Trimethyl-2-oxoimidazolidin-1-yl)-1,3-thiazol-4-yl]benzonitrile

Step 1: 4-{2-[(1,1-Dimethyl-2-oxoethyl)amino]-1,3-thiazol-4-yl}benzonitrile A 1M solution of oxalyl chloride in methylene chloride (20 mL, 20 mmol) was cooled to −78° C., dimethyl sulfoxide was added dropwise (1.77 mL, 25 mmol) and the mixture was stirred. This solution (5.5 mL, 5.5 mmol of activated dimethyl sulfoxide) was added via syringe to a solution of 4-{2-[(2-hydroxy-1,1-dimethylethyl)amino]-1,3-thiazol-4-yl}benzonitrile (1.5 g, 5.5 mmol), prepared in step 1 of Example 82, in 60 mL of 5:1 methylene chloride:tetrahydrofuran that had been cooled to −78° C. The reaction was stirred for 30 min, triethylamine (1.6 mL, 11 mmol) was added, the mixture was stirred for 20 min and then allowed to warm to 25° C. The mixture was then diluted with methylene chloride and washed with H$_2$O, brine, dried over anhydrous MgSO$_4$, filtered and concentrated. Flash chromatography (10%-20% acetone in hexane) afforded 4-{2-[(1,1-dimethyl-2-oxoethyl)amino]-1,3-thiazol-4-yl}benzonitrile (0.91 g, 61%) of as a white solid. HRMS: calcd for C$_{14}$H$_{13}$N$_3$OS+H$^+$, 272.08521; found (ESI, [M+H]$^+$), 272.0853; Analytical HPLC: HPLC purity 100% at 210-370 nm, 9.1 min; 100% at 328 nm, 9.1 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Step 2: 4-[2-(3,5,5-Trimethyl-2-oxoimidazolidin-1-yl)-1,3-thiazol-4-yl]benzonitrile 4-{2-[(1,1-dimethyl-2-oxoethyl)amino]-1,3-thiazol-4-yl}benzonitrile (318 mg, 1.17 mmol), prepared in the previous step, was dissolved in 12 mL of methanol and 1 g of molecular sieves was added. Acetic acid (0.13 mL, 2.3 mmol) and a 2M solution of methylamine in methanol (1.76 mL, 3.52 mmol) were added followed by sodium cyanoborohydride (0.44 g, 7.0 mmol) and the mixture was stirred for 16 h. Sodium triacetoxyborohydride (1.5 g, 7.0 mmol) was added and the mixture was stirred for 72 h. The mixture was diluted with ethyl acetate and washed with H$_2$O, NaHCO$_3$, brine, dried over anhydrous MgSO$_4$, filtered and concentrated to give 380 mg of crude product. This material was dissolved in 15 mL tetrahydrofuran and triethylamine (1.0 mL, 7.3 mmol) was added followed by triphosgene (0.59 g, 2.0 mmol). The mixture was stirred for 2 h, poured into saturated NaHCO$_3$, diluted with methylene chloride and washed with H$_2$O, 1N HCl, brine, dried over anhydrous MgSO$_4$, filtered and concentrated. Flash chromatography (20% ethyl acetate/hexane) afforded the title compound (0.105 g, 25%) as a white solid. HRMS: calcd for C$_{16}$H$_{16}$N$_4$OS+H$^+$, 313.11176; found (ESI, [M+H]$^+$), 313.1104; Analytical HPLC: purity 100% at 210-370 nm, 9.7 min; 100% at 252 nm, 9.7 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Example 84

4-[2-(3-Benzyl-5,5-dimethyl-2-oxoimidazolidin-1-yl)-1,3-thiazol-4-yl]benzonitrile 4-{2-[(1,1-Dimethyl-2-oxoethyl)amino]-1,3-thiazol-4-yl}benzonitrile (290 mg, 1.07 mmol), prepared in step 1 of Example 83, was dissolved in methanol (8 mL) and tetrahydrofuran (2 mL) and then 1 g of molecular sieves was added. Acetic acid (0.12 mL, 2.1 mmol) and benzylamine (0.35 mL, 3.21 mmol) were added, followed by sodium cyanoborohydride (0.404 g, 6.42 mmol), and the mixture was stirred for 3 h. The mixture was diluted with ethyl acetate and washed with H$_2$O, brine, dried over anhydrous MgSO$_4$, filtered and concentrated to give 390 mg of crude product. This material was dissolved in 15 mL tetrahydrofuran and triethylamine (0.81 mL, 5.6 mmol) was added followed by triphosgene (0.48 g, 1.6 mmol). The mixture was stirred for 1 h, poured into saturated NaHCO$_3$, diluted with methylene chloride and washed with H$_2$O, 1N HCl, brine, dried over anhydrous MgSO$_4$, filtered and concentrated. Flash chromatography (20% ethyl acetate/hexane) afforded the title compound (0.250 g, 60%) as a pale yellow solid. HRMS: calcd for C$_{22}$H$_{20}$N$_4$OS+H$^+$, 389.14306; found (ESI, [M+H]$^+$), 389.1449; Analytical HPLC: 83.0% at 210-370 nm, 11.0 min; 84.4% at 252 nm, 11.0 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Example 85

4-[2-(4,4-Dimethyl-2-oxo-1,3-oxazolidin-3-yl)-1,3-thiazol-4-yl]-N'-hydroxybenzene carboximidamide 4-[2-(4,4-Dimethyl-2-oxo-1,3-oxazolidin-3-yl)-1,3-thiazol-4-yl]benzonitrile (0.10 mg, 0.33 mmol), prepared in Example 6, was dissolved in tetrahydrofuran (2 mL). A 1M solution of hydroxylamine in dimethyl sulfoxide (1.5 mL, 1.5 mmol) was added and the mixture was stirred for 16 h. The mixture was diluted with ethyl acetate and washed with H$_2$O, brine, dried over anhydrous MgSO$_4$, filtered and concentrated. Flash chromatography (1% methanol/methylene chloride) afforded the title compound (70 mg, 64%) as a white solid. HRMS: calcd for C$_{15}$H$_{16}$N$_4$O$_3$S+H$^+$, 333.10159; found (ESI-FT/MS, [M+H]$^{1+}$), 333.102; Analytical HPLC: purity 100% at 210-370 nm, 6.9 min; 100% at 292 nm, 6.9 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 mm.

Example 86

2-(4,4-Diethyl-2-oxo-1,3-oxazolidin-3-yl)-4,5-dihydronaphtho[1,2-d][1,3]thiazole-7-carbonitrile Step 1: 2-{[1-Ethyl-1-(hydroxymethyl)propyl]amino}-4,5-dihydronaphtho[1,2-d][1,3]thiazole-7-carbonitrile 6-Bromo-5-oxo-5,6,7,8-tetrahydronaphthalene-2-carbonitrile (0.23 g, 0.90 mmol) was dissolved in 10 mL of ethanol and N-[1-ethyl-1-(hydroxymethyl)propyl]thiourea (133 mg, 1.32 mmol), prepared in step 5 of example 19, was added and the mixture was heated to reflux for 1 h. The mixture was cooled, diluted with ethyl acetate and washed with H$_2$O, NaHCO$_3$, brine, dried over anhydrous MgSO$_4$, filtered and concentrated. Flash chromatography (3% acetone/hexane) afforded 2-{[1-ethyl-1-(hydroxymethyl)propyl]amino}-4,5-dihydronaphtho[1,2-d][1,3]thiazole-7-carbonitrile (160 mg, 55%) as a white solid. HRMS: calcd for C$_{18}$H$_{21}$N$_3$OS+H$^+$, 328.14781; found (ESI-FTMS, [M+H]$^{1+}$), 328.14836; Analytical HPLC: purity 93.3% at 210-370 nm, 10.3 min; 96.4% at 254 nm, 10.3 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Step 2: 2-(4,4-diethyl-2-oxo-1,3-oxazolidin-3-yl)-4,5-dihydronaphtho[1,2-d][1,3]thiazole-7-carbonitrile 2-{[1-Ethyl-1-(hydroxymethyl)propyl]amino}-4,5-dihydronaphtho[1,2-d][1,3]thiazole-7-carbonitrile (0.29 g, 0.89 mmol), prepared in the previous step, was dissolved in methylene chloride (10 mL) and diisopropylethyl amine (0.37 mL, 2.1 mmol) was added and the mixture was cooled to 0° C. Triphosgene (108 mg, 1.07 mmol) was added and the mixture was stirred for 2 h. The mixture was then diluted with methylene chloride and washed with 2N HCl, saturated NaHCO$_3$, brine, dried over anhydrous MgSO$_4$, filtered and concentrated. Flash chromatography (10%-15% ethyl acetate in hexane) afforded the title compound (230 mg, 73%) as a white solid. HRMS: calcd for C$_{19}$H$_{19}$N$_3$O$_2$S+H$^+$, 354.12707; found (ESI-FT/MS, [M+H]$^{1+}$), 354.127; Analytical HPLC: purity 98.1% at 210-370 nm, 10.7 min; 98.8% at 316 nm, 10.7 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Example 87

4-[2-(2,2-Dimethyl-5-oxo-2,5-dihydro-1H-pyrrol-1-yl)-1,3-thiazol-4-yl]benzonitrile Step 1: Methyl (2E)-4-{[4-(4-cyanophenyl)-1,3-thiazol-2-yl]amino}-4-methylpent-2-enoate To a suspension of sodium hydride (60% in oil, 0.17 g, 4.5 mmol) in tetrahydrofuran (30 mL) was added trimethyl phosphonoacetate (0.75 mL, 5.2 mmol) dropwise and the mixture was stirred for 45 min. A solution of 4-{2-[(1,1-dimethyl-2-oxoethyl)amino]-1,3-thiazol-4-yl}benzonitrile (0.81 g, 3.0 mmol), prepared in step 1 of Example 83, in 5 mL of tetrahydrofuran was added and the mixture was stirred at 25° C. for 2 h. The reaction was quenched with saturated NH$_4$Cl and diluted with ethyl acetate and washed with H$_2$O, brine, dried over anhydrous MgSO$_4$, filtered and concentrated. Flash chromatography (20% acetone/hexane) afforded methyl (2E)-4-{[4-(4-cyanophenyl)-1,3-thiazol-2-yl]amino}-4-methylpent-2-enoate (0.91 g, 93%) as a white solid. HRMS: calcd for C$_{17}$H$_{17}$N$_3$O$_2$S+H$^+$, 328.11142; found (ESI, [M+H]$^+$), 328.1135; Analytical HPLC: purity 100% at 210-370 nm, 9.9 min; 100% at 252 nm, 9.9 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Step 2: 4-[2-(2,2-Dimethyl-5-oxo-2,5-dihydro-1H-pyrrol-1-yl)-1,3-thiazol-4-yl]benzonitrile Methyl (2E)-4-{[4-(4-cyanophenyl)-1,3-thiazol-2-yl]amino}-4-methylpent-2-enoate (0.15 g, 0.46 mmol), prepared in the previous step, was dissolved in tetrahydrofuran (2 mL) and sodium methoxide (53 mg, 1.0 mmol) was added. The mixture was stirred for 2 h, quenched with saturated NH$_4$Cl, diluted with ethyl acetate, washed with H$_2$O, brine, dried over anhydrous MgSO$_4$, filtered and concentrated. Flash chromatography (20% acetone/hexane) afforded the title compound (0.105 g, 78%) as a white solid. HRMS: calcd for C$_{16}$H$_{13}$N$_3$OS+H$^+$, 296.08521; found (ESI, [M+H]$^+$), 296.0867; Analytical HPLC: purity 99.0% at 210-370 nm, 9.8 min; 97.8% at 304 nm, 9.8 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Example 88

4-[2-(2,2-Dimethyl-5-oxopyrrolidin-1-yl)-1,3-thiazol-4-yl]benzonitrile

Step 1: Methyl 4-{[4-(4-cyanophenyl)-1,3-thiazol-2-yl]amino}-4-methylpentanoate

Methyl (2E)-4-{[4-(4-cyanophenyl)-1,3-thiazol-2-yl]amino}-4-methylpent-2-enoate (0.85 g, 2.6 mmol), prepared in step 1 of Example 87, was dissolved in ethyl acetate (10 mL) and 10% Pd on carbon (0.25 g, 0.20 mmol) was added. The mixture was shaken in a Parr apparatus under 40 psi of hydrogen for 16 h. The mixture was diluted with ethyl acetate, filtered through the Celite™ reagent and concentrated. Flash chromatography (10% acetone/hexane) afforded methyl 4-{[4-(4-cyanophenyl)-1,3-thiazol-2-yl]amino}-4-methylpentanoate (0.81 g, 95%) as a white solid. HRMS: calcd for C$_{17}$H$_{19}$N$_3$O$_2$S+H$^+$, 330.12707; found (ESI, [M+H]$^+$), 330.1292; Analytical HPLC: purity 100% at 210-370 nm, 11.2 min; 100% at 272 nm, 11.2 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Step 2: 4-[2-(2,2-Dimethyl-5-oxopyrrolidin-1-yl)-1,3-thiazol-4-yl]benzonitrile

Methyl 4-{[4-(4-cyanophenyl)-1,3-thiazol-2-yl]amino}-4-methylpentanoate (0.31 g, 0.94 mmol), prepared in the previous step, was dissolved in tetrahydrofuran (18 mL) and sodium bis(trimethylsilyl)amide (1M in tetrahydrofuran, 0.94 mL, 0.94 mmol) was added. The mixture was stirred at 25° C. for 2 h. The reaction was quenched with saturated NH$_4$Cl, diluted with ethyl acetate, washed with H$_2$O, brine, dried over anhydrous MgSO$_4$, filtered and concentrated. Flash chromatography (20% acetone/hexane) afforded the title compound (0.27 g, 97%) as a white solid. HRMS: calcd for C$_{16}$H$_{15}$N$_3$OS+H$^+$, 298.10086; found (ESI, [M+H]$^+$), 298.1; Analytical HPLC: purity 94.8% at 210-370 nm, 9.9 min; 98.2% at 244 nm, 9.9 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Example 89

4-[2-(2,2-Dimethyl-5-oxopyrrolidin-1-yl)-5-fluoro-1, 3-thiazol-4-yl]benzonitrile 4-[2-(2,2-Dimethyl-5-oxopyrrolidin-1-yl)-1,3-thiazol-4-yl]benzonitrile (0.50 g, 1.7 mmol), prepared in step 2 of Example 88, was dissolved in acetonitrile (16 mL) and the Selectfluor® reagent (0.65 g, 1.9 mmol) was added. The mixture was stirred for 16 h, diluted with ethyl acetate, washed with H$_2$O, brine, dried over anhydrous MgSO$_4$, filtered and concentrated. Flash chromatography (10% acetone/hexane) afforded the title compound (0.17 g, 32%) as colorless crystals. HRMS: calcd for C$_{16}$H$_{14}$FN$_3$OS+H$^+$, 316.09144; found (ESI-FT/MS, [M+H]$^{1+}$), 316.0916; Analytical HPLC purity 100% at 210-370 nm, 10.6 min; 98.4% at 296 nm, 10.6 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Example 90

4-[5-Chloro-2-(4,4-dimethyl-2-oxo-1,3-oxazolidin-3-yl)-1,3-thiazol-4-yl]benzonitrile Step 1: 4-{5-Chloro-2-[(1,1-dimethyl-2-oxoethyl) amino]-1,3-thiazol-4-yl}benzonitrile A dry round bottom flask under nitrogen was charged with oxalyl chloride (2M solution in methylene chloride (9.15 mL, 18.3 mmol) and methylene chloride (125 mL) and cooled to −78° C. Dimethylsulfoxide was added dropwise (2.6 mL, 36.6 mmol) and the mixture was stirred for 10 min. A solution of 4-{2-[(hydroxy-1,1-dimethylethyl)amino]-1,3-thiazol-4-yl}benzonitrile (2.5 g, 9.2 mmol), prepared in step 1 of Example 82, in 10 mL of tetrahydrofuran was added and the mixture stirred for 30 min. Triethylamine (7.9 mL, 55 mmol) was added and the mixture was stirred for 20 min and then allowed to warm to 25° C. The mixture was then diluted with methylene chloride and washed with H$_2$O, brine, dried over anhydrous MgSO$_4$, filtered and concentrated. Flash chromatography (20% acetone in hexane) afforded 4-{5-chloro-2-[(1,1-dimethyl-2-oxoethyl)amino]-1,3-thiazol-4-yl}benzonitrile (0.60 g, 22%) as a yellow solid. HRMS: calcd for C$_{14}$H$_{12}$ClN$_3$OS+H$^+$, 306.04623; found (ESI, [M+H]$^+$), 306.0453; Analytical HPLC: purity see MS. MS & UV are same at 210-370 nm; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Step 2: 4-{5-Chloro-2-[(2-hydroxy-1,1-dimethylethyl)amino]-1,3-thiazol-4-yl}benzonitrile 4-{5-Chloro-2-[(1,1-dimethyl-2-oxoethyl)amino]-1,3-thiazol-4-yl}benzonitrile (1.15 g, 3.76 mmol), prepared in the previous step, was dissolved in tetrahydrofuran (20 mL) and cooled to 0° C. Lithium borohydride (2M in tetrahydrofuran; 2.25 mL, 2.5 mmol) was added dropwise and the mixture was stirred for 1 h. The reaction was quenched with saturated NH$_4$Cl, diluted with ethyl acetate and washed with H$_2$O, brine, dried over anhydrous MgSO$_4$, filtered and concentrated. Flash chromatography (20% acetone/hexane) afforded 4-{5-chloro-2-[(2-hydroxy-1,1-dimethylethyl) amino]-1,3-thiazol-4-yl}benzonitrile (1.01 g, 88%) as a white solid. HRMS: calcd for C$_{14}$H$_{14}$ClN$_3$OS+H$^+$, 308.06188; found (ESI, [M+H]$^+$), 308.0612; Analytical HPLC: purity 100% at 210-370 nm, 10.0 min; 100% at 252 nm, 10.0 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Step 3: 4-[5-chloro-2-(4,4-dimethyl-2-oxo-1,3-oxazolidin-3-yl)-1,3-thiazol-4-yl]benzonitrile 4-{5-Chloro-2-[(2-hydroxy-1,1-dimethylethyl)amino]-1, 3-thiazol-4-yl}benzonitrile (0.93 g, 3.0 mmol), prepared in the previous step, was dissolved in methylene chloride (25 mL), triethylamine (4.15 mL, 30 mmol) was added and the mixture was cooled to 0° C. Triphosgene (1.79 g, 6.0 mmol) was added and the mixture was stirred for 2 h. The mixture was then diluted with methylene chloride, washed with 2N HCl, saturated NaHCO$_3$, brine, dried over anhydrous MgSO$_4$, filtered and concentrated. Flash chromatography (10% acetone/hexane) afforded the title compound (220 mg, 22%) as a pale yellow solid. HRMS: calcd for C$_{15}$H$_{12}$ClN$_3$O$_2$S+H$^+$, 334.04115; found (ESI, [M+H]$^+$), 334.04; HPLC purity 100% at 210-370 nm, 10.6 min; 100% at 244 nm, 10.6 min; the Xterra® RP18 column, 3.5µ, 150× 4.6 mm column, 1.2 mL/min, 85/15-5/95 (Ammon. Form. Buff. pH=3.5/ACN+MeOH) for 10 min, hold 4 mm.

Example 91

(4S)-4-[(benzyloxy)methyl]-3-[4-(4-bromophenyl)-1,3-thiazol-2-yl]-1,3-oxazolidin-2-one Step 1: (R)-3-Benzyloxy-2-[4-(4-bromo-phenyl)-thiazol-2-ylamino]-propan-1-ol 2-Bromo-4-(4-bromophenyl)-1,3-thiazole (0.48 g, 1.5 mmol), prepared in step 2 of Example 1, and (R)-2-Amino-3-benzyl-oxy-propan-1-ol (1.1 g, 6.0 mmol) were combined and heated to 160° C. and silver carbonate (0.63 g, 2.3 mmol) was added in four portions over 20 min. The black mixture was heated at 160° C. for an additional 30 min, cooled, and taken up into ethyl acetate. The mixture was washed with water, brine, dried over anhydrous MgSO$_4$, filtered and concentrated. Flash chromatography (0%-20% acetone in hexane) afforded 60 mg of (R)-3-benzyloxy-2-[4-(4-bromo-phenyl)-thiazol-2-ylamino]-propan-1-ol.

Step 2: (4S)-4-[(benzyloxy)methyl]-3-[4-(4-bromophenyl)-1,3-thiazol-2-yl]-1,3-oxazolidin-2-one (R)-3-Benzyloxy-2-[4-(4-bromo-phenyl)-thiazol-2-ylamino]-propan-1-ol (110 mg, 0.26 mmol), prepared in the previous step, was dissolved in methylene chloride (10 mL), cooled to 0° C. and triethylamine (0.36 mL, 2.6 mmol) was added followed by triphosgene (0.19 g, 0.65 mmol). The mixture was stirred for 3 h, diluted with methylene chloride and washed with saturated NaHCO$_3$, brine, dried over anhydrous MgSO$_4$, filtered and concentrated. Flash chromatography (10% acetone in hexane) afforded the title compound (35 mg, 30%). HRMS: calcd for C$_{20}$H$_{17}$BrN$_2$O$_3$S+H$^+$, 445.02160; found (ESI, [M+H]$^+$), 445.0201; Analytical HPLC: purity 100% at 210-370 nm, 11.1 min; 93.8% at 238 nm, 11.1 min; the Xterra® RP18 column, 3.5µ, 150×4.6 mm

Example 92

4-[2-(4,4-dimethyl-2-oxo-1,3-oxazolidin-3-yl)-1,3-oxazol-4-yl]benzonitrile

Step 1: 4-[2-(4,4-dimethyl-2-oxo-1,3-oxazolidin-3-yl)-1,3-oxazol-4-yl]benzonitrile 4-(2-Bromo-acetyl)-benzonitrile (1.2 g, 5.4 mmol) was dissolved in formamide (10 mL) and heated to 110° C. for 72 h. The mixture was cooled, diluted with water and extracted five times with methylene chloride. The organics were combined, washed with water, brine, dried over anhydrous MgSO$_4$, filtered and concentrated. Flash chromatography (5%-10% acetone in hexane) afforded 4-(1,3-oxazol-4-yl)benzonitrile (0.16 g, 17%) as a white solid. Analytical HPLC: purity 100% at 270 nm, 6.8 min; 100% at 210-370 nm, 6.8 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Step 2: 4-(2-iodo-1,3-oxazol-4-yl)benzonitrile 4-(1,3-Oxazol-4-yl)benzonitrile (130 mg, 0.76 mmol), prepared in the previous step, was dissolved in tetrahydrofuran (10 mL) and cooled to −78° C. Sodium bis(trimethylsilyl)amide (1M solution in tetrahydrofuran) (0.84 mL, 0.84 mmol) was added dropwise and the mixture was stirred for 30 min. A solution of iodine (0.23 g, 0.91 mmol) in tetrahydrofuran (5 mL) was added dropwise and the mixture was stirred at −78° C. for 1 h. The mixture was poured into a 1:1 mixture of aqueous sodium bicarbonate and sodium sulfite and extracted with methylene chloride. The organics were combined, washed with water, brine, dried over anhydrous MgSO$_4$, filtered and concentrated. Flash chromatography (10% acetone in hexane) afforded 4-(2-iodo-1,3-oxazol-4-yl)benzonitrile (154 mg, 69%) as a white solid. HRMS: calcd for C$_{10}$H$_5$I$_1$N$_2$O, 295.94466; found (EI, M$^+$), 295.9436; Analytical HPLC: purity 99.3% at 274 nm, 8.9 min; 99.5% at 210-370 nm, 8.9 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Step 3: 4-[2-(4,4-dimethyl-2-oxo-1,3-oxazolidin-3-yl)-1,3-oxazol-4-yl]benzonitrile A 5 mL flask was charged with 4,4-dimethyl-oxazolidin-2-one (1.0 g, 8.7 mmol) and sodium hydride (60% wt suspension in mineral oil) (40 mg, 1.2 mmol) was added and the mixture was stirred for 20 min. 4-(2-Iodo-1,3-oxazol-4-yl)benzonitrile (0.257 g, 0.87 mmol), prepared in the previous step, was added and the mixture was heated to 170° C. for 2 h then cooled and diluted with ethyl acetate. The organics were combined, washed with water, brine, dried over anhydrous MgSO$_4$, filtered and concentrated. Flash chromatography (15% acetone in hexane) afforded the title compound (9 mg, 4%). HRMS: calcd for C$_{15}$H$_{13}$N$_3$O$_3$+H$^+$, 284.10297; found (ESI, [M+H]$^+$), 284.1024; Analytical HPLC: purity 95.3% at 210-370 nm, 8.1 min; 98.3% at 278 nm, 8.1 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Example 93

3-[3-(4-Bromophenyl)-1,2,4-thiadiazol-5-yl]-4,4-dimethyl-1,3-oxazolidin-2-one

Step 1: 4-Bromobenzenecarboximidamide hydrochloride

Sodium methoxide (0.81 g, 15 mmol) was dissolved in methanol (150 mL) and 4-bromobenzonitrile (27.3 g, 150 mmol) was added and the mixture was stirred at 25° C. for 24 h. Solid ammonium chloride (8.1 g, 150 mmol) was added and the mixture was stirred for an additional 24 h. The mixture was filtered, the solid was washed with methanol and ether, and the filtrate was combined and concentrated. The white residue was collected and washed thoroughly with ether and dried under vacuum to give 4-bromobenzenecarboximidamide hydrochloride (16 g, 54%) as a white solid. HRMS: calcd for C$_7$H$_7$BrN$_2$+H$^+$, 198.98654; found (ESI, [M+H]$^+$), 198.9868; Analytical HPLC: purity 98.4% at 246 nm, 3.4 min; 97.8% at 210-370 nm, 3.4 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Step 2: 3-(4-Bromophenyl)-5-chloro-1,2,4-thiadiazole

4-Bromobenzenecarboximidamide hydrochloride (1.00 g, 4.25 mmol), prepared in the previous step, was suspended in methylene chloride (25 mL) and triethylamine (6.1 mL, 42.5 mmol) was added and the mixture was cooled to 0° C. Perchloromethyl mercaptan (0.47 g, 4.25 mmol) was added slowly, the mixture was stirred for 30 min, warmed to 25° C. and stirred 4 h. The mixture was diluted with methylene chloride, filtered through the Celite™ reagent, and concentrated. Flash chromatography (2% acetone in hexane) afforded 3-(4-bromophenyl)-5-chloro-1,2,4-thiadiazole (327 mg, 28%). HRMS: calcd for C$_8$H$_4$BrClN$_2$S, 273.89671; found (EI, M$^+$.), 273.8968; Analytical HPLC: purity 100% at 210-370 nm, 11.2 min; 100% at 272 nm, 11.2 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Step 3: 2-{[3-(4-Bromophenyl)-1,2,4-thiadiazol-5-yl]amino}-2-methylpropan-1-ol 3-(4-Bromophenyl)-5-chloro-1,2,4-thiadiazole (2.0 g, 7.3 mmol), prepared in the previous step, was dissolved in 2-amino-2-methylpropanol and heated to 125° C. for 16 h. The mixture was cooled, diluted with ethyl acetate, washed with water, brine, dried over anhydrous MgSO$_4$, filtered and concentrated. Flash chromatography (10% acetone in hexane) afforded 2-{[3-(4-bromophenyl)-1,2,4-thiadiazol-5-yl]amino}-2-methylpropan-1-ol (0.85 g, 35%) as a pale yellow solid. HRMS: calcd for C$_{12}$H$_{14}$BrN$_3$OS+H$^+$, 328.01137; found (ESI, [M+H]$^+$), 328.0113; Analytical HPLC: purity 100% at 210-370 nm, 10.0 min; 100% at 252 nm, 10.0 min; the Xterra® RP18 column, 3.5μ, 150×4.6 mm column, 1.2 mL/min, 85/15-5/95 (Ammon. Form. Buff. pH 3.5/ACN+MeOH) for 10 min, hold 4 min.

Step 4: 3-[3-(4-bromophenyl)-1,2,4-thiadiazol-5-yl]-4,4-dimethyl-1,3-oxazolidin-2-one 2-{[3-(4-Bromophenyl)-1,2,4-thiadiazol-5-yl]amino}-2-methylpropan-1-ol (0.80 g, 2.4 mmol), prepared in the previous step, was dissolved in methylene chloride (20 mL), triethylamine (3.3 mL, 24 mmol) was added, and the mixture was cooled to 0° C. Triphosgene (1.8 g, 6.1 mmol) was added and the mixture was stirred for 2.5 h. The mixture was then diluted with methylene chloride and washed with 2N HCl, saturated NaHCO$_3$, brine, dried over anhydrous MgSO$_4$, filtered and concentrated. Flash chromatography (7.5% acetone/hexane) afforded the title compound (730 mg, 86%). Analytical HPLC: purity 100% at 210-370 nm, 11.0 min; 100% at 246 nm, 11.0 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 94

4-[5-(4,4-dimethyl-2-oxo-1,3-oxazolidin-3-yl)-1,2,4-thiadiazol-3-yl]benzonitrile 3-[3-(4-bromophenyl)-1,2,4-thiadiazol-5-yl]-4,4-dimethyl-1,3-oxazolidin-2-one (0.67 g, 1.9 mmol), prepared in step 4 of Example 93, was dissolved in dimethylformamide (19 mL). Zinc cyanide (0.132 g, 1.14 mmol) was added, the mixture was purged with nitrogen for 15 min, and then tetrakis(triphenylphosphine)palladium (0.11 g, 0.095 mmol) was added. The mixture was heated to 120° C. for 2 h, additional tetrakis(triphenylphosphine)palladium (0.11 g, 0.095 mmol) was added and stirring was continued for 45 min. The mixture was cooled, diluted with ethyl acetate, washed with water, brine, dried over anhydrous MgSO$_4$, filtered and concentrated. Flash chromatography (10% acetone in hexane) afforded the title compound (0.48 g, 84%) as a white solid. Analytical HPLC: HPLC purity 100% at 210-370 nm, 9.7 min; 100% at 248 nm, 9.7 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 95

4,4-Dimethyl-3-{4-[4-(trifluoromethyl)phenyl]-1,3-thiazol-2-yl}-1,3-oxazolidin-2-one General Procedure for Palladium Catalyzed Biaryl Coupling:
A vial under nitrogen was charged with 2-(4,4-dimethyl-2-oxo-1,3-oxazolidin-3-yl)-1,3-thiazol-4-yl trifluoromethanesulfonate (100 mg, 0.28 mmol), [4-(trifluoromethyl)phenyl]-boronic acid (58 mg, 0.31 mmol), and tetrakis(triphenylphosphine)palladium (65 mg, 0.056 mmol) followed by tetrahydrofuran (0.6 mL) and triethylamine (0.13 mL, 0.92 mmol). The mixture was stirred for 16 h, diluted with tetrahydrofuran, passed through a plug of silica gel (2 g) and concentrated. The crude product was purified by reverse phase HPLC to give the title compound. HRMS: calcd for $C_{15}H_{13}F_3N_2O_2S+H^+$, 343.07226; found (ESI-FT/MS, [M+H]$^{1+}$), 343.0725; Analytical HPLC: purity 100% at 210-370 nm, 10.7 min; 100% at 268 nm, 10.7 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min

Example 96

4,4-Dimethyl-3-{4-[3-(trifluoromethyl)phenyl]-1,3-thiazol-2-yl}-1,3-oxazolidin-2-one This compound was prepared from [3-(trifluoromethyl)phenyl]boronic acid according to the general procedure of Example 95. HRMS: calcd for $C_{15}H_{13}F_3N_2O_2S+H^+$, 343.07226; found (ESI-FT/MS, [M+H]$^{1+}$), 343.0726; Analytical HPLC: purity 100% at 210-370 nm, 10.7 min; 100% at 268 nm, 10.7 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 97

4,4-Dimethyl-3-{4-[4-(trifluoromethoxy)phenyl]-1,3-thiazol-2-yl}-1,3-oxazolidin-2-one This compound was prepared from [4-(trifluoromethoxy)phenyl]boronic acid according to the general procedure of Example 95. HRMS: calcd for $C_{15}H_{13}F_3N_2O_3S+H^+$, 359.06717; found (ESI-FT/MS, [M+H]$^{1+}$), 359.0673; Analytical HPLC: purity 100% at 210-370 nm, 10.8 min; 100% at 266 nm, 10.8 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 98

3-[4-(4-Methoxyphenyl)-1,3-thiazol-2-yl]-4,4-dimethyl-1,3-oxazolidin-2-one

This compound was prepared from [4-(methoxy)phenyl] boronic acid according to the general procedure of Example 95. HRMS: calcd for $C_{15}H_{16}N_2O_3S+H^+$, 305.09544; found (ESI-FT/MS, [M+H]$^{1+}$), 305.0956; Analytical HPLC: purity 96.7% at 210-370 nm, 9.9 min; 94.3% at 268 nm, 9.9 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 99

3-[4-(3-Methoxyphenyl)-1,3-thiazol-2-yl]-4,4-dimethyl-1,3-oxazolidin-2-one

This compound was prepared from [3-(methoxy)phenyl] boronic acid according to the general procedure of Example 95. HRMS: calcd for $C_{15}H_{16}N_2O_3S+H^+$, 305.09544; found (ESI-FT/MS, [M+H]$^{1+}$), 305.0956; Analytical HPLC: purity 100% at 210-370 nm, 9.9 min; 100% at 266 nm, 9.9 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Example 100

3-[4-(2-Methoxyphenyl)-1,3-thiazol-2-yl]-4,4-dimethyl-1,3-oxazolidin-2-one

This compound was prepared from [2-(methoxy)phenyl] boronic acid according to the general procedure of Example 95. HRMS: calcd for $C_{15}H_{16}N_2O_3S+H^+$, 305.09544; found (ESI-FT/MS, [M+H]$^{1+}$), 305.0956; Analytical HPLC: purity 100% at 210-370 nm, 10.1 min; 98.9% at 262 nm, 10.1 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 101

4,4-Dimethyl-3-[4-(2,4,6-trifluorophenyl)-1,3-thiazol-2-yl]-1,3-oxazolidin-2-one This compound was prepared from [2,4,6-Trifluorophenyl]boronic acid according to the general procedure of Example 95. Analytical HPLC: purity 100% at 210-370 nm, 10.1 min; 97.7% at 258 nm, 10.1 min; the Xterra® RP18

Example 102

3-{4-[3-(Ethylsulfonyl)phenyl]-1,3-thiazol-2-yl}-4,4-dimethyl-1,3-oxazolidin-2-one This compound was prepared from [3-ethanesulfonylphenyl]boronic acid according to the general procedure of Example 95. HRMS: calcd for $C_{16}H_{18}N_2O_4S_2+H^+$, 367.07807; found (ESI-FT/MS, [M+H]$^{1+}$), 367.0784; Analytical HPLC: purity 100% at 210-370 nm, 8.8 min; 100% at 270 nm, 8.8 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Example 103

{4-[2-(4,4-Dimethyl-2-oxo-1,3-oxazolidin-3-yl)-1,3-thiazol-4-yl]phenyl}acetonitrile This compound was prepared from [4-cyanomethylphenyl]boronic acid according to the general procedure of Example 95. HRMS: calcd for $C_{16}H_{15}N_3O_2S+H^+$, 314.09577; found (ESI-FT/MS, [M+H]$^{1+}$), 314.096; Analytical HPLC: purity 87.8% at 210-370 nm, 9.1 min; 93.9% at 268 nm, 9.1 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Example 104

3-[4-(3-Furyl)-1,3-thiazol-2-yl]-4,4-dimethyl-1,3-oxazolidin-2-one

This compound was prepared from furan-3-boronic acid according to the general procedure of Example 95. HRMS: calcd for $C_{12}H_{12}N_2O_3S+H^+$, 265.06414; found (ESI-FT/MS, [M+H]$^1$+), 265.0643; Analytical HPLC: purity 95.7% at 210-370 nm, 9.1 min; 92.9% at 276 nm, 9.1 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Example 105

3-[4-(1H-Indol-5-yl)-1,3-thiazol-2-yl]-4,4-dimethyl-1,3-oxazolidin-2-one

This compound was prepared from indole-5-boronic acid according to the general procedure of Example 95. HRMS: calcd for $C_{16}H_{15}N_3O_2S+H^+$, 314.09577; found (ESI-FT/MS, [M+H]$^{1+}$), 314.096; Analytical HPLC: purity 97.5% at 210-370 nm, 9.6 min; 97.4% at 242 nm, 9.6 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 mm.

Example 106

3-[4-(4-Acetylphenyl)-1,3-thiazol-2-yl]-4,4-dimethyl-1,3-oxazolidin-2-one

This compound was prepared from 4-acetyl-phenyl-boronic acid according to the general procedure of Example 95. HRMS: calcd for $C_{16}H_{16}N_2O_3S+H^+$, 317.09544; found (ESI-FT/MS, [M+H]$^{1+}$), 317.0961; Analytical HPLC: purity 100% at 210-370 nm, 9.4 min; 100% at 308 nm, 9.4 min; the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Example 107

3-[4-(3-Acetylphenyl)-1,3-thiazol-2-yl]-4,4-dimethyl-1,3-oxazolidin-2-one

This compound was prepared from 3-acetyl-phenyl-boronic acid according to the general procedure of Example 95. HRMS: calcd for $C_{16}H_{16}N_2O_3S+H^+$, 317.09544; found (ESI-FT/MS, [M+H]$^{1+}$), 317.0958; Analytical HPLC: purity 98.2% at 210-370 nm, 9.4 min; 98.8% at 228 nm, 9.4 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Example 108

3-[4-(3,4-Dimethoxyphenyl)-1,3-thiazol-2-yl]-4,4-dimethyl-1,3-oxazolidin-2-one

This compound was prepared from 3,4-dimethoxy-phenyl-boronic acid according to the general procedure of Example 95. HRMS: calcd for $C_{16}H_{18}N_2O_4S+H^+$, 335.10600; found (ESI-FT/MS, [M+H]$^{1+}$), 335.1064; Analytical HPLC: purity 100% at 210-370 nm, 9.2 min; 100% at 268 nm, 9.2 min; the Xterra® RP18 column, 3.5µ, 150×4.6 mm column, 1.2 mL/min, 85/15-5/95 (Ammon. Form. Buff. pH=3.5/ACN+MeOH) for 10 min, hold 4 min.

Example 109

3-[4-(4-Chloro-3-fluorophenyl)-1,3-thiazol-2-yl]-4,4-dimethyl-1,3-oxazolidin-2-one Step 1: 1-(4-Chloro-3-fluorophenyl)ethanol Methylmagnesium bromide (22.5 mL, 31.5 mmol; 1.4 M solution in toluene/tetrahydrofuran) was added dropwise to a solution of 4-chloro-3-fluorobenzaldehyde (5.0 g, 31.5 mmol) in 100 mL of dry tetrahydrofuran at −78° C. over 15 min. The reaction was allowed to warm to room temperature and stirred overnight. The reaction mixture was poured into saturated NH$_4$Cl (100 mL). The aqueous layer was extracted with diethyl ether (3×150 mL). The organic layer was dried over anhydrous sodium sulfate, filtered and concentrated in vacuo to give 1-(4-chloro-3-fluorophenyl)ethanol (5.50 g, 100%) as a yellow oil which was used in the next step without further purification, MS (ES) m/z 175 [M+H$^+$].

Step 2: 1-(4-chloro-3-fluorophenyl)ethanone 1-(4-Chloro-3-fluorophenyl)ethanol (5.50 g, 31.5 mmol), prepared in the previous step, in dry methylene chloride (25 mL) was added dropwise to a mixture of pyridinium chlorochromate (10.1 g, 46.8 mmol) and the Celite™ reagent (9 g) in methylene chloride (120 mL) at 0° C. The resulting solution was allowed to warm to room temperature and stirred overnight. The reaction solution was diluted with diethyl ether (50 mL) and filtered. The filtrate was concentrated in vacuo to give 5.0 g of a dark brown oil as crude product. The crude product was purified on silica gel using a stepwise gradient of 5% to 10% ethyl acetate-hexane to give 1-(4-chloro-3-fluorophenyl)ethanone (3.4 g, 63%) as desired product, MS (ES) m/z 173 [M+H$^+$].

Step 3: 2-Bromo-1-(4-chloro-3-fluoro-phenyl)-ethanone

To a solution of 1-(4-chloro-3-fluorophenyl)ethanone (3.4 g, 19.7 mmol), prepared in the previous step, in methylene chloride:methanol (1:3) was added tetrabutylammonium tribromide (9.5 g, 19.7 mmol) in portions. The reaction was monitored by TLC (3:1 hexane:ethyl acetate) until the starting material was consumed. The reaction solution was concentrated in vacuo and the residue was partitioned between diethyl ether and water. The layers were separated and the organic layer was dried over anhydrous sodium sulfate, filtered and concentrated in vacuo to give 4.2 g of crude product. The crude product was purified on silica gel using 5% ethyl acetate:hexane to give 2-bromo-1-(4-chloro-3-fluoro-phenyl)-ethanone (3.4 g, 69%) as desired product, MS (ES) m/z 252 [M+H$^+$].

Step 4: 1-(4-Chloro-3-fluoro-phenyl)-2-thiocyanato-ethanone

In the same manner as described in step 4 of Example 78, using 2-bromo-1-(4-chloro-3-fluoro-phenyl)-ethanone (2.7 g, 10.7 mmol), prepared in the previous step, and potassium isothiocyanate (1.25 g, 12.8 mmol) in ethanol (150 mL) the crude product was collected by suction filtration to give 1-(4-chloro-3-fluoro-phenyl)-2-thiocyanato-ethanone (2.47 g, 100%), which was used in the next step without further purification. MS (ES) m/z 230[M+H$^+$].

Step 5: 2-Bromo-4-(4-chloro-3-fluorophenyl)-1,3-thiazole

In the same manner as described in step 5 of Example 78, using 1-(4-chloro-3-fluoro-phenyl)-2-thiocyanato-ethanone (2.45 g, 10.7 mmol), prepared in the previous step, and hydrogen bromide (30% in acetic acid, 16 mL), the solid was collected by suction filtration to give 2-bromo-4-(4-chloro-3-fluorophenyl)-1,3-thiazole (2.1 g, 68%). The material was used without further purification, MS (ES) m/z 293[M+H$^+$].

Step 6: 2-[4-(4-Chloro-3-fluoro-phenyl)-thiazol-2-ylamino]-2-methyl-propan-1-ol 2-Bromo-4-(4-chloro-3-fluorophenyl)-1,3-thiazole (900 mg, 3.07 mmol), prepared in the previous step, and 2-amino-2-methyl-propan-1-ol (900 mL, 9.21 mmol) were stirred in a sealed tube at 150° C. for 3 days. The reaction solution was cooled to room temperature and concentrated in vacuo to give 1.0 g of a dark brown oil. The crude product was purified on silica gel using a stepwise gradient of 1%-6% methanol:methylene chloride to give 2-[4-(4-chloro-3-fluoro-phenyl)-thiazol-2-ylamino]-2-methyl-propan-1-ol (810 mg, 88%) as the desired product. MS (ES) m/z 301 [M+H$^+$].

Step 7: 3-[4-(4-chloro-3-fluorophenyl)-1,3-thiazol-2-yl]-4,4-dimethyl-1,3-oxazolidin-2-one In the same manner as described in step 7 of Example 78, using 2-[4-(4-chloro-3-fluoro-phenyl)-thiazol-2-ylamino]-2-methyl-propan-1-ol (810 mg, 2.66 mmol), prepared in the previous step, triphosgene (946 mg, 3.19 mmol) and diisopropylethyl amine (1.1 mL) in 20 mL of methylene chloride, the title compound was isolated (125 mg, 14%) after purification on silica gel using 6:1 hexane:ethyl acetate as the eluent. mp 140-142° C.

Example 110

4-[2-(2,2-Dimethyl-1,3-oxazolidin-3-yl)-1,3-thiazol-4-yl]benzonitrile

Step 1: (2-Hydroxy-ethyl)-thiourea

2-Aminoethanol (1.0 mL, 17.1 mmol) in 10 mL of dry tetrahydrofuran was added dropwise to a solution of benzoyl isothiocyanate (2.8 g, 17.1 mmol) in 35 mL of dry tetrahydrofuran at room temperature. The solution was heated to reflux for 1 h. The reaction was cooled to room temperature and concentrated in vacuo. The resulting residue was dissolved in 50 mL of tetrahydrofuran and 17 mL of 1M LiOH and stirred overnight. The mixture was concentrated and the crude residue (2.0 g, 100%) was dissolved in ethanol (50 mL) and used in the next step.

Step 2: 4-{2-[(2-Hydroxyethyl)amino]-1,3-thiazol-4-yl}benzonitrile

In the same manner as described in step 3 of Example 81, a solution of 4-(2-bromo-acetyl)-benzonitrile (3.8 g, 17.1 mmol) and (2-hydroxy-ethyl)-thiourea, prepared in the previous step, in 50 mL of ethanol was heated at reflux for 2 h. The reaction was concentrated to a residue. The residue was dissolved in ethyl acetate and washed with saturated NaHCO$_3$. The organic layer was dried over anhydrous MgSO$_4$, filtered and concentrated in vacuo to give 6.2 g of crude product. The crude product was purified on silica gel using a stepwise gradient of 3:1 to 2:1 hexane:ethyl acetate to give 4-{2-[(2-hydroxyethyl)amino]-1,3-thiazol-4-yl}benzonitrile (1.6 g, 39%), mp 80-82° C.

Step 3: 4-[2-(2,2-Dimethyl-1,3-oxazolidin-3-yl)-1,3-thiazol-4-yl]benzonitrile A mixture of 4-{2-[(2-hydroxyethyl)amino]-1,3-thiazol-4-yl}benzonitrile (1.0 g, 4.0 mmol), prepared in the previous step, 2,2-dimethoxypropane (7.2 mL, 61.2 mmol) and a catalytic amount of p-toluenesulfonic acid in toluene (90 mL) was heated at 90° C. overnight. The reaction was cooled and concentrated to a residue. Purification of the crude product on silica gel using 5% ethyl acetate:hexane as the eluent gave 480 mg of impure product. Final purification by reverse phase HPLC using an isocratic system of 80:20 acetonitrile:water gave the title compound (107 mg, 10%), mp 108-111° C.

Example 111

2-(4,4-Dimethyl-2-oxo-1,3-oxazolidin-3-yl)-4,5-dihydronaphtho[1,2-d][1,3]thiazole-7-carbonitrile

Step 1: 5-Oxo-5,6,7,8-tetrahydronaphthalen-2-yl trifluoromethanesulfonate

To a solution of 6-hydroxy-3,4-dihydro-2H-naphthalen-1-one (6.3 g, 39.1 mmol) in dry pyridine (30 mL) at 0° C. was added trifluoromethanesulfonic anhydride (7.3 mL, 43.0 mmol) over a few minutes. The solution was warmed to room temperature and stirred for 3 h. The reaction was poured into 1N HCl and diluted with ethyl acetate. The layers were separated and the aqueous layer was extracted with ethyl acetate. The combined organic layers were dried over anhydrous sodium sulfate, filtered and concentrated in vacuo to give 5-oxo-5,6,7,8-tetrahydronaphthalen-2-yl trifluoromethanesulfonate (11.5 g, 100%). The crude product was used without purification. MS (ES) m/z 295 [M+H]$^+$.

Step 2: 5-Oxo-5,6,7,8-tetrahydro-naphthalene-2-carbonitrile

A mixture of 5-oxo-5,6,7,8-tetrahydronaphthalen-2-yl trifluoromethanesulfonate (11.5 g, 39.0 mmol), prepared in the previous step, and zinc cyanide (2.7 g, 23.5 mmol) in dry dimethylformamide (100 mL) was degassed and put under a nitrogen atmosphere. Tetrakis(triphenylphosphine)palladium(0) (1.7 g, 1.5 mmol) was added and the mixture again degassed and put under a nitrogen atmosphere. The mixture was stirred at 135° C. overnight. An additional 171 mg of tetrakis(triphenylphosphine)palladium(0) was added and the reaction stirred for another 4 h. The reaction mixture was filtered through the Celite™ reagent and rinsed with ethyl acetate. The filtrate was washed with water. The layers were separated and the organic layer was dried over anhydrous sodium sulfate. The organic layer was filtered and concentrated in vacuo to give 8.1 g of crude product. Purification of the crude product on silica gel using a step-wise gradient of 5% to 15% ethyl acetate:hexane as the eluent gave 5-oxo-5,6,7,8-tetrahydro-naphthalene-2-carbonitrile (2.8 g, 41%), MS (ES) m/z 172 [M+H]$^+$.

Step 3: 6-Bromo-5-oxo-5,6,7,8-tetrahydronaphthalene-2-carbonitrile

Bromine (0.8 mL, 15.7 mmol) was added to a solution of 5-oxo-5,6,7,8-tetrahydro-naphthalene-2-carbonitrile (2.7 g, 15.7 mmol), prepared in the previous step, in dry methylene chloride (55 mL) at 0° C. The reaction was warmed to room temperature. After 2 h, the reaction was diluted with methylene chloride and washed with 5% sodium thiosulfate and brine. The organic layer was dried over anhydrous sodium sulfate, filtered and concentrated in vacuo to give 4.3 g of crude product. Purification of the crude product on silica gel using 10% ethyl acetate:hexane as the eluent gave 6-bromo-5-oxo-5,6,7,8-tetrahydronaphthalene-2-carbonitrile (3.2 g, 81%), MS (ES) m/z 251 [M+H]$^+$.

Step 4: 2-[(2-Hydroxy-1,1-dimethylethyl)amino]-4,5-dihydronaphtho[1,2-d][1,3]thiazole-7-carbonitrile In the same manner as described in step 3 of Example 81, replacing 4-(2-bromoacetyl)-2-fluorobenzonitrile with 6-bromo-5-oxo-5,6,7,8-tetrahydronaphthalene-2-carbonitrile, prepared in the previous step, and purification on silica using a stepwise gradient of 8:1 to 3:1 hexane:ethyl acetate as the eluent gave 2-[(2-hydroxy-1,1-dimethylethyl)amino]-4,5-dihydronaphtho[1,2-d][1,3]thiazole-7-carbonitrile (2.7 g, 70%). mp 121-123° C.

Step 5: 2-(4,4-Dimethyl-2-oxo-1,3-oxazolidin-3-yl)-4,5-dihydronaphtho[1,2-d][1,3]thiazole-7-carbonitrile In the same manner as described in step 4 of Example 81, replacing 2-fluoro-4-{2-[(2-hydroxy-1,1-dimethyl-ethyl)amino]-1,3-thiazol-4-yl}benzonitrile with 2-[(2-hydroxy-1,1-dimethylethyl)amino]-4,5-dihydronaphtho[1,2-d][1,3]thiazole-7-carbonitrile, prepared in the previous step, and purification of the crude product on silica using a stepwise gradient of 6:1 to 1:1 hexane:ethyl acetate as the eluent gave the title compound (2.7 g, 93%), mp>230° C. (dec.).

Example 112

4-[5-(2-Oxo-1,3-oxazolidin-3-yl)-3-thienyl]benzonitrile

Step 1: 3-(4-Bromo-thiophen-2-yl)-oxazolidin-2-one

N,N-Dimethylethylamine (0.22 mL, 2.0 mmol), 2,4-dibromothiophene (5.0 g, 20.6 mmol) and oxazolidinone (2.1 g, 24.8 mmol) were added to a mixture of copper(I) iodide (0.39 g, 2.0 mmol) and cesium carbonate (13.4 g, 41.3 mmol) in dry dioxane under nitrogen. The reaction mixture was stirred at 110° C. for 16 h. The reaction was filtered through the Celite™ reagent and rinsed with methylene chloride. The filtrate was concentrated in vacuo to a residue. Purification of the crude product on silica gel using a stepwise gradient of 6:1 to 3:1 hexane:ethyl acetate as the eluent gave 3-(4-bromothiophen-2-yl)-oxazolidin-2-one (790 mg, 15%) as the desired product contaminated with 10% of the 3-(5-bromothiophen-3-yl)-oxazolidin-2-one isomer. MS (ES) m/z 249 [M+H]$^+$.

Step 2: 4-[5-(2-Oxo-1,3-oxazolidin-3-yl)-3-thienyl]benzonitrile

The mixture prepared in the previous step was stirred in ethyl acetate containing 10% Pd/C for 15 min, filtered and concentrated before using in the coupling step. This isomeric mixture (0.79 g, 3.1 mmol), 4-cyanophenyl boronic acid (0.84 g, 5.7 mmol), potassium fluoride (0.60 g, 10.5 mmol), and tris(dibenzylideneacetone)dipalladium (0) (0.07 g, 0.08 mmol) were placed in a dry round bottom flask under a stream of nitrogen. Tetrahydrofuran (50 mL) was added and the mixture was stirred for 5 min. Tri-t-butylphosphine (0.47 mL, 0.16 mmol) was added and the mixture was stirred for 16 h. The reaction was diluted with ethyl acetate and filtered through a silica gel plug. The plug was rinsed with ethyl acetate and the filtrate was concentrated to give 7.9 g of crude product. Purification of the crude product on silica gel using a stepwise gradient of 5:1 to 1:1 hexane:ethyl acetate as the eluent gave 0.65 g of a mixture of isomers. The mixture was separated using reverse phase HPLC (the Xterra® MSC18 instrument, 5μ, 4.6×150 mm, 60%:40% methanol:water, isocratic). The appropriate fractions were concentrated to give the title compound (0.42 g, 49%), mp 196-199° C.

Example 113

2-(4,4-Dimethyl-2-oxo-1,3-oxazolidin-3-yl)naphtho[1,2-d][1,3]thiazole-7-carbonitrile 2-(4,4-Dimethyl-2-oxo-1,3-oxazolidin-3-yl)-4,5-dihydronaphtho[1,2-d][1,3]thiazole-7-carbonitrile (0.65 g, 2.0 mmol), prepared in step 5 of Example 111, N-bromosuccinamide (0.39 g, 2.2 mmol) and a catalytic amount of 2,2'-azobis(2-methylproprionitrile) were stirred in carbontetrachloride (68 mL) at reflux for 4 h. The reaction was diluted with ethyl acetate and washed with 10% sodium thiosulfate. The layers were separated and the organic layer was dried over anhydrous MgSO$_4$, filtered and concentrated to give 0.64 g of crude product. Purification of the crude product on silica gel using a stepwise gradient of 6:1 to 1:1 hexane:ethyl acetate as the eluent gave 0.35 g of product that contained an impurity. Recrystallization from ethyl acetate afforded the title compound (0.02 g, 3%), mp>230° C.

Example 114

3-[4-(4-Chlorophenyl)-1,3-thiazol-2-yl]-4,4-dimethyl-1,3-oxazolidin-2-one

This compound was prepared in the same manner as described in Example 95, replacing the [4-(trifluoromethyl)phenyl]-boronic acid with 4-chlorophenyl boronic acid. The crude product was purified by reverse phase HPLC to give the title compound. HRMS: calcd for $C_{14}H_{13}ClN_2O_2S+H^+$, 309.04590; found (ESI, $[M+H]^+$), 309.0465.

Example 115

3-[4-(4-Fluorophenyl)-1,3-thiazol-2-yl]-4,4-dimethyl-1,3-oxazolidin-2-one

This compound was prepared in the same manner as described in Example 95, replacing the [4-(trifluoromethyl)phenyl]-boronic acid with 4-fluorophenyl boronic acid. The crude product was purified by reverse phase HPLC to give the title compound. HRMS: calcd for $C_{14}H_{13}FN_2O_2S+H^+$, 293.07545; found (ESI, $[M+H]^+$), 293.0763.

Example 116

3-[4-(3,5-Dichlorophenyl)-1,3-thiazol-2-yl]-4,4-dimethyl-1,3-oxazolidin-2-one

This compound was prepared in the same manner as described in Example 95, replacing the [4-(trifluoromethyl)phenyl]-boronic acid with 3,5-dichlorobenzeneboronic acid. The crude product was purified by reverse phase HPLC to give the title compound. HRMS: calcd for $C_{14}H_{12}Cl_2N_2O_2S+H^+$, 343.00693; found (ESI, $[M+H]^+$), 343.0059.

Example 117

3-[4-(3-Chloro-4-fluorophenyl)-1,3-thiazol-2-yl]-4,4-dimethyl-1,3-oxazolidin-2-one This compound was prepared in the same manner as described in Example 95, replacing the [4-(trifluoromethyl)phenyl]-boronic acid with 3-chloro-4-fluorobenzeneboronic acid. The crude product was purified by reverse phase HPLC to give the title compound. HRMS: calcd for $C_{14}H_{12}ClFN_2O_2S+H^+$, 327.03648; found (ESI, $[M+H]^+$), 327.0367.

Example 118

3-[4-(2,4-Dichlorophenyl)-1,3-thiazol-2-yl]-4,4-dimethyl-1,3-oxazolidin-2-one

This compound was prepared in the same manner as described in Example 95, replacing the [4-(trifluoromethyl)phenyl]-boronic acid with 2,4-dichlorophenylboronic acid. The crude product was purified by reverse phase HPLC to give the title compound. HRMS: calcd for $C_{14}H_{12}Cl_2N_2O_2S+H^+$, 343.00693; found (ESI, $[M+H]^+$), 343.0064.

Example 119

3-[4-(3,4-Dichlorophenyl)-1,3-thiazol-2-yl]-4,4-dimethyl-1,3-oxazolidin-2-one

This compound was prepared in the same manner as described in Example 95, replacing the [4-(trifluoromethyl)phenyl]-boronic acid with 3,4-dichlorobenzeneboronic acid. The crude product was purified by reverse phase HPLC to give the title compound. mp 134-137° C.

Example 120

4,4-Dimethyl-3-(4-phenyl-1,3-thiazol-2-yl)-1,3-oxazolidin-2-one

This compound was prepared in the same manner as described in Example 95, replacing the [4-(trifluoromethyl)phenyl]-boronic acid with phenylboronic acid. The crude product was purified by reverse phase HPLC to give the title compound. mp 94-97° C.

Example 121

4,4-Dimethyl-3-[4-(4-methylphenyl)-1,3-thiazol-2-yl]-1,3-oxazolidin-2-one

This compound was prepared in the same manner as described in Example 95, replacing the [4-(trifluoromethyl)phenyl]-boronic acid with 4-methylbenzeneboronic acid. The crude product was purified by reverse phase HPLC to give the title compound. HRMS: calcd for $C_{15}H_{16}N_2O_2S+H^+$, 289.10052; found (ESI, $[M+H]^+$), 289.1017.

Example 122

4,4-Dimethyl-3-[4-(2-naphthyl)-1,3-thiazol-2-yl]-1,3-oxazolidin-2-one

This compound was prepared in the same manner as described in Example 95, replacing the [4-(trifluoromethyl)phenyl]-boronic acid with naphthalene-2-boronic acid. The crude product was purified by reverse phase HPLC to give the title compound. HRMS: calcd for $C_{18}H_{16}N_2O_2S+H^+$, 325.10052; found (ESI, $[M+H]^+$), 325.0999.

Example 123

4,4-Dimethyl-3-[4-(2-nitrophenyl)-1,3-thiazol-2-yl]-1,3-oxazolidin-2-one

This compound was prepared in the same manner as described in Example 95, replacing the [4-(trifluoromethyl)phenyl]-boronic acid with 2-nitrophenylboronic acid. The crude product was purified by reverse phase HPLC to give the title compound. HRMS: calcd for $C_{14}H_{13}N_3O_4S+H^+$, 320.06995; found (ESI, $[M+H]^+$), 320.0707.

Example 124

4,4-Dimethyl-3-[4-(3-nitrophenyl)-1,3-thiazol-2-yl]-1,3-oxazolidin-2-one

This compound was prepared in the same manner as described in Example 95, replacing the [4-(trifluoromethyl)phenyl]-boronic acid with 3-nitrophenylboronic acid. The crude product was purified by reverse phase HPLC to give the title compound, mp>210° C.

Example 125

3-{4-[4-(Benzyloxy)phenyl]-1,3-thiazol-2-yl}-4,4-dimethyl-1,3-oxazolidin-2-one

This compound was prepared in the same manner as described in Example 95, replacing the [4-(trifluoromethyl)phenyl]-boronic acid with 4-benzyloxybenzeneboronic acid.

The crude product was purified by reverse phase HPLC to give the title compound. HRMS: calcd for $C_{21}H_{20}N_2O_3S+H^+$, 381.12674; found (ESI, $[M+H]^+$), 381.1288.

Example 126

3-[4-(4-Fluoro-3-methylphenyl)-1,3-thiazol-2-yl]-4,4-dimethyl-1,3-oxazolidin-2-one This compound was prepared in the same manner as described in Example 95, replacing the [4-(trifluoromethyl)phenyl]-boronic acid with 4-fluoro-3-methylbenzeneboronic acid. The crude product was purified by reverse phase HPLC to give the title compound. HRMS: calcd for $C_{15}H_{15}FN_2O_2S+H^+$, 307.09110; found (ESI, $[M+H]^+$), 307.0907.

Example 127

4,4-Dimethyl-3-[4-(4-phenoxyphenyl)-1,3-thiazol-2-yl]-1,3-oxazolidin-2-one

This compound was prepared in the same manner as described in Example 95, replacing the [4-(trifluoromethyl)phenyl]-boronic acid with 4-phenoxyphenylboronic acid. The crude product was purified by reverse phase HPLC to give the title compound. HRMS: calcd for $C_{20}H_{18}N_2O_3S+H^+$, 367.11109; found (ESI, $[M+H]^+$), 367.1112.

Example 128

3-(4-Biphenyl-4-yl-1,3-thiazol-2-yl)-4,4-dimethyl-1,3-oxazolidin-2-one

This compound was prepared in the same manner as described in Example 95, replacing the [4-(trifluoromethyl)phenyl]-boronic acid with biphenyl-4-boronic acid. The crude product was purified by reverse phase HPLC to give the title compound. HRMS: calcd for $C_{20}H_{18}N_2O_2S+H^+$, 351.11617; found (ESI, $[M+H]^+$), 351.1156.

Example 129

Methyl 4-[2-(4,4-dimethyl-2-oxo-1,3-oxazolidin-3-yl)-1,3-thiazol-4-yl]benzoate

This compound was prepared in the same manner as described in Example 95, replacing the [4-(trifluoromethyl)phenyl]-boronic acid with (4-methoxycarbonylphenyl)boronic acid. The crude product was purified by reverse phase HPLC to give the title compound, mp 176-179° C.

Example 130

Methyl 4-[5-chloro-2-(4,4-dimethyl-2-oxo-1,3-oxazolidin-3-yl)-1,3-thiazol-4-yl]benzoate Methyl 4-[2-(4,4-dimethyl-2-oxo-1,3-oxazolidin-3-yl)-1,3-thiazol-4-yl]benzoate, prepared in Example 129, and N-chlorosuccinimide are combined in dimethylformamide (5 mL). The mixture is stirred for 5 days and partitioned between water and ethyl acetate. The combined organic layers are dried over magnesium sulfate and concentrated onto silica gel. The residue is purified by silica gel Flash Chromatography to give the title compound. The melting point is anticipated to be 152-155° C.

Example 131

3-[4-(4-Chlorophenyl)-1,3-thiazol-2-yl]-1,3-oxazolidin-2-one

Step 1: Ethyl {[4-(4-chlorophenyl)-1,3-thiazol-2-yl]amino}(oxo)acetate

Ethyl oxalyl chloride (2.3 mL, 20.9 mmol) was added dropwise at room temperature to a solution of 4-(4-chlorophenyl)-thiazol-2-ylamine in dry pyridine (5 mL). After 2 h, the mixture was evaporated, acetone (20 mL) was added and the mixture was poured into water. The precipitate was collected and washed with hot ethanol to give ethyl {[4-(4-chlorophenyl)-1,3-thiazol-2-yl]amino}(oxo)acetate (5.10 g, 84%) as an off white solid. Anal. Calcd for $C_{13}H_{11}ClN_2O_3S$: C, 50.25; H, 3.57; N, 9.01. Found: C, 50.13; H, 3.64; N, 8.83. See, U.S. Pat. No. 4,847,274 for a general description regarding the preparation of phenyl-thiazole compounds.

Step 2: 2-{[4-(4-Chlorophenyl)-1,3-thiazol-2-yl]amino}ethanol

A solution of ethyl {[4-(4-chlorophenyl)-1,3-thiazol-2-yl]amino}(oxo)acetate (2.50 g, 8.04 mmol), prepared in the previous step, in dry tetrahydrofuran (25 mL) was added, under nitrogen, to a stirred suspension of lithium aluminum hydride (0.92 g, 24 mmol) in dry tetrahydrofuran (25 mL). After the addition was complete, the mixture was stirred for an additional 1 h. Ethyl acetate (4.8 mL) was added dropwise, followed by water (0.92 mL), 4N NaOH (0.92 mL) and water (2.8 mL). The mixture was then filtered and evaporated to afford 2-{[4-(4-chlorophenyl)-1,3-thiazol-2-yl]amino}ethanol (1.12 g, 55%) which was used without further purification. HRMS: calcd for $C_{11}H_{11}ClN_2OS$ $[M+H^+]$, 255.03534; found ($ESI^+$, $[M+H]^+$), 255.03505.

Step 3: 3-[4-(4-Chlorophenyl)-1,3-thiazol-2-yl]-1,3-oxazolidin-2-one 1,1'-Carbonyldiimidazole (0.16 g, 1 mmol) was added to a solution of 2-{[4-(4-chlorophenyl)-1,3-thiazol-2-yl]amino}ethanol (0.15 g, 0.58 mmol), prepared in the previous step, in dry tetrahydrofuran (5 mL) at room temperature under nitrogen. After 72 h, the mixture was evaporated and the residue purified by silica gel column chromatography (ethyl acetate:hexanes, 1:3 as eluant) to afford the title compound (9.8 mg, 5%) as a white solid, MS (ES) m/z 281 $[M+H]^+$. ANLC 96.4%@210 nm, 96.2%@230 nm; RT=8.0 min, the Xterra® MS C18m instrument, 3.5µ, 4.6×50 mm column, 0.8 mL/min, Grad: 5/95-95/5 (A) the PIC™ B6 reagent (5 mM Hex. Sulfonic Acid); (B) AcCN.

Example 132

4-[2-(2-Oxo-1,3-oxazolidin-3-yl)-1,3-thiazol-4-yl]benzonitrile

Step 1: 4-(2-Amino-thiazol-4-yl)-benzonitrile

Thiourea (0.76 g, 10 mmol) was added to 4-cyanophenacyl bromide (2.0 g, 8.9 mmol) in ethanol (20 mL), and the reaction heated under reflux. After 45 min, the mixture was cooled to room temperature, and poured into 2N NaOH (10 mL)/water (40 mL). The precipitate was collected and air-dried to give 4-(2-amino-thiazol-4-yl)benzonitrile (1.6 g, 90%), which was used without further characterization.

Step 2: 4-[2-(2-Oxo-1,3-oxazolidin-3-yl)-1,3-thiazol-4-yl]benzonitrile 4-(2-Amino-thiazol-4-yl)-benzonitrile (1.5 g, 7.4 mmol), prepared in the previous step, in dry tetrahydrofuran (10 mL) was added dropwise to a suspension of sodium hydride (0.6 g, ~15 mmol, 60% in oil) in dry tetrahydrofuran (10 mL) at room temperature. After 1 h, 2-chloroethyl chloroformate (0.83 mL, 8 mmol) was added dropwise and the mixture heated under reflux. After 16 h, the mixture was cooled, poured carefully into water, which was extracted with ethyl acetate. The organic layer was separated, dried (anhydrous $Na_2SO_4$), evaporated and the residue purified by silica gel column chromatography (ethyl acetate:hexane, 3:7) to afford the crude product. Recrystallization from ethanol gave the title compound (0.2 g, 10%), MS (ES) m/z 272 [M+H]$^+$. HPLC 99.5% @ 210-370 nm, 99.3% @ 240 nm; RT=8.3 min, the Xterra® RP18 column, 3.5μ, 4.6×150 mm column 1.2 mL/min, 85/15-5/95 (Phos Buff. pH=2.1/ACN+MeOH) for 10 min, hold 4 min.

Example 133

4-[2-(4,4-Dimethyl-2-oxo-1,3-oxazolidin-3-yl)-1,3-thiazol-4-yl]-1-methyl-1H-pyrrole-2-carbonitrile Step 1: 4-Acetyl-1-methyl-1H-pyrrole-2-carbonitrile To a solution of 1-methyl-3-acetylpyrrole (4.0 g, 32.5 mmol) in dry dichloromethane (40 mL), under nitrogen at −78° C., was added chlorosulfonyl isocyanate (2.8 mL, 32.5 mmol) dropwise. The reaction warmed to room temperature over 2 h, and was then treated with dimethylformamide (8 mL). After 30 min, the reaction was poured into water, treated with a 1 N sodium carbonate solution (10 mL) and extracted with methylene chloride (2×50 mL). The combined organic layers were washed with water, dried (anhydrous sodium sulfate) and evaporated. The residue was purified by silica gel column chromatography (ethyl acetate:hexanes, 3:1 to 1:1) to afford 4-acetyl-1-methyl-1H-pyrrole-2-carbonitrile (2.5 g, 16.87 mmol), which was used without further characterization.

Step 2: 4-(2-Bromo-acetyl)-1-methyl-1H-pyrrole-2-carbonitrile

To a stirred solution of 4-acetyl-1-methyl-1H-pyrrole-2-carbonitrile (2.50 g, 16.87 mmol), prepared in the previous step, in ethyl acetate (100 mL) was added copper (II) bromide (7.50 g, 33.74 mmol) and the mixture heated under reflux. After 6 h at reflux and a further 16 h at room temperature, the reaction mixture was passed through a pad of silica gel, which was further eluted with ethyl acetate (100 mL) and then the combined organics were evaporated. The crude product was triturated with hexanes to afford 4-(2-bromo-acetyl)-1-methyl-1H-pyrrole-2-carbonitrile (3.17 g, 83%), which was used without further characterization.

Step 3: 4-[2-(2-Hydroxy-1,1-dimethyl-ethylamino)-thiazol-4-yl]-1-methyl-1H-pyrrole-2-carbonitrile N-(2-Hydroxy-1,1-dimethylethyl)thiourea (0.75 g, 5 mmol), prepared in step 2 of Example 52, was added to 4-(2-bromo-acetyl)-1-methyl-1H-pyrrole-2-carbonitrile (1.15 g, 5 mmol), prepared in the previous step, in ethanol (20 mL) and the mixture was heated under reflux. After 2 h, the reaction was cooled to room temperature, the precipitate was collected, washed with ethanol, suspended in water and made basic with a 1 N sodium carbonate solution. The mixture was extracted with ethyl acetate, the organic layer was then washed with a 1 N sodium carbonate solution, water, dried (anhydrous $MgSO_4$) and evaporated to afford 4-[2-(2-hydroxy-1,1-dimethyl-ethylamino)-thiazol-4-yl]-1-methyl-1H-pyrrole-2-carbonitrile (0.92 g, 67%), which was used without further characterization.

Step 4: 4-[2-(4,4-Dimethyl-2-oxo-1,3-oxazolidin-3-yl)-1,3-thiazol-4-yl]-1-methyl-1H-pyrrole-2-carbonitrile To a mixture of triethylamine (0.42 mL, 3 mmol) and 4-[2-(2-hydroxy-1,1-dimethyl-ethylamino)-thiazol-4-yl]-1-methyl-1H-pyrrole-2-carbonitrile (0.75 g, 2.71 mmol), prepared in the previous step, in dry tetrahydrofuran (10 mL) was added triphosgene (0.83 g, 2.8 mmol) at room temperature. After 16 h, the mixture was poured into water/ethyl acetate. The organic layer was washed with water, dried (anhydrous sodium sulfate) and evaporated. The product was purified by silica gel column chromatography (ethyl acetate:hexanes, 1:4) to afford the title compound (0.29 g, 36%) as a white powder. HRMS: calcd for $C_{14}H_{14}N_4O_2S$ [M+H]$^+$, 303.09102; found (ESI, [M+H]$^+$), 303.0914; ANLC 99.6% at 210-370 nm, 9.0 min; 99.5% at 260 nm, 9.0 min, the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 134

5-[2-(4,4-Dimethyl-2-oxo-1,3-oxazolidin-3-yl)-1,3-thiazol-4-yl]-1-methyl-1H-pyrrole-3-carbonitrile Step 1: 5-Acetyl-1-methyl-1H-pyrrole-3-carbonitrile 1-(1-Methyl-1H-pyrrol-2-yl)-ethanone (4.00 g, 32.48 mmol) in dry methylene chloride (30 mL) was cooled to −78° C. under nitrogen. Chlorosulfonyl isocyanate (2.8 mL, 32.5 mmol) was added dropwise, and the mixture allowed to warm to room temperature over 1 h. The reaction was cooled down to −78° C. and dimethylformamide (8 mL) was added. The reaction was allowed to warm up to room temperature (2 h) and was then poured into a 1 N sodium carbonate solution, which was extracted with methylene chloride. The organic layers were washed with water, dried (anhydrous $MgSO_4$) and evaporated. The residue was then purified by silica gel column chromatography (ethyl acetate:hexanes 1:5 to 1:3) to afford 5-acetyl-1-methyl-1H-pyrrole-3-carbonitrile (1.63 g, 34%), which was used without further characterization.

Step 2: 5-(2-Bromo-acetyl)-1-methyl-1H-pyrrole-3-carbonitrile

A mixture of copper (II) bromide (4.89 g, 22 mmol) and 5-acetyl-1-methyl-1H-pyrrole-3-carbonitrile (1.63 g, 11 mmol), prepared in the previous step, in ethyl acetate (65 mL) was heated under reflux for 4 h. After cooling to room temperature, the mixture was filtered through a pad of silica gel, which was further eluted with ethyl acetate. The combined organic fractions were evaporated to afford approximately a 2:1 mixture of 5-(2-bromo-acetyl)-1-methyl-1H-pyrrole-3-carbonitrile and 5-acetyl-1-methyl-1H-pyrrole-3-carbonitrile, which was used without further purification.

Step 3: 5-{2-[(2-Hydroxy-1,1-dimethylethyl)amino]-1,3-thiazol-4-yl}-1-methyl-1H-pyrrole-3-carbonitrile The above prepared 2:1 mixture of 5-(2-bromo-acetyl)-1-methyl-1H-pyrrole-3-carbonitrile and 5-acetyl-1-methyl- 1H-pyrrole-3-carbonitrile in ethanol (50 mL) was treated with N-(2-Hydroxy-1,1-dimethylethyl)thiourea, prepared in step 2 of Example 52, and heated under reflux. The mixture was filtered while still hot, and the precipitate washed with ethanol, and then partitioned between 1 N sodium carbonate and ethyl acetate. The organic layer was washed with water, dried (anhydrous MgSO$_4$) and evaporated to afford 5-{2-[(2-hydroxy-1,1-dimethylethyl)amino]-1,3-thiazol-4-yl}-1-methyl-1H-pyrrole-3-carbonitrile (1.10 g, 3.98 mmol), as a yellow oil. ANLC 100% at 210-370 nm, 7.8 min; 100% at 248 nm, 7.8 min, the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min. HRMS: calcd for $C_{13}H_{16}N_4OS$ [M+H]$^+$, 277.11176; found (ESI, [M+H]$^+$), 277.1126.

Step 4: 5-[2-(4,4-Dimethyl-2-oxo-1,3-oxazolidin-3-yl)-1,3-thiazol-4-yl]-1-methyl-1H-pyrrole-3-carbonitrile To a solution of 5-{2-[(2-hydroxy-1,1-dimethylethyl)amino]-1,3-thiazol-4-yl}-1-methyl-1H-pyrrole-3-carbonitrile (1.10 g, 3.98 mmol), prepared in the previous step, in dry tetrahydrofuran (10 mL) under nitrogen was added triethylamine (0.56 mL, 4 mmol), followed by triphosgene (1.18 g, 4 mmol). After 2 h, the mixture was partitioned between water and ethyl acetate. The organic layers were washed with water, dried (anhydrous sodium sulfate) and evaporated. The residue was then purified by silica gel column chromatography (ethyl acetate:hexanes, gradient elution) to afford the title compound (0.80 g, 66%) as an off white powder. HRMS: calcd for $C_{14}H_{14}N_4O_2S$ [M+H]$^+$, 303.09102; found (ESI, [M+H]$^+$), 303.093, ANLC 99.4% at 210-370 nm, 8.6 min; 99.7% at 246 nm, 8.6 min, the Xterra® RP18 column, 3.5%, 150×4.6 mm column, 1.2 mL/min, 85/15-5/95 (Ammon. Form. Buff. pH=3.5/ACN+MeOH) for 10 min, hold 4 min.

Example 135

{(2Z)-3-[4-(4-cyanophenyl)-1,3-thiazol-2-yl]-4,4-dimethyl-1,3-oxazolidin-2-ylidene}cyanamide 4-[2-(2-Imino-4,4-dimethyl-1,3-oxazolidin-3-yl)-1,3-thiazol-4-yl]benzonitrile (0.250 g, 0.83 mmol), prepared in Example 63, was dissolved in tetrahydrofuran (2 mL) followed by triethylamine (0.139 mL, 1 mmol) and cyanogen bromide (0.21 g, 2 mmol). The mixture was stirred overnight, filtered and the tetrahydrofuran was removed in vacuo. Purification by normal phase HPLC on a phenomenex cyano column eluting with hexane/1,2-dimethoxyethane (9:1 to 1:9) gave the title compound (0.020 g, 7%). HRMS: calcd for $C_{16}H_{13}N_5OS$+H$^+$, 324.09136; found (ESI, [M+H]$^+$), 324.0919; HPLC purity 100% at 210-370 nm, 9.3 min; 100% at 246 nm, 9.3 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 136

N-{(2Z)-3-[4-(4-Cyanophenyl)-1,3-thiazol-2-yl]-4,4-dimethyl-1,3-oxazolidin-2-ylidene}methanesulfonamide 4-[2-(2-Imino-4,4-dimethyl-1,3-oxazolidin-3-yl)-1,3-thiazol-4-yl]benzonitrile (0.250 g, 0.83 mmol), prepared in Example 63, was dissolved in tetrahydrofuran (2 mL), followed by triethylamine (0.139 mL, 1 mmol) and methanesulfonyl chloride (0.154 mL, 2 mmol). The mixture was stirred overnight, filtered and the tetrahydrofuran was removed in vacuo. Purification by normal phase HPLC on a phenomenex cyano column and eluting with hexane/1,2-dimethoxyethane (9:1 to 1:9) gave the title compound (0.020 g, 6%). HRMS: calcd for $C_{16}H_{16}N_4O_3S_2$+H$^+$, 377.07366; found (ESI, [M+H]$^+$), 377.0722. HPLC purity 97.0% at 210-370 nm, 8.5 min; 97.1% at 244 nm, 8.5 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 137

N-{(2Z)-3-[4-(4-Cyanophenyl)-1,3-thiazol-2-yl]-4,4-dimethyl-1,3-oxazolidin-2-ylidene}acetamide 4-[2-(2-Imino-4,4-dimethyl-1,3-oxazolidin-3-yl)-1,3-thiazol-4-yl]benzonitrile (0.075 g, 0.25 mmol), prepared in Example 63, was dissolved in tetrahydrofuran (2 mL) followed by triethylamine (0.069 mL, 0.5 mmol) and acetylchloride (0.039 g, 0.5 mmol). The mixture was stirred 4 h, poured into water, extracted with ethyl acetate, and dried over anhydrous MgSO$_4$. The solvent was evaporated and residue triturated with hexane/ethyl acetate (95/5), collected and dried to give the title compound (0.055 g, 64%). HRMS: calcd for $C_{17}H_{16}N_4O_2S$+H$^+$, 341.10667; found (ESI, [M+H]$^+$), 341.1075; HPLC purity 96.5% at 210-370 nm, 9.4 min; 96.0% at 250 nm, 9.4 min; the Xterra® RP18 column, 3.5μ, 150×4.6 mm column, 1.2 mL/min, 85/15-5/95 (Ammon. Form. Buff. pH=3.5/ACN+MeOH) for 10 min, hold 4 min.

Example 138

2-[4-(4-bromophenyl)-1,3-thiazol-2-yl]-2-azabicyclo[2.2.2]octan-3-one cis-4-Amino-1-cyclohexanecarboxylic acid (1.43 g, 10 mmol) was suspended in THF (30 mL) and triethylamine (1.31 mL, 9.5 mmol) was added, followed by benzoylisothiocyanate (1.36 mL, 10 mmol). The mixture was heated to reflux for 2 h, cooled, and stirred for 48 h. Lithium hydroxide (1N aqueous solution, 20 mL, 20 mmol) was added, the mixture was heated to reflux for 1 h, and the mixture was then cooled to 25° C. 2-Bromo-1-(4-bromo-phenyl)-ethanone (2.78 g, 10 mmol) was added, the mixture was heated to reflux for 1 h, and the mixture was then cooled to 25° C. The mixture was diluted with water, acidified with 2N HCl, and extracted with ethyl acetate. The organics were combined and washed with brine, dried over MgSO$_4$, and concentrated. Flashing with 25% acetone in hexane with 0.5% acetic acid gave the intermediate 4-[4-(4-bromophenyl)-thiazol-2-ylamino]-cyclohexanecarboxylic acid (0.38 g).

A portion of 4-[4-(4-Bromo-phenyl)-thiazol-2-ylamino]-cyclohexanecarboxylic acid (50 mg, 0.13 mmol) was dissolved in dioxane (10 mL). Carbonyl diimidazole (26 mg, 0.16 mmol) was added and the mixture was heated to 100° C. for 16 h. The mixture was concentrated and chromatographed with 10% acetone in hexane to give 32 mg of 2-[4-(4-bromophenyl)-1,3-thiazol-2-yl]-2-azabicyclo[2.2.2]octan-3-one.

HPLC purity 100% at 210-370 nm, 11.3 min; 100% at 240 nm, 11.3 min; the Xterra® RP18 instrument, 3.5μ, 150×4.6 mm column, 1.2 mL/min, 85/15-5/95 (Ammon. Form. Buff. pH=3.5/ACN+MeOH) for 10 min, hold 4 min. HRMS: calcd for $C_{16}H_{15}BrN_2OS$+H$^+$, 363.01612; found (ESI, [M+H]$^+$), 363.0159.

Example 139

4-[2-(3-oxo-2-azabicyclo[2.2.2]oct-2-yl)-1,3-thiazol-4-yl]benzonitrile cis-4-Amino-1-cyclohexanecarboxylic acid (1.5 g, 10.5 mmol) was suspended in THF (40 mL), lithium hydroxide (1N aqueous solution, 10.5 mL, 10.5 mmol) was added, followed by benzoylisothiocyanate (1.42 mL, 10.5 mmol). The mixture was stirred for 30 min, lithium hydroxide (1N aqueous solution, 10.5 mL, 10.5 mmol) was added, and the mixture was heated to reflux for 1 h. Additional lithium hydroxide (1N aqueous solution, 0.3 mL, 0.3 mmol) was added, heating was continued for 30 min, and then the mixture was cooled to 25° C. 2-Bromo-1-(4-cyanophenyl)-ethanone (2.35 g, 10.5 mmol) was added, the mixture was heated to reflux for 1 h, and then concentrated. The crude product was chromatographed with 25% acetone in hexane with 0.5% acetic acid. Further chromatography with 20% acetone:20% ethyl acetate:60% hexane provided the intermediate 4-[4-(4-cyano-phenyl)-thiazol-2-ylamino]-cyclohexanecarboxylic acid (0.196 g, 0.609) that was dissolved in dioxane (30 mL). Carbonyl diimidazole (118 mg, 0.73 mmol) was added and the mixture was heated to 100° C. for 16 h. The mixture was concentrated and flashed with 10% acetone in hexane to give 105 mg of 4-[2-(3-oxo-2-azabicyclo[2.2.2]oct-2-yl)-1,3-thiazol-4-yl]benzonitrile.

HPLC purity 100% at 210-370 nm, 10.0 min; 100% at 244 nm, 10.0 min; the Xterra® RP18 instrument, 3.5%, 150×4.6 mm column, 1.2 mL/min, 85/15-5/95 (Ammon. Form. Buff. pH=3.5/ACN+MeOH) for 10 min, hold 4 min. HRMS: calcd for $C_{17}H_{15}N_3OS+H^+$, 310.10086; found (ESI, $[M+H]^+$), 310.1000.

Example 140

(1) Effects of Progestins and Antiprogestins on Alkaline Phosphatase Activity in T47D Cells PURPOSE: To identify progestins or antiprogestins by determining a compound's effect on alkaline phosphatase activity in T47D cells.

A. Reagents:
  Culture Medium:
    DMEM:F12 (1:1) (GIBCO, BRL) supplemented with 5% (v/v) charcoal stripped fetal bovine serum (not heat-inactivated), 100 U/mL penicillin, 100 µg/mL streptomycin, and 2 mM the GlutaMax™ reagent (GIBCO, BRL).
  Alkaline Phosphatase Assay Buffer:
    I. 0.1M Tris-HCl, pH 9.8, containing 0.2% the Triton® X-100 reagent
    II. 0.1M Tris-HCl, pH 9.8, containing 4 mM p-nitrophenyl phosphate (Sigma).

B. Cell Culture and Treatment:
  Frozen T47D cells were thawed in a 37° C. water bath and diluted to 280,000 cells/mL in culture medium. To each well in a 96-well plate (Falcon, Becton Dickinson Labware), 180 µL of diluted cell suspension was added.

Twenty µL of reference or test compounds diluted in the culture medium was then added to each well. When testing for progestin antagonist activity, reference antiprogestins or test compounds were added in the presence of 1 nM progesterone. The cells were incubated at 37° C. in a 5% $CO_2$/humidified atmosphere for 24 h.

NOTE: For high throughput screening, one concentration of each compound was tested at 0.3 µg/mL. Based on an average molecular weight of 300 g/mol for the compounds in the library, the concentration was approximately 1 µM. Subsequently, active compounds were tested in dose response assays to determine $EC_{50}$ and $IC_{50}$.

C. Alkaline Phosphatase Enzyme Assay:
  At the end of treatment, the medium was removed from the plate. Fifty µL of assay buffer I was added to each well. The plates were shaken in a titer plate shaker for 15 min. Then 150 µL of assay buffer II was added to each well. Optical density measurements were taken at 5 min intervals for 30 min at a test wavelength of 405 nM.

D. Analysis of Results:
  For reference and test compounds, a dose response curve was generated for dose (X-axis) vs. the rate of enzyme reaction (slope) (Y-axis). Square root-transformed data was used for analysis of variance and nonlinear dose response curve fitting for both agonist and antagonist modes. Huber weighting was used to down-weight the effects of outliers. $EC_{50}$ or $IC_{50}$ values were calculated from the retransformed values. JMP software (SAS Institute, Inc.) was used for both one-way analysis of variance and non-linear dose response analysis in both single dose and dose response studies.

E. Reference Compounds:
  Progesterone and trimegestone were reference progestins and RU486 was the reference antiprogestin. All reference compounds were run in full dose response curves and the $EC_{50}$ and $IC_{50}$ values were calculated.

(2) Progesterone Receptor Whole Cell Competition Binding Assay Using T47D Cells PURPOSE: To evaluate the progesterone receptor (PR) binding activity of progestins or antiprogestins in live, intact (whole) cells using the human breast carcinoma T47D cell line and $^3$H-progesterone as the labeled ligand.

A. Reagents:
  Culture Medium:
    5% RC: phenol red free DMEM:F12 (1:1) (GIBCO, BRL) supplemented with 5% (v/v) charcoal stripped fetal bovine serum (not heat-inactivated), 100 U/mL penicillin, 100 µg/mL streptomycin, and 2 mM the GlutaMax™ reagent (GIBCO, BRL).
    10% RC: Same as above supplemented with 10% (v/v) FBS.
  $^3$H-Progesterone: Perkin Elmer Life Science, cat# NET-381 (typically around 102 Ci/mmol)
  Liquid Scintillation Cocktail:
    the Ready-Safe™ cocktail, cat# 141349 (Beckman Coulter)
  Tissue Culture Plates:
    96 well, clear bottom, white, plates: VWR Part #: 29443-150 or Perkin Elmer Part #: 3983498

B: T47D Cell Culture:
  T47D cells were maintained in 10% RC media at 37° C. in a 5% $CO_2$/humidified atmosphere and were split twice weekly for proper response. Cells were plated in 10% RC the day before binding assay at 50,000 cells per well in the white, clear bottom plates purchased through VWR or Perkin Elmer.

C: Binding Assay:
  Cells plated the day prior to the assay in white clear bottom plates were used. A master compound plate was set up containing control and test compounds at 20× final desired concentration for the competition binding. A typical dose range of 20× concentrations were (in nM): 200,000; 20,000; 6000; 2000; 600; 200; 20; and 2. Final concentrations were (in nM);

10,000; 1000; 300; 100; 30; 10; 1; 0.1. Control compounds were typically run 10-fold lower than this and include a 0, or vehicle, control well. A stock of 60 nM $^3$H-progesterone (20×) were also prepared at a volume needed of 10 μL per well.

Media on cells were replaced with 180 μL of 5% RC. Ten microliters (10 μL) of 60 nM $^3$H-progesterone (for final concentration of 3 nM) was added immediately, followed by 10 μL of 20× test or control compounds. Compounds were incubated for 3 h at 37° C. (A time course study found no difference between 2 and 4 h incubation.)

Following incubation, media was carefully removed and cells were washed 3× with 200 μL 5% RC each wash. Fifty microliters of liquid scintillation cocktail was added and the plates were shaken vigorously for a minimum of 15 min. Plates were read on the Wallac Microbeta® 1450 plate reader.

D. Analysis of Results:

Square root-transformed data were used for analysis of variance and calculation of IC$_{50}$. SAS software (SAS Institute, Inc.) was used for all the statistical analysis.

E. Reference Compounds:

Progesterone was used as a reference progestin and RU486 as a reference antiprogestin.

TABLE 1

| Example | T47D Alkaline Phosphatase Activity IC$_{50}$ (nM) or % inhibition | PR T47D Whole Cell Binding Ki (nM) |
|---|---|---|
| 1 | 22.1 | 87.6 |
| 2 | 14.6 | 43.4 |
| 3 | 24.6 | 55.3 |
| 4 | 15.8 | 62.8 |
| 5 | 6.4 | 38.2 |
| 6 | 3.1 | 4.9 |
| 7 | 23 | 75.3 |
| 8 | 14.6 | 52.6 |
| 9 | 32.9 | 62.1 |
| 10 | 12.8 | 23.3 |
| 11 | 119.7 | |
| 12 | 23.3 | |
| 13 | 123.8 | |
| 14 | 293.5 | |
| 15 | 144.2 | |
| 16 | 141.8 | |
| 17 | 84% at 3000 nM | |
| 18 | 30 | |
| 19 | 0.45 | |
| 20 | 70.2 | |
| 21 | 22.5 | |
| 22 | 64.3 | |
| 23 | 28.1 | 41.2 |
| 24 | 292.3 | |
| 25 | 21.6 | |
| 26 | 49.4 | 91.8 |
| 27 | 17.1 | |
| 28 | 157.5 | |
| 29 | 88.8 | |
| 30 | 100% at 3000 nM | |
| 31 | 68.8 | |
| 32 | 407.3 | |
| 33 | 237.6 | |
| 34 | 95.3 | 529 |
| 35 | 204.3 | 713 |
| 36 | 345.9 | 968 |
| 37 | 359 | 566 |
| 38 | 75.6 | 108 |
| 39 | 1367 | |
| 40 | 9.9 | 42 |
| 41 | 48.3 | 284 |
| 42 | 117.3 | 700 |
| 43 | 21.9 | |
| 44 | 190.7 | |
| 45 | 166.5 | |

TABLE 1-continued

| Example | T47D Alkaline Phosphatase Activity IC$_{50}$ (nM) or % inhibition | PR T47D Whole Cell Binding Ki (nM) |
|---|---|---|
| 46 | 193.8 | |
| 47 | 45.4 | |
| 48 | 23.3 | 128 |
| 49 | 39 | 68 |
| 50 | 17.7 | 36.6 |
| 51 | 16.1 | 42.6 |
| 52 | 95% at 3000 nM | |
| 53 | 40% at 3 nM | |
| 54 | 50% at 3000 nM | |
| 55 | 41.9 | |
| 56 | 436.9 | |
| 57 | 100.6 | |
| 58 | 4 | 16.1 |
| 59 | 99 | |
| 60 | 43.5 | |
| 61 | 37.8 | |
| 62 | 1.8 | |
| 63 | 53.4 | |
| 64 | 290.8 | 234 |
| 65 | 43.2 | 60.3 |
| 66 | 481.5 | 212 |
| 67 | 95.5 | |
| 68 | 29.1 | |
| 69 | 63.8 | |
| 70 | 90% at 3000 nM | |
| 71 | 565.4 | |
| 72 | 5.4 | 20 |
| 73 | 21.4 | 31.5 |
| 74 | 19.8 | 45.1 |
| 75 | 1068 | 2084 |
| 76 | 732.8 | |
| 77 | 372.3 | 584 |
| 78 | 24.8 | 45.6 |
| 79 | 31.6 | 170 |
| 80 | 8.6 | 34.5 |
| 81 | 2.3 | ~2000 |
| 82 | 6.4 | |
| 83 | 35.4 | |
| 84 | 77.9 | |
| 85 | 729.3 | |
| 86 | 5 | |
| 87 | 60% at 3 nM | |
| 88 | 50% at 3 nM | |
| 89 | 31.6 | |
| 90 | 43.5 | |
| 91 | 63% at 3000 nM | |
| 92 | 76% at 3000 nM | |
| 93 | 134.7 | |
| 94 | 146.2 | |
| 95 | 108.2 | |
| 96 | 328.2 | |
| 97 | 285.2 | |
| 98 | 191 | |
| 99 | 64.6 | |
| 100 | 853.8 | |
| 101 | 535.7 | |
| 102 | 27% at 3000 nM | |
| 103 | 262 | |
| 104 | 94% at 3000 nM | |
| 105 | 110.2 | |
| 106 | 497.5 | |
| 107 | 83.7 | |
| 108 | 822.9 | |
| 109 | 28.8 | |
| 110 | 268.9 | |
| 111 | 27.9 | |
| 112 | 480 | |
| 113 | 100.4 | |
| 114 | 53% at 30 nM | |
| 115 | 72.2 | |
| 116 | 460.7 | |
| 117 | 50.4 | |
| 118 | 60% at 30 nM | |
| 119 | 48 | |

TABLE 1-continued

| Example | T47D Alkaline Phosphatase Activity $IC_{50}$ (nM) or % inhibition | PR T47D Whole Cell Binding Ki (nM) |
|---|---|---|
| 120 | 247.1 | |
| 121 | 109.6 | |
| 122 | 556.7 | |
| 123 | 1417.8 | |
| 124 | 59.7 | |
| 125 | 80% at 3000 nM | |
| 126 | 33.4 | |
| 127 | 87% at 3000 nM | |
| 128 | 47% at 3000 nM | |
| 129 | 20.3 | |
| 130 | 181.3 | |
| 131 | 41.1 | |
| 132 | 37.6 | |
| 133 | 69.6 | |
| 134 | 284.1 | |
| 135 | 64.4 | |
| 136 | 100% at 3000 nM | |
| 137 | 10.8 | |
| 138 | 44.4 | |
| 139 | 4.8 | |

All publications cited in this specification are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of the structure:

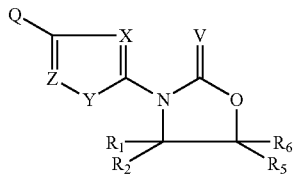

wherein:
$R_1$ and $R_2$ are independently, H, $C_1$ to $C_{10}$ alkyl, —$(CH_2)_n$-aryl, —$(CH_2)_p$—O—$(CH_2)_n$-aryl, —$(CH_2)_nC(H)_{3-p}(R_7)_p$, or —$(CH_2)_nCOOR_8$;
$R_5$ and $R_6$ are H; or
$R_1$, $R_2$ or $R_5$, $R_6$ are taken together to form a carbon-based 3 to 6 membered saturated ring; or
$R_1$ or $R_2$ forms a carbon-based 5 to 7 membered saturated ring with $R_5$ or $R_6$; or
$R_1$ or $R_2$ forms a carbon-based 6-membered aromatic ring with $R_5$ or $R_6$;
$R_7$ is halogen;
$R_8$ is $C_1$ to $C_6$ alkyl;
$R_9$ is H, $C_1$ to $C_6$ alkyl, or $C_1$ to $C_3$ perfluoroalkyl;
V is O or S;
X and Z are, independently, N or $CR_{14}$;
$R_{14}$ is H, $C_1$ to $C_6$ alkyl, —$(CH_2)_n$-aryl, —$(CH_2)_n$—O—$(CH_2)_n$-alkyl, —$(CH_2)_n$—O—$(CH_2)_n$-aryl, halogen, hydroxy, $C_1$ to $C_3$ perfluoroalkyl, $C_1$ to $C_3$ perfluoroalkoxy, or —$(CH_2)_n$—CN;
Y is S;
Q is aryl or heteroaryl, each substituted by one or more of $R_{15}$ and $R_{15}$ is —$(CH_2)_nCN$, halogen, $NO_2$, —$C(NH_2)$=N—OH, $C_1$ to $C_3$ perfluoroalkyl, $C_1$ to $C_3$ perfluoroalkoxy, —O—$(C_1$ to $C_4$ alkyl), —O—$(C_1$ to $C_4$ substituted alkyl), —$SO_2$—$(C_1$ to $C_4$ alkyl), —$SO_2$—$(C_1$ to $C_4$ substituted alkyl), —CO—$(C_1$ to $C_4$ alkyl), —CO—$(C_1$ to $C_4$ substituted alkyl), $C_1$ to $C_4$ alkyl, $C_1$ to $C_4$ substituted alkyl, —O—$(CH_2)_n$-aryl, —COO—$(C_1$ to $C_4$ alkyl), —COO—$(C_1$ to $C_4$ substituted alkyl), —CONH—$(C_1$ to $C_3$ alkyl), —CON—$(C_1$ to $C_3$ alkyl)$_2$, aryl, substituted aryl, heteroaryl or substituted heteroaryl;

n is 0 to 3;

p is 1 to 3;

or a pharmaceutically acceptable salt or tautomer thereof.

2. The compound according to claim 1, wherein X is N, Y is S, and Z is $CR_{14}$.

3. The compound according to claim 1, wherein X and Z are N and Y is S.

4. The compound according to claim 1, wherein V is O.

5. The compound according to claim 1, wherein $R_1$ and $R_2$ are $C_1$ to $C_{10}$ alkyl and $R_5$ and $R_6$ are H.

6. The compound according to claim 1, wherein Q is a substituted phenyl.

7. The compound according to claim 6, wherein said phenyl is substituted by one or more of $R_{15}$ and $R_{15}$ is —$(CH_2)_n$CN, halogen, $NO_2$, —$C(NH_2)$=N—OH, $C_1$ to $C_3$ perfluoroalkyl, $C_1$ to $C_3$ perfluoroalkoxy, —O—$(C_1$ to $C_4$ alkyl), —O—$(C_1$ to $C_4$ substituted alkyl), —$SO_2$—$(C_1$ to $C_4$ alkyl), —$SO_2$—$(C_1$ to $C_4$ substituted alkyl), —CO—$(C_1$ to $C_4$ alkyl), —CO—$(C_1$ to $C_4$ substituted alkyl), $C_1$ to $C_4$ alkyl, $C_1$ to $C_4$ substituted alkyl, —O—$(CH_2)_n$— aryl, —COO—$(C_1$ to $C_4$ alkyl), —COO—$(C_1$ to $C_4$ substituted alkyl), —CONH—$(C_1$ to $C_3$ alkyl), —CON—$(C_1$ to $C_3$ alkyl)$_2$, aryl, substituted aryl, heteroaryl, or substituted heteroaryl.

8. The compound according to claim 7, wherein $R_{15}$ is CN or Br.

9. The compound according to claim 1 of the structure:

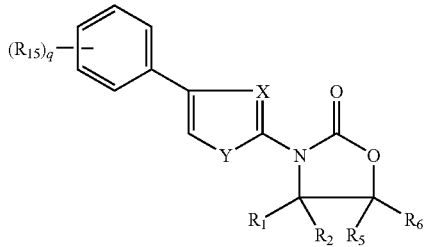

wherein:
$R_{15}$ is —$(CH_2)_n$CN, halogen, $NO_2$, —$C(NH_2)$=N—OH, $C_1$ to $C_3$ perfluoroalkyl, $C_1$ to $C_3$ perfluoroalkoxy, —O—$(C_1$ to $C_4$ alkyl), —O—$(C_1$ to $C_4$ substituted alkyl), —$SO_2$—$(C_1$ to $C_4$ alkyl), —$SO_2$—$(C_1$ to $C_4$ substituted alkyl), —CO—$(C_1$ to $C_4$ alkyl), —CO—$(C_1$ to $C_4$ substituted alkyl), $C_1$ to $C_4$ alkyl, $C_1$ to $C_4$ substituted alkyl, —O—$(CH_2)_n$-aryl, —COO—$(C_1$ to $C_4$ alkyl), —COO—$(C_1$ to $C_4$ substituted alkyl), —CONH—$(C_1$ to $C_3$ alkyl), —CON—$(C_1$ to $C_3$ alkyl)$_2$, aryl, substituted aryl, heteroaryl, or substituted heteroaryl; and q is 1 to 4.

10. The compound according to claim 1 of the structure:

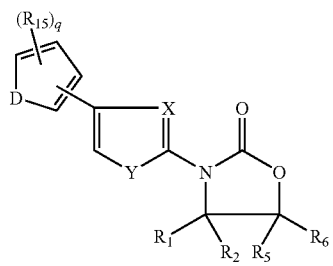

wherein:

D is S, NR$_{16}$, or O;

R$_{15}$ is —(CH$_2$)$_n$CN, halogen, NO$_2$, —C(NH$_2$)=N—OH, C$_1$ to C$_3$ perfluoroalkyl, C$_1$ to C$_3$ perfluoroalkoxy, —O—(C$_1$ to C$_4$ alkyl), —O—(C$_1$ to C$_4$ substituted alkyl), —SO$_2$—(C$_1$ to C$_4$ alkyl), —SO$_2$—(C$_1$ to C$_4$ substituted alkyl), —SO—(C$_1$ to C$_4$ alkyl), —CO—(C$_1$ to C$_4$ substituted alkyl), C$_1$ to C$_4$ alkyl, C$_1$ to C$_4$ substituted alkyl, —O—(CH$_2$)-aryl, —COO—(C$_1$ to C$_4$ alkyl), —COO—(C$_1$ to C$_4$ substituted alkyl), —CONH—(C$_1$ to C$_3$ alkyl), —CON—(C$_1$ to C$_3$ alkyl)$_2$, aryl, substituted aryl, heteroaryl, or substituted heteroaryl;

R$_{16}$ is H, C$_1$ to C$_{10}$ alkyl, C$_1$ to C$_{10}$ substituted alkyl, or —COO—(C$_1$ to C$_{10}$ alkyl); and q is 1 to 3.

11. The compound according to claim 9, wherein R$_1$, R$_2$, R$_5$, and R$_6$ are independently H or C$_1$ to C$_{10}$ alkyl.

12. The compound according to claim 1 which is selected from the group consisting of 3-[4-(4-Chlorophenyl)-1,3-thiazol-2-yl]-1,3-oxazolidin-2-one, 3-[4-(4-Bromophenyl)-1,3-thiazol-2-yl]-1,3-oxazolidin-2-one, 4-[2-(2-Oxo-1,3-oxazolidin-3-yl)-1,3-thiazol-4-yl]benzonitrile, 3-[4-(4-Bromophenyl)-1,3-thiazol-2-yl]-4-methyl-1,3-oxazolidin-2-one, 4-[2-(4-Methyl-2-oxo-1,3-oxazolidin-3-yl)-1,3-thiazol-4-yl]benzonitrile, (4S)-3-[4-(4-Bromophenyl)-1,3-thiazol-2-yl]-4-methyl-1,3-oxazolidin-2-one, (4R)-3-[4-(4-Bromophenyl)-1,3-thiazol-2-yl]-4-methyl-1,3-oxazolidin-2-one, 4-{2-[(4S)-4-Methyl-2-oxo-1,3-oxazolidin-3-yl]-1,3-thiazol-4-yl}benzonitrile, 4-{2-[(4R)-4-Methyl-2-oxo-1,3-oxazolidin-3-yl]-1,3-thiazol-4-yl}benzonitrile, (4R)-3-[4-(3-bromophenyl)-1,3-thiazol-2-yl]-4-methyl-1,3-oxazolidin-2-one, 3-{2-[(4R)-4-Methyl-2-oxo-1,3-oxazolidin-3-yl]-1,3-thiazol-4-yl}benzonitrile, 3-[4-(4-Bromophenyl)-1,3-thiazol-2-yl]-4-ethyl-1,3-oxazolidin-2-one, (4R)-3-[4-(4-Bromophenyl)-1,3-thiazol-2-yl]-4-ethyl-1,3-oxazolidin-2-one, (4S)-3-[4-(4-Bromophenyl)-1,3-thiazol-2-yl]-4-ethyl-1,3-oxazolidin-2-one, 4-{2-[(4R)-4-Ethyl-2-oxo-1,3-oxazolidin-3-yl]-1,3-thiazol-4-yl}benzonitrile, 4-{2-[(4S)-4-Ethyl-2-oxo-1,3-oxazolidin-3-yl]-1,3-thiazol-4-yl}benzonitrile, 3-[4-(4-Bromophenyl)-1,3-thiazol-2-yl]-4-propyl-1,3-oxazolidin-2-one, 4-[2-(2-Oxo-4-propyl-1,3-oxazolidin-3-yl)-1,3-thiazol-4-yl]benzonitrile, (4R)-3-[4-(4-Bromophenyl)-1,3-thiazol-2-yl]-4-propyl-1,3-oxazolidin-2-one, (4S)-3-[4-(4-Bromophenyl)-1,3-thiazol-2-yl]-4-propyl-1,3-oxazolidin-2-one, 4-{2-[(4S)-2-oxo-4-propyl-1,3-oxazolidin-3-yl]-1,3-thiazol-4-yl}benzonitrile, 4-{2-[(4R)-2-oxo-4-propyl-1,3-oxazolidin-3-yl]-1,3-thiazol-4-yl}benzonitrile, 3-[4-(4-Bromophenyl)-1,3-thiazol-2-yl]-4-isopropyl-1,3-oxazolidin-2-one, 4-[2-(4-isopropyl-2-oxo-1,3-oxazolidin-3-yl)-1,3-thiazol-4-yl]benzonitrile, 3-[4-(4-Bromophenyl)-1,3-thiazol-2-yl]-4-butyl-1,3-oxazolidin-2-one, 4-[2-(4-Butyl-2-oxo-1,3-oxazolidin-3-yl)-1,3-thiazol-4-yl]benzonitrile, (4S)-3-[4-(4-Bromophenyl)-1,3-thiazol-2-yl]-4-isobutyl-1,3-oxazolidin-2-one, (4R)-3-[4-(4-Bromophenyl)-1,3-thiazol-2-yl]-4-phenyl-1,3-oxazolidin-2-one, 4-{2-[(4R)-2-Oxo-4-phenyl-1,3-oxazolidin-3-yl]-1,3-thiazol-4-yl}benzonitrile, 4-{2-[(4S)-2-Oxo-4-phenyl-1,3-oxazolidin-3-yl]-1,3-thiazol-4-yl}benzonitrile, (4R)-4-Benzyl-3-[4-(4-bromophenyl)-1,3-thiazol-2-yl]-1,3-oxazolidin-2-one, 4-{2-[(4R)-4-Benzyl-2-oxo-1,3-oxazolidin-3-yl]-1,3-thiazol-4-yl}benzonitrile, (4S)-4-[(benzyloxy)methyl]-3-[4-(4-bromophenyl)-1,3-thiazol-2-yl]-1,3-oxazolidin-2-one, (4R)-3-[4-(4-Bromophenyl)-1,3-thiazol-2-yl]-4-(hydroxymethyl)-1,3-oxazolidin-2-one, (4S)-3-[4-(4-Bromophenyl)-1,3-thiazol-2-yl]-4-(fluoromethyl)-1,3-oxazolidin-2-one, 4-{2-[(4S)-4-(Fluoromethyl)-2-oxo-1,3-oxazolidin-3-yl]-1,3-thiazol-4-yl}benzonitrile, (4S)-3-[4-(4-Bromophenyl)-1,3-thiazol-2-yl]-4-(chloromethyl)-1,3-oxazolidin-2-one, 3-[4-(4-Bromophenyl)-1,3-thiazol-2-yl]-4-(trifluoromethyl)-1,3-oxazolidin-2-one, 4-{2-[(4R)-2-oxo-4-(trifluoromethyl)-1,3-oxazolidin-3-yl]-1,3-thiazol-4-yl}benzonitrile, 4-{2-[(4S)-2-Oxo-4-(trifluoromethyl)-1,3-oxazolidin-3-yl]-1,3-thiazol-4-yl}benzonitrile, 3-[4-(4-Bromophenyl)-1,3-thiazol-2-yl]-4-(2,2,2-trifluoroethyl)-1,3-oxazolidin-2-one, 4-{2-[(4S)-2-Oxo-4-(2,2,2-trifluoroethyl)-1,3-oxazolidin-3-yl]-1,3-thiazol-4-yl}benzonitrile, 4-{2-[(4R)-2-Oxo-4-(2,2,2-trifluoroethyl)-1,3-oxazolidin-3-yl]-1,3-thiazol-4-yl}benzonitrile, and Methyl (4S)-3-[4-(4-bromophenyl)-1,3-thiazol-2-yl]-2-oxo-1,3-oxazolidine-4-carboxylate.

13. The compound according to claim 1 which is selected from the group consisting of 3-[4-(4-Bromophenyl)-1,3-thiazol-2-yl]-4,4-dimethyl-1,3-oxazolidin-2-one, 4-2-(4,4-Dimethyl-2-oxo-1,3-oxazolidin-3-yl)-1,3-thiazol-4-yl]benzonitrile, 3-[4-(4-Bromo-2-fluorophenyl)-1,3-thiazol-2-yl]-4,4-dimethyl-1,3-oxazolidin-2-one, 3-[4-(3-Bromophenyl)-1,3-thiazol-2-yl]-4,4-dimethyl-1,3-oxazolidin-2-one, 3-[4-(4-Chloro-3-fluorophenyl)-1,3-thiazol-2-yl]-4,4-dimethyl-1,3-oxazolidin-2-one, 4-[2-(4,4-Dimethyl-2-oxo-1,3-oxazolidin-3-yl)-1,3-thiazol-4-yl]-3-fluorobenzonitrile, 4,4-Dimethyl-3-[4-(4-nitrophenyl)-1,3-thiazol-2-yl]-1,3-oxazolidin-2-one, 4-[2-(4,4-Dimethyl-2-oxo-1,3-oxazolidin-3-yl)-1,3-thiazol-4-yl]-2-fluorobenzonitrile, 3-[2-(4,4-dimethyl-2-oxo-1,3-oxazolidin-3-yl)-1,3-thiazol-4-yl]benzonitrile, 4-[2-(4,4-Dimethyl-2-oxo-1,3-oxazolidin-3-yl)-1,3-thiazol-4-yl]-N'-hydroxybenzene carboximidamide, 4,4-Dimethyl-3-{4-[4-(trifluoromethyl)phenyl]-1,3-thiazol-2-yl}-1,3-oxazolidin-2-one, 4,4-Dimethyl-3-{4-[3-(trifluoromethyl)phenyl]-1,3-thiazol-2-yl}-1,3-oxazolidin-2-one, 4,4-Dimethyl-3-{4-[4-(trifluoromethoxy)phenyl]-1,3-thiazol-2-yl}-1,3-oxazolidin-2-one, 3-[4-(4-Methoxyphenyl)-1,3-thiazol-2-yl]-4,4-dimethyl-1,3-oxazolidin-2-one, 3-[4-(3-Methoxyphenyl)-1,3-thiazol-2-yl]-4,4-dimethyl-1,3-oxazolidin-2-one, 3-[4-(2-Methoxyphenyl)-1,3-thiazol-2-yl]-4,4-dimethyl-1,3-oxazolidin-2-one, 4,4-Dimethyl-3-[4-(2,46-trifluorophenyl)-1,3-thiazol-2-yl]-1,3-oxazolidin-2-one, 3-{4-[3-(Ethylsulfonyl)phenyl]-1,3-thiazol-2-yl}-4,4-dimethyl-1,3-oxazolidin-2-one, {4-[2-(4,4-Dimethyl-2-oxo-1,3-oxazolidin-3-yl)-1,3-thiazol-4-yl]phenyl}acetonitrile, 3-[4-(4-Acetylphenyl)-1,3-thiazol-2-yl]-4,4-dimethyl-1,3-oxazolidin-2-one, 3-[4-(3-Acetylphenyl)-1,3-thiazol-2-yl]-4,4-dimethyl-1,3-oxazolidin-2-one, 3-[4-(3,4-Dimethoxyphenyl)-1,3-thiazol-2-yl]-4,4-dimethyl-1,3-oxazolidin-2-one, 3-[4-(4-Chlorophenyl)-1,3-thiazol-2-yl]-4,4-dimethyl-1,3-oxazolidin-2-one, 3-[4-(4-Fluorophenyl)-1,3-thiazol-2-yl]-4,4-dimethyl-1,3-oxazolidin-2-one, 3-[4-(3,5-Dichlorophenyl)-1,3-thiazol-2-yl]-4,4-dimethyl-1,3-oxazolidin-2-one, 3-[4-(3-Chloro-4-fluorophenyl)-1,3- thiazol-2-yl]-4,4-dimethyl-1,3-oxazolidin-2-one, 3-[4-(2,4-Dichlorophenyl)-1,3-thiazol-2-yl]-4,4-dimethyl-1,3-oxazolidin-2-one, 3-[4-(3,4-Dichlorophenyl)-1,3-thiazol-2-yl]-4,4-dimethyl-1,3-oxazolidin-2-one, 4,4-Dimethyl-3-(4-phenyl-1,3-thiazol-2-yl)-1,3-oxazolidin-2-one, 4,4-Dimethyl-3-[4-(4-methylphenyl)-1,3-thiazol-2-yl]-1,3-oxazolidin-2-one, 4,4-Dimethyl-3-[4-(2-nitrophenyl)-1,3-thiazol-2-yl]-1,3-oxazolidin-2-one, 4,4-Dimethyl-3-[4-(3-nitrophenyl)-1,3-thiazol-2-yl]-1,3-oxazolidin-2-one, 3-{4-[4-(Benzyloxy)phenyl]-1,3-thiazol-2-yl}-4,4-dimethyl-1,3-oxazolidin-2-one, 3-[4-(4-Fluoro-3-methylphenyl)-1,3-thiazol-2-yl]-4,4-dimethyl-1,3-oxazolidin-2-one, 4,4-Dimethyl-3-[4-(4-phenoxyphenyl)-1,3-thiazol-2-yl]-1,3-oxazolidin-2-one, 3-(4-Biphenyl-4-yl-1,3-thiazol-2-yl)-4,4-dimethyl-1,3-oxazolidin-2-one, and Methyl 4-[2-(4,4-dimethyl-2-oxo-1,3-oxazolidin-3-yl)-1,3-thiazol-4-yl]benzoate.

14. The compound according to claim 1 which is 4-[2-(4,4-Dimethyl-2-oxo-1,3-oxazolidin-3-yl)-1,3-thiazol-4-yl]benzonitrile.

15. The compound according to claim 1 which is selected from the group consisting of 3-[4-(4-Bromophenyl)-1,3-thiazol-2-yl]-5-methyl-1,3-oxazolidin-2-one, 4-[2-(5-Methyl-2-oxo-1,3-oxazolidin-3-yl)-1,3-thiazol-4-yl]benzonitrile, 3-[4-(4-Bromophenyl)-1,3-thiazol-2-yl]-5-ethyl-1,3-oxazolidin-2-one, 4-[2-(5-Ethyl-2-oxo-1,3-oxazolidin-3-yl)-1,3-thiazol-4-yl]benzonitrile, 4-[2-(4,4,5-Trimethyl-2-oxo-1,3-oxazolidin-3-yl)-1,3-thiazol-4-yl]benzonitrile, 4-[2-(2-Oxo-1,3-benzoxazol-3(2H)-yl)-1,3-thiazol-4-yl]benzonitrile, 3-[3-(4-Bromophenyl)-1,2,4-thiadiazol-5-yl]-4,4-dimethyl-1,3-oxazolidin-2-one, 4-[5-(4,4-dimethyl-2-oxo-[3-oxazolidin-3-yl)-1,2,4-thiadiazol-3-yl]benzonitrile, 4-[5-(2-Oxo-1,3-oxazolidin-3-yl)-3-thienyl]benzonitrile, and 4-[2-(4,4-dimethyl-2-oxo-1,3-oxazolidin-3-yl)-1,3-oxazol-4-yl]benzonitrile.

16. The compound according to claim 1 which is selected from the group consisting of 4-[4-(4-Bromophenyl)-1,3-thiazol-2-yl]-6-oxa-4-azaspiro[2.4]heptane-5-one, 4-[2-(5-oxo-6-oxa-4-azaspiro[2.4]hept-4-yl)-1,3-thiazol-4-yl]benzonitrile, 5-[4-(4-Bromophenyl)-1,3-thiazol-2-yl]-7-oxa-5-azaspiro[3.4]octan-6-one, 4-[2-(6-Oxo-7-oxa-5-azaspiro[3.4]oct-5-yl)-1,3-thiazol-4-yl]benzonitrile, 1-[4-(4-Bromophenyl)-1,3-thiazol-2-yl]-3-oxa-1-azaspiro[4.4]nonan-2-one, 4-[2-(2-Oxo-3-oxa-1-azaspiro[4.4]non-1-yl)-1,3-thiazol-4-yl]benzonitrile, and 4-[2-(4,4-Diethyl-2-oxo-1,3-oxazolidin-3-yl)-1,3-thiazol-4-yl]benzonitrile.

17. The compound according to claim 1 which is selected from the group consisting of 4-[2-(4,4-Diethyl-2-oxo-1,3-oxazolidin-3-yl)-5-fluoro-1,3-thiazol-4-yl]benzonitrile, 4-[5-Fluoro-2-(5-oxo-6-oxa-4-azaspiro[2.4]hept-4-yl)-1,3-thiazol-4-yl]benzonitrile, (4S)-3-[4-(4-Bromophenyl)-5-fluoro-1,3-thiazol-2-yl]-4-ethyl-1,3-oxazolidin-2-one, (4S)-3-[4-(4-Bromophenyl)-5-chloro-1,3-thiazol-2-yl]-4-ethyl-1,3-oxazolidin-2-one, 4-{2-[(4S)-4-Ethyl-2-oxo-1,3-oxazolidin-3-yl]-5-fluoro-1,3-thiazol-4-yl}benzonitrile, 4-{5-Chloro-2-[(4S)-4-ethyl-2-oxo-1,3-oxazolidin-3-yl]-1,3-thiazol-4-yl}benzonitrile, 4-(4-Cyanophenyl)-2-[(4S)-4-ethyl-2-oxo-1,3-oxazolidin-3-yl]-1,3-thiazole-5-carbonitrile, 3-[4-(4-Bromophenyl)-5-methyl-1,3-thiazol-2-yl]-4,4-dimethyl-1,3-oxazolidin-2-one, 4-[2-(4,4-dimethyl-2-oxo-1,3-oxazolidin-3-yl)-5-fluoro-1,3-thiazol-4-yl]benzonitrile, 4-[2-(4,4-Dimethyl-2-oxo-1,3-oxazolidin-3-yl)-5-methyl-1,3-thiazol-4-yl]benzonitrile, 4-[5-Chloro-2-(4,4-dimethyl-2-oxo-1,3-oxazolidin-3-yl)-1,3-thiazol-4-yl]benzonitrile, and Methyl 4-[5-chloro-2-(4,4-dimethyl-2-oxo-1,3-oxazolidin-3-yl)-1,3-thiazol-4-yl]benzoate.

18. The compound according to claim 1 which is selected from the group consisting of 4-Bromo-5-[2-(4,4-dimethyl-2-oxo-1,3-oxazolidin-3-yl)-1,3-thiazol-4-yl]thiophene-2-carbonitrile, 4-[2-(4,4-Dimethyl-2-oxo-1,3-oxazolidin-3-yl)-1,3-thiazol-4-yl]thiophene-2-carbonitrile, 5-[2-(4,4-dimethyl-2-oxo-1,3-oxazolidin-3-yl)-1,3-thiazol-4-yl]thiophene-2-carbonitrile, 4-[2-(4,4-Dimethyl-2-oxo-1,3-oxazolidin-3-yl)-1,3-thiazol-4-yl]-1-methyl-1H-pyrrole-2-carbonitrile, 5-[2-(4,4-Dimethyl-2-oxo-1,3-oxazolidin-3-yl)-1,3-thiazol-4-yl]-1-methyl-1H-pyrrole-3-carbonitrile, 3-[4-(3-Furyl)-1,3-thiazol-2-yl]-4,4-dimethyl-1,3-oxazolidin-2-one, 3-[4-(1H-Indol-5-yl)-1,3-thiazol-2-yl]-4,4-dimethyl-1,3-oxazolidin-2-one, and 4,4-Dimethyl-3-[4-(2-naphthyl)-1,3-thiazol-2-yl]-1,3-oxazolidin-2-one.

19. The compound according to claim 1 which is 4-[2-(4,4-Dimethyl-2-thioxo-1,3-oxazolidin-3-yl)-1,3-thiazol-4-yl]benzonitrile.

20. A compound of the structure:

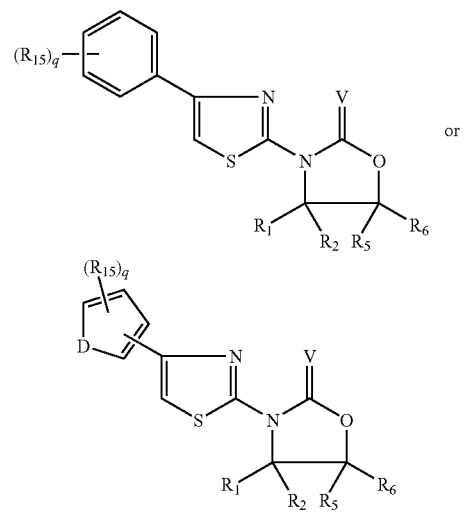

wherein:
$R_1$ and $R_2$ are, independently, H, $C_1$ to $C_{10}$ alkyl, —$(CH_2)_n$-aryl, —$(CH_2)_p$—O—$(CH_2)_n$-aryl, —$(CH_2)_n C(H)_{3-p}(R_7)_p$, or —$(CH_2)_n COOR_8$;

$R_5$ and $R_6$ are H or $R_1$, $R_2$ or $R_5$, $R_6$ are taken together to form a carbon-based 3 to 6 membered saturated ring; or $R_1$ or $R_2$ forms a carbon-based 5 to 7 membered saturated ring with $R_5$ or $R_6$; or $R_1$ or $R_2$ forms a carbon-based 6-membered aromatic ring with $R_5$ or $R_6$;

$R_7$ is halogen;

$R_8$ is $C_1$ to $C_6$ alkyl;

$R_9$ is H, $C_1$ to $C_6$ alkyl, or $C_1$ to $C_3$ perfluoroalkyl;

D is S, $NR_{16}$, or O;

$R_{15}$ is —$(CH_2)_n CN$, halogen, $NO_2$, —$C(NH_2)$=N—OH, $C_1$ to $C_3$ perfluoroalkyl, $C_1$ to $C_3$ perfluoroalkoxy, —O—($C_1$ to $C_4$ alkyl), —$SO_2$—($C_1$ to $C_4$ alkyl), —CO—($C_1$ to $C_4$ alkyl), $C_1$ to $C_4$ alkyl, —O—$(CH_2)_n$-aryl, —CONH—($C_1$ to $C_3$ alkyl), —CON—($C_1$ to $C_3$ alkyl)$_2$, aryl, —COO—($C_1$ to $C_4$ alkyl), or heteroaryl;

$R_{16}$ is H, $C_1$ to $C_{10}$ alkyl, $C_1$ to $C_{10}$ substituted alkyl, or —COO—($C_1$ to $C_{10}$ alkyl);

V is O or S;
n is 0 to 3;
p is 1 to 3;
q is 0 to 3;
or a pharmaceutically acceptable salt or tautomer thereof.

21. The compound according to claim 20, wherein $R_1$, $R_2$, $R_5$ and $R_6$ are, independently, H or $C_1$ to $C_{10}$ alkyl.

22. A compound of the structure:

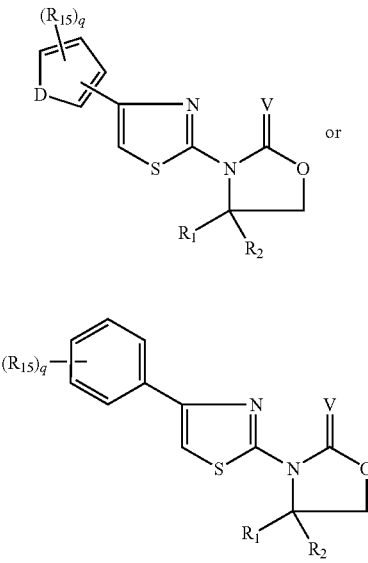

wherein:
$R_1$ and $R_2$ are, independently, H, $C_1$ to $C_{10}$ alkyl, —$(CH_2)_n$-aryl, —$(CH_2)_p$—O—$(CH_2)_n$-aryl, —$(CH_2)_n C(H)_{3-p}(R_7)_p$, or —$(CH_2)_n COOR_8$; or $R_1$ and $R_2$ are taken together to form a carbon-based 3 to 6-membered saturated ring;

$R_7$ is halogen;

$R_8$ is $C_1$ to $C_6$ alkyl;

$R_9$ is H, $C_1$ to $C_6$ alkyl, or $C_1$ to $C_3$ perfluoroalkyl;

D is S, $NR_{16}$, or O;

$R_{15}$ is —$(CH_2)_n CN$, halogen, $NO_2$, —$C(NH_2)$=N—OH, $C_1$ to $C_3$ perfluoroalkyl, $C_1$ to $C_3$ perfluoroalkoxy, —O—($C_1$ to $C_4$ alkyl), —$SO_2$—($C_1$ to $C_4$ alkyl), —CO—($C_1$ to $C_4$ alkyl), $C_1$ to $C_4$ alkyl, —O—$(CH_2)_n$-aryl, —CONH—($C_1$ to $C_3$ alkyl), —CON—($C_1$ to $C_3$ alkyl)$_2$, aryl, —COO—($C_1$ to $C_4$ alkyl), or heteroaryl;

$R_{16}$ is H, $C_1$ to $C_{10}$ alkyl, $C_1$ to $C_{10}$ substituted alkyl, or —COO—($C_1$ to $C_{10}$ alkyl);

V is O or 3;
n is 0 to 3;
p is 1 to 3;
q is 0 to 3;
or a pharmaceutically acceptable salt or tautomer thereof.

23. The compound according to claim 22, wherein $R_1$ and $R_2$ are, independently, H or $C_1$ to $C_{10}$ alkyl.

24. A pharmaceutical composition comprising a compound of claim 1 and a pharmaceutically acceptable carrier.

* * * * *